United States Patent
Reichard et al.

(10) Patent No.: US 7,122,677 B2
(45) Date of Patent: Oct. 17, 2006

(54) NK$_1$ ANTAGONISTS

(75) Inventors: Gregory A. Reichard, Ann Arbor, MI (US); Sunil Paliwal, Scotch Plains, NJ (US); Neng-Yang Shih, North Caldwell, NJ (US); Dong Xiao, Warren, NJ (US); Hon-Chung Tsui, East Brunswick, NJ (US); Sapna Majmundar Shah, Jamesburg, NJ (US); Cheng Wang, Summit, NJ (US); Michelle Laci Wrobleski, Whitehouse Station, NJ (US)

(73) Assignee: Scherig Corporation, Kenilworth, NJ (US)

( * ) Notice: Subject to any disclaimer, the term of this patent is extended or adjusted under 35 U.S.C. 154(b) by 350 days.

(21) Appl. No.: 10/292,618

(22) Filed: Nov. 12, 2002

(65) Prior Publication Data

US 2003/0144270 A1 Jul. 31, 2003

Related U.S. Application Data

(60) Provisional application No. 60/337,652, filed on Nov. 13, 2001.

(51) Int. Cl.
*C07D 207/00* (2006.01)
*C07D 209/96* (2006.01)
*C07D 225/00* (2006.01)
*C07D 215/00* (2006.01)
*A01N 57/00* (2006.01)

(52) U.S. Cl. .................. 548/407; 540/450; 540/451; 540/453; 540/466; 540/531; 540/543; 540/609; 546/16; 546/19; 546/20; 546/229; 546/236; 514/79; 514/85; 514/91; 548/408; 548/410

(58) Field of Classification Search ............... 548/407; 548/408, 410; 540/450, 451, 531, 543, 609; 546/16, 19, 229; 514/91, 85, 79
See application file for complete search history.

(56) References Cited

U.S. PATENT DOCUMENTS

| 5,620,989 A | 4/1997 | Harrison et al. |
| 5,760,018 A | 6/1998 | Baker et al. |
| 6,162,805 A | 12/2000 | Hefti |

FOREIGN PATENT DOCUMENTS

| WO | WO 94/10165 | 5/1994 |
| WO | WO 94/13639 | 6/1994 |
| WO | WO 01/44200 | 6/2001 |

OTHER PUBLICATIONS

Wu, Xiujuan et al., "Stereoselective transformation of 2H–1, 4–oxazin–2–ones into 2, (2),5,5–tri– and tetrasubstituted analogues of cis–5–hydroxy–2–piperidinemethanol and cis–5–hydroxy–6–oxo–2–piperidinecarboxylic", Tetrahedron (2000), 56 (19), 3043–3051.*

U.S. Appl. No. 10/321,687, filed Dec. 17, 2002, Paliwal et al.

Kramer et al, *Science, 281* (1998), 1640–1645.

Gonzales et al, *Oncology Special Edition, 5* (2002), 53–58.

Cogan e al, *Tetrahedron, 55* (1999), 8883–8904.

Cativiela et al, *Tetrahedron: Asymmetry, 9* (1998), 3517–3599.

Seebach et al, *Modern Synthetic Methods 1986, vol. 4* (Springer–Verlag, Berlin, 1986), p. 125–259.

O'Donnell et al, *Heterocycles, 46* (1997), 617–630.

Wu et al, *Tetrahedron, 56*, 19 (2000), 3043–3051.

Xiujuan Wu et al, Stereoselective Transformation of 2H–1, 4–Oxazin–2–ones into 2,(2),5,5–Tri– and Tetrasubstituted Analogues of cis–5–Hydroxy–2–piperidinemethanol and cis–5–Hydroxy–6–oxo–2–piperidinecarboxylic Acid, *Tetrahedron* 2000, 56: 3043–3051.

PCT International Search Report dated Nov. 12, 2002 for corresponding PCT Application No. PCT/US02/36186.

XP–02232295—Wu, Xiujuan; Dubois, Krisotof: Rogiers, Joeri; Toppet; Suzanne: Compernolle Frans; Hoomaert, Georges J., Stereoselective Transformation of 2H–1, 4–Oxazin–2–ones into 2,(2),5,5–Tri– and Tetrasubstituted Analogues of cis–5–Hydroxy–2–piperidinemethanol and cis–5–Hydroxy–6–oxo–2–piperidinecarboxylic Acid, *Elsevier Science Ltd, Journal Tetrahedron* 2000, 56; 3043–3051 CODEN: TETRAB; ISSN: 0040–4020.

* cited by examiner

*Primary Examiner*—Richard Raymond
*Assistant Examiner*—Paul V. Ward
(74) *Attorney, Agent, or Firm*—Serena Farquharson-Torres

(57) ABSTRACT

A NK$_1$ antagonist having the formula (I),

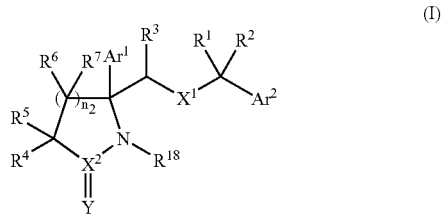

wherein $Ar^1$ and $Ar^2$ are optionally substituted phenyl or heteroaryl, $X^1$ is an ether, thio or imino linkage, $R^4$ and $R^5$ are not both H or alkyl, and the remaining variables are as defined in the in the specification, useful for treating a number of disorders, including emesis, depression, anxiety and cough. Pharmaceuticals compositions. Methods of treatment and combinations with other agents are also disclosed.

23 Claims, No Drawings

NK₁ ANTAGONISTS

CROSS REFERENCE TO RELATED APPLICATIONS

This application claims the benefit of U.S. Provisional Application No. 60/337,652, filed Nov. 13, 2001.

BACKGROUND OF THE INVENTION

1. Field of the Invention

The invention relates to an antagonist of the neuropeptide neurokinin-1 ($NK_1$) receptor.

2. Description of Related Art

Tachykinins are peptide ligands for neurokinin receptors. Neurokinin receptors, such as $NK_1$, $NK_2$ and $NK_3$, are involved in a variety of biological processes. They can be found in a mammal's nervous and circulatory systems, as well as in peripheral tissues. Consequently, the modulation of these types of receptors have been studied to potentially treat or prevent various mammalian disease states. For instance, $NK_1$ receptors have been reported to be involved in microvascular leakage and mucus secretion. Representative types of neurokinin receptor antagonists and their uses can be found in U.S. Pat. No. 5,760,018 (1998) (pain, inflammation, migraine and emesis), U.S. Pat. No. 5,620,989 (1997) (pain, nociception and inflammation), WO 94/13639 (1994) (same) and WO 94/10165 (1994) (same).

It would be beneficial to provide a $NK_1$ antagonist that is potent, selective, and possesses beneficial therapeutic and pharmacological properties, and good metabolic stability. It would further be beneficial to provide a $NK_1$ antagonist that is effective for treating a variety of physiological disorders, symptoms and diseases while minimizing side effects. The invention seeks to provide these and other benefits, which will become apparent as the description progresses.

SUMMARY OF THE INVENTION

In one aspect of the invention, a compound is provided having the formula (I):

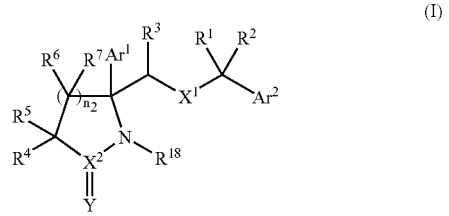

(I)

or a pharmaceutically-acceptable salt thereof, where $Ar^1$ and $Ar^2$ are each independently selected from the group consisting of $R^{17}$-heteroaryl- and

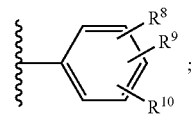

;

$X^1$ is —O—, —S—, —SO—, —$SO_2$—, —$NR^{18a}$—, —$N(COR^{12})$— or —$N(SO_2R^{15})$—;

$X^2$ is C, S or SO;

when $X^2$ is C, then Y is O, S or $NR^{11}$;

when $X^2$ is S or SO, then Y is O, when $X^1$ is —SO—, —$SO_2$—, —$N(COR^{12})$— or —$N(SO_2R^{15})$—, then:

$R^1$ and $R^2$ are each independently selected from the group consisting of H, —$C_1$–$C_6$ alkyl, hydroxy($C_1$–$C_3$alkyl)-, —$C_3$–$C_8$ cycloalkyl, —$C_4$–$C_8$ cycloalkylalkyl, —$CH_2F$, —$CHF_2$ and —$CF_3$; or $R^1$ and $R^2$, together with one another and the carbon to which they are both attached, form a chemically feasible $C_3$–$C_6$ alkylene ring;

when $X^1$ is —O—, —S— or —$NR^{18a}$—; then:

$R^1$ and $R^2$ are each independently selected from the group consisting of H, —$C_1$–$C_6$ alkyl, hydroxy($C_1$–$C_3$alkyl)-, —$C_3$–$C_8$ cycloalkyl, —$C_4$–$C_8$ cycloalkylalkyl, —$CH_2F$, —$CHF_2$ and —$CF_3$; or $R^1$ and $R^2$, together with one another and the carbon to which they are both attached, form a chemically feasible $C_3$–$C_6$ alkylene ring; or $R^1$ and $R^2$, together with one another and the carbon to which they are both attached, form a C=O group;

$R^3$ is selected from the group consisting of H, —$C_1$–$C_6$ alkyl, hydroxy-($C_1$–$C_3$ alkyl)-, —$C_3$–$C_8$ cycloalkyl, —$CH_2F$, —$CHF_2$ and —$CF_3$;

each $R^6$ is independently selected from the group consisting of H, —$C_1$–$C_6$ alkyl, —$OR^{13}$ and —$SR^{18}$;

each $R^7$ is independently selected from the group consisting of H and $C_1$–$C_6$ alkyl; or $R^6$ and $R^7$, together with one another and the carbon to which they are both attached, form a C=O group;

$n_2$ is from 1 to 4;

$R^4$ and $R^5$ are each independently selected from the group consisting of —$(CR^{28}R^{29})_{n1}$-G and —$C(O)(CR^{28}R^{29})_{n4}$-G, where, $n_1$ is from 0 to 5;

$n_4$ is from 1 to 5; and

G is H, —$CF_3$, —$CHF_2$, —$CH_2F$, —OH, —O—($C_1$–$C_6$ alkyl), —$SO_2R^{13}$, —O—($C_3$–$C_8$ cycloalkyl), —$NR^{13}R^{14}$, —$SO_2NR^{13}R^{14}$, —$NR^{13}SO_2R^{15}$, —$NR^{13}COR^{12}$, —$NR^{12}(CONR^{13}R^{14})$, —$NR^{12}COC(R^{12})_2NR^{13}R^{14}$, —$CONR^{13}R^{14}$, —$COOR^{12}$, —$C_3$–$C_8$ cycloalkyl, $(R^{19})_r$aryl-, $(R^{19})_r$heteroaryl-, —$OC(O)R^{14}$, —$OC(O)NR^{13}R^{14}$,

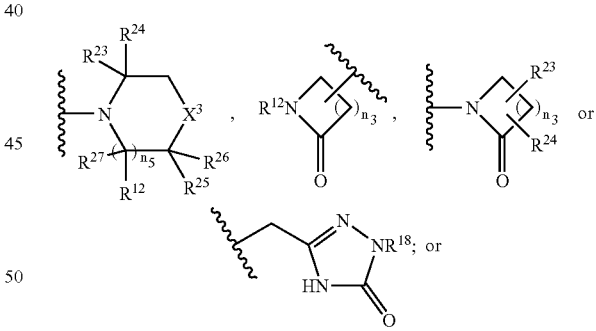

$R^4$ and $R^5$, together with one another and the carbon to which they are both attached, form a C=O or C=$NR^{12}$ group; or $R^4$ and $R^5$, together with one another and the carbon to which they are both attached, form a chemically feasible 4- to 7-membered ring containing from 0 to 3 heteroatoms that are each independently selected from the group consisting of —O—, —S—, —S(O)—, —$SO_2$— and —$NR^{18}$—, the chemically feasible ring being optionally substituted with from 1 to 2 substituents that are independently selected from the group consisting of $R^{30}$ and $R^{31}$; or when $R^4$ and $R^5$ do not form a ring, and $n_2$ is 1 or 2, then $R^4$ and $R^6$ or $R^4$ and $R^7$, which are on adjacent carbons, can form a bond;

$X^3$ is —$NR^{20}$—, —$N(CONR^{13}R^{14})$—, —$N(CO_2R^{13})$—, —$N(SO_2R^{15})$—, —$N(COR^{12})$—, —$N(SO_2NHR^{13})$—, —O—, —S—, —S(O)—, —SO_2—, —CH_2—, —CF_2— or —$CR^{12}F$—;

$R^8$, $R^9$ and $R^{10}$ are each independently selected from the group consisting of H, —$C_1$–$C_6$ alkyl, —$C_3$–$C_8$ cycloalkyl, —$OR^{18}$, halogen, —CN, —$NO_2$, —$CF_3$, —$CHF_2$, —$CH_2F$, —$CH_2CF_3$, —$OCF_3$, —$OCHF_2$, —$OCH_2F$, —$OCH_2CF_3$, —$COOR^{12}$, —$CONR^{21}R^{22}$, —$NR^{21}COR^{12}$, —$NR^{21}CO_2R^{15}$, —$NR^{21}CONR^{21}R^{22}$, —$NR^{21}SO_2R^{15}$, —$NR^{21}R^{22}$, —$SO_2NR^{21}R^{22}$, —$S(O)_{n5}R^{15}$, $(R^{19})_r$aryl- and $(R^{19})_r$heteroaryl-;

$R^{11}$ is H, —$C_1$–$C_6$ alkyl, —$C_3$–$C_8$ cycloalkyl, —$C_4$–$C_8$ cycloalkylalkyl, —$NO_2$, —CN or —$OR^{18}$;

$R^{12}$ is H, —$C_1$–$C_6$ alkyl, —$C_3$–$C_8$ cycloalkyl or —$C_4$–$C_8$ cycloalkylalkyl;

$R^{13}$ and $R^{14}$ are each independently selected from the group consisting of H, —$C_1$–$C_6$ alkyl, —$C_3$–$C_8$ cycloalkyl or —$C_4$–$C_8$ cycloalkylalkyl; or $R^{13}$ and $R^{14}$, together with one another, form a chemically feasible —$C_3$ to —$C_6$ alkylene chain, and with the nitrogen to which they are both attached, form a chemically feasible 4- to 7-membered ring that is, optionally, substituted with —$OR^{12}$, where one of the carbon atoms in the chemically feasible $C_3$–$C_6$ alkylene chain is, optionally, replaced by a heteroatom selected from the group consisting of —O—, —S— and —$NR^{18}$—;

$R^{15}$ is —$C_1$–$C_6$ alkyl, —$C_3$–$C_8$ cycloalkyl, —$C_4$–$C_8$ cycloalkylalkyl or —$CF_3$;

$R^{17}$ is H, —$C_1$–$C_6$ alkyl, —$C_3$–$C_8$ cycloalkyl, —$C_4$–$C_8$ cycloalkylalkyl, —$COOR^{12}$, —$CONR^{21}R^{22}$, —$NR^{21}R^{22}$, —$NR^{21}COR^{12}$, —$NR^{21}CO_2R^{12}$, —$NR^{21}CONR^{21}R^{22}$, —$NR^{21}SO_2R^{15}$ or —$S(O)_{n5}R^{15}$;

each $R^{18}$ is independently selected from the group consisting of H, —$C_1$–$C_6$ alkyl, —$C_3$–$C_8$ cycloalkyl, —$C_4$–$C_8$ cycloalkylalkyl and —$P(O)(OH)_2$;

each $R^{18a}$ is independently selected from the group consisting of H, —$C_1$–$C_6$ alkyl, —$C_3$–$C_8$ cycloalkyl and —$C_4$–$C_8$ cycloalkylalkyl;

each $R^{19}$ is a substituent on the aryl or heteroaryl ring to which it is attached, and is independently selected from the group consisting of H, —$C_1$–$C_6$ alkyl, —$C_3$–$C_8$ cycloalkyl, —$C_4$–$C_8$ cycloalkylalkyl, —$C_1$–$C_6$ alkoxy, —OH, halogen, —CN, —$NO_2$, —$CF_3$, —$CHF_2$, —$CH_2F$, —$OCF_3$, —$OCHF_2$, —$OCH_2F$, —O—($C_1$–$C_6$ alkyl), —O—($C_3$–$C_8$ cycloalkyl), —$COOR^{12}$, —$CONR^{21}R^{22}$, —$NR^{21}R^{22}$, —$NR^{21}COR^{12}$, —$NR^{21}CO_2R^{12}$, —$NR^{21}CONR^{21}R^{22}$, —$NR^{21}SO_2R^{15}$ and —$S(O)_{n5}R^{15}$;

r is from 1 to 3;

$R^{20}$ is H, —$C_1$–$C_6$ alkyl, —$C_3$–$C_8$ cycloalkyl, —$C_4$–$C_8$ cycloalkylalkyl or —$(CH_2)_{n6}$— heterocycloalkyl;

$R^{21}$ and $R^{22}$ are each independently selected from the group consisting of H, —$C_1$–$C_6$ alkyl, —$C_3$–$C_8$ cycloalkyl, —$C_4$–$C_8$ cycloalkylalkyl and benzyl; or $R^{21}$ and $R^{22}$, together with one another, form a chemically feasible —$C_3$–$C_6$ alkylene chain, and with the nitrogen to which they are both attached, form a chemically feasible 4- to 7-membered ring, where one of the carbon atoms in the chemically feasible —$C_3$–$C_6$ alkylene chain is, optionally, replaced by a heteroatom selected from the group consisting of —O—, —S— and —$NR^{18}$—;

$R^{23}$ and $R^{24}$ are each independently selected from the group consisting of H and —$C_1$–$C_6$ alkyl; or $R^{23}$ and $R^{24}$, together with one another and the carbon to which they are both attached, form a C=O or cyclopropyl group;

$R^{25}$ and $R^{26}$ are each independently selected from the group consisting of H and —$C_1$–$C_6$ alkyl; or $R^{25}$ and $R^{26}$, together with one another and the carbon to which they are both attached, form a C=O or cyclopropyl group;

$R^{27}$ is H or —$C_1$–$C_6$ alkyl;

$R^{28}$ and $R^{29}$ are each independently selected from the group consisting of H, —$C_1$–$C_2$ alkyl, —$CH_2F$, —$CHF_2$ and —$CF_3$;

$R^{30}$ and $R^{31}$ are each independently selected from the group consisting of H, —$C_1$–$C_2$ alkyl, —$CH_2F$, —$CHF_2$ and —$CF_3$; or $R^{30}$ and $R^{31}$, together with one another and the carbon to which they are both attached, form a C=O or cyclopropyl group;

$n_3$ is from 1 to 5;

$n_5$ is from 0 to 2; and $n_6$ is from 0 to 3;

provided that, when $n_5$ is 0, and $R^{25}$ and $R^{28}$ are each H, then $X^3$ is —$CH_2$—, —$CF_2$—or —$CR^{12}F$—.

The invention comprises at least one compound having the formula (I), including any and all diastereomers, enantiomers, stereoisomers, regiostereomers, rotomers, tautomers and prodrugs thereof, and their corresponding salts, solvates (e.g., hydrates), esters, and the like. The invention further comprises pharmaceutically-acceptable compositions prepared from an inventive compound or a mixture of inventive compounds, or a salt, solvate, ester, etc., thereof. The compounds having the formula (I) can be useful for treating a variety of diseases, symptoms and physiological disorders, such as emesis, depression, anxiety and cough. Another aspect of the invention comprises a pharmaceutical composition comprising a compound of formula (I), alone or with another active agent, and a pharmaceutically acceptable carrier or excipient therefor. The inventive compounds and compositions can be used alone or in combination with other active agents and/or methods of treatment for treating a variety of diseases, symptoms and physiological disorders, such as the ones disclosed herein.

DETAILED DESCRIPTION

The following definitions and terms are used herein or are otherwise known to a skilled artisan. Except where stated otherwise, the following definitions apply throughout the specification and claims. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

The term "substituted," as used herein, means the replacement of one or more atoms or radicals, usually hydrogen atoms, in a given structure with an atom(s) or radical(s) selected from a specified group. In the situations where more than one atom or radical may be replaced with a substituent selected from the same specified group, the substituents may be, unless otherwise specified, either the same or different at every position.

The term "heteroatom," as used herein, means a nitrogen, sulfur, or oxygen atom. Multiple heteroatoms in the same group may be the same or different.

The term "alkyl," as used herein, means a straight or branched, hydrocarbon chain. Unless stated otherwise, the hydrocarbon chain has, preferably, from one to twenty-four carbon atoms, more preferably, from one to twelve carbon atoms, even more preferably, from one to eight carbon atoms, and yet even more preferably, from one to six carbon atoms.

The term "cycloalkyl," as used herein, means a saturated, stable non-aromatic carbocyclic ring, having, preferably, from three to fifteen carbon atoms, more preferably, from three to eight carbon atoms. The cycloalkyl may be attached at any endocyclic carbon atom that results in a stable structure. Preferred carbocycles have from five to six carbons. Examples of carbocycle radicals include cyclopropyl, cyclobutyl, cyclopentyl, cyclohexyl, cycloheptyl and the like.

The term "aryl," as used herein, means an aromatic, mono- or bicyclic carbocyclic ring system having from one to two aromatic rings. The aryl moiety will generally have from 6 to 14 carbon atoms with all available substitutable carbon atoms of the aryl moiety being intended as possible points of attachment. Representative examples include phenyl, cumenyl, naphthyl, tetrahydronaphthyl, indanyl, indenyl and the like.

The term "heteroaryl," as used herein, means a mono- or bicyclic ring system containing one or two aromatic rings and at least one nitrogen, oxygen or sulfur atom in an aromatic ring. Typically, a heteroaryl group represents a cyclic group of five or six atoms, or a bicyclic group of nine or ten atoms, at least one of which is carbon, and having at least one oxygen, sulfur or nitrogen atom interrupting a carbocyclic ring having a sufficient number of pi ($\pi$) electrons to provide aromatic character. Representative heteroaryl (heteroaromatic) groups are pyridinyl, pyrimidinyl, pyrazinyl, pyridazinyl, furanyl, benzofuranyl, thienyl, benzothienyl, thiazolyl, thiadiazolyl, imidazolyl, pyrazolyl, triazolyl, isothiazolyl, benzothiazolyl, benzoxazolyl, oxazolyl, pyrrolyl, isoxazolyl, 1,3,5-triazinyl and indolyl groups.

The term "heterocycloalkyl," as used herein, means a saturated cyclic ring system having from three to fifteen members, preferably, from three to eight members, and comprising carbon atoms and 1–2 heteroatoms as part of the ring. Examples of heterocycloalkyl rings are piperidinyl, pyrazinyl, and morpholinyl.

Unless otherwise known, stated or shown to be to the contrary, the point of attachment for a multiple term substituent (multiple terms that are combined to identify a single moiety) to a subject structure is through the last named term of the multiple term. For example, an "arylalkyl" substituent attaches to a targeted structure through the "alkyl" portion of the substituent. Conversely, when the substituent is "alkylaryl", it attaches to a targeted structure through the "aryl" portion of the substituent. Similarly, a cycloalkylalkyl substituent attaches to a targeted through the latter "alkyl" portion of the substituent (e.g., Structure-alkylcycloalkyl).

The term "alkoxy," as used herein, means an oxygen atom bonded to an alkyl group. Representative alkoxy groups include methoxy, ethoxy and isopropoxy groups.

The term "hydroxyalkyl," as used herein, means an alkyl group having at least one hydroxy substituent (e.g., —OH). Representative hydroxyalkyl groups include hydroxymethyl, hydroxyethyl and hydroxypropyl groups.

The term "halo" or "halogen" as used herein, means a chloro, bromo, fluoro or iodo atom radical.

When $R^4$ and $R^6$ or $R^4$ and $R^7$ are on adjacent carbons and form a bond, examples of the resultant partial structures are:

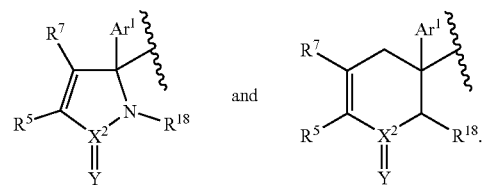

When a variable occurs more than one time in any constituent (e.g., $R^8$), its definition on each occurrence is independent of its definition at every other occurrence. Also, combinations of substituents and/or variables are permissible only if such combinations result in stable compounds.

The term "chemically-feasible" is usually applied to a ring structure present in a compound and means that the ring structure would be expected to be stable by a skilled artisan.

The term "prodrug," as used herein, represents compounds that are drug precursors which, following administration to a patient, release the drug in vivo via a chemical or physiological process (e.g., a prodrug on being brought to a physiological pH or through an enzyme action is converted to the desired drug form). A discussion of prodrugs is provided in T. Higuchi and V. Stella, *Pro-drugs as Novel Delivery Systems,* Vol. 14 of A.C.S. Symposium Series (1987), and in *Bioreversible Carriers in Drug Design,* E. B. Roche, ed., American Pharmaceutical Association and Pergamon Press (1987), each of which is incorporated herein by reference in its entirety.

As used herein, the term "composition" is intended to encompass a product comprising the specified ingredients in the specified amounts, as well as any product which results, directly or indirectly, from combination of the specified ingredients in the specified amounts.

Other than as shown in the operating examples or where is otherwise indicated, all numbers used in the specification and claims expressing quantities of ingredients, reaction conditions, and so forth, are understood as being modified in all instances by the term "about."

Referring to the compound having the formula (I):

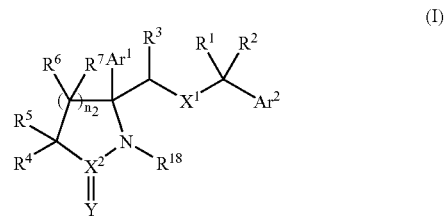

or a pharmaceutically-acceptable salt thereof,
a preferred embodiment of the invention may contain one or more of the following moieties:
$Ar^1$ and $Ar^2$ are each, preferably,

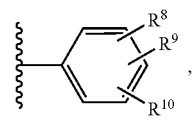

where, $R^8$, $R^9$ and $R^{10}$ are defined the same as above.
More preferably, $R^8$, $R^9$ and $R^{10}$ are each independently selected from the group consisting of: H, —$C_1$–$C_6$ alkyl, —$C_3$–$C_8$ cycloalkyl, —$OR^{18}$, halogen, —CN, —$NO_2$, —CF$_3$, —CHF$_2$, —CH$_2$F, —CH$_2$CF$_3$, —OCF$_3$, —OCHF$_2$, —OCH$_2$F and —OCH$_2$CF$_3$. Even more preferably, R$^8$, R$^9$ and R$^{10}$, are each independently selected from the group consisting of: H, —C$_1$–C$_6$ alkyl, —OH, halogen, —CF$_3$, —CHF$_2$ and —CH$_2$F.

X$^1$ is preferably —O— or —NR$^{18a}$—. More preferably, X$^1$ is —O—.

X$^2$ is preferably C or S. More preferably, X$^2$ is C.

When X$^2$ is C, Y is preferably O or S. More preferably, Y is O when X$^2$ is C.

R$^1$ and R$^2$ are each, preferably, independently selected from the group consisting of H, —C$_1$–C$_6$ alkyl, hydroxy (C$_1$–C$_3$ alkyl), —C$_3$–C$_8$ cycloalkyl, —CH$_2$F, —CHF$_2$ and —CF$_3$. More preferably, R$^1$ and R$^2$ are each independently selected from the group consisting of H and —C$_1$–C$_6$ alkyl.

R$^3$ is preferably selected from the group consisting of H, —C$_1$–C$_6$ alkyl, —CH$_2$F, —CHF$_2$ and —CF$_3$. More preferably, R$^3$ is H or —C$_1$–C$_6$ alkyl.

Each R$^6$ is preferably independently selected from the group consisting of H, —C$_1$–C$_6$ alkyl and —OR$^3$. More preferably, each R$^6$ is independently selected from the group consisting of H and —C$_1$–C$_6$ alkyl.

n$_2$ is preferably 1, 2 or 3. More preferably, n$_2$ is 1 or 2.

R$^4$ and R$^5$ are each preferably —(CR$^{28}$R$^{29}$)$_{n1}$-G, where, n$_1$, is 0, 1 or 2; and G is H, —CF$_3$, —CHF$_2$, —CH$_2$F, —OH, —O—(C$_1$–C$_6$ alkyl), —SO$_2$R$^{13}$, —O—(C$_3$–C$_8$ cycloalkyl), —NR$^{13}$R$^{14}$, —SO$_2$NR$^{13}$R$^{14}$, —NR$^{13}$SO$_2$R$^{15}$, —NR$^{13}$COR$^{12}$, —NR$^{12}$(CONR$^{13}$R$^{14}$), —CONR$^{13}$R$^{14}$, —COOR$^{12}$, —C$_3$–C$_8$ cycloalkyl, (R$^{19}$)$_r$aryl-, (R$^{19}$)$_r$heteroaryl-,

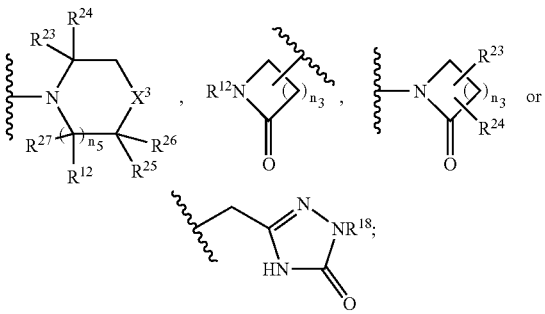

More preferably, R$^4$ and R$^5$ are —(CR$^{28}$R$^{29}$)$_{n1}$-G, where, n$_1$ is 0 or 1; and G is H, —CF$_3$, —CHF$_2$, —CH$_2$F, —OH, —NR$^{13}$COR$^{12}$, —NR$^{12}$(CONR$^{13}$R$^{14}$), —CONR$^{13}$R$^{14}$, —COOR$^{12}$, —C$_3$–C$_8$ cycloalkyl, (R$^{19}$)$_r$aryl-, (R$^{19}$)$_r$heteroaryl-,

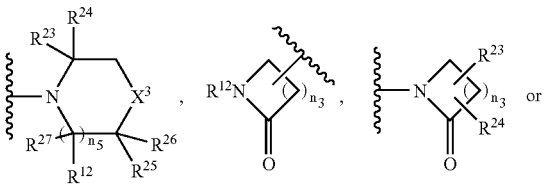

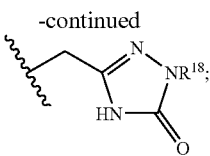

It is also preferable for R$^4$ and R$^5$, together with one another and the carbon to which they are both attached, to form a chemically feasible 4- to 7-membered ring containing from 0 to 3 heteroatoms that are each independently selected from the group consisting of —O—, —S—, —S(O)—, —SO$_2$— and —NR$^{18}$—, the chemically feasible ring being optionally substituted with from 1 to 2 substituents that are each independently selected from the group consisting of R$^{30}$ and R$^{31}$. In such cases, representative examples of the 4- to 7-membered ring,

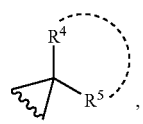

include, but are not limited to the following structures:

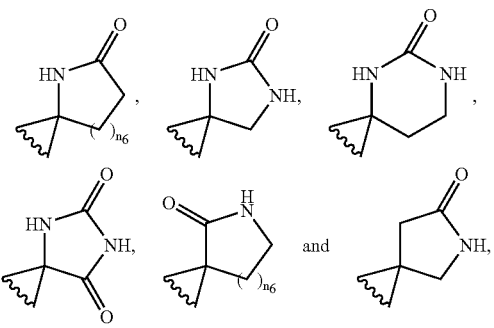

where n$_6$ is defined in the summary of the invention.

X$^3$ is preferably —NR$^{20}$, —O—, —S—, —S(O)—, —SO$_2$—, —CH$_2$—, —CF$_2$— or —CR$^{12}$F—. More preferably, X$^3$ is —O—, —S—, —S(O)—, —SO$_2$—, —CH$_2$—.

R$^{11}$ is preferably H or —C$_1$–C$_6$ alkyl.

R$^{12}$ is preferably H or —C$_1$–C$_6$ alkyl. More preferably, R$^{12}$ is H or CH$_3$.

R$^{13}$ and R$^{14}$ are each preferably independently selected from the group consisting of H and —C$_1$–C$_6$ alkyl. More preferably, R$^{13}$ and R$^{14}$ are each independently selected from the group consisting of H and CH$_3$.

R$^{15}$ is preferably —C$_1$–C$_6$ alkyl or —CF$_3$. More preferably, R$^{15}$ is —C$_1$–C$_6$ alkyl.

R$^{17}$ is preferably H, or —C$_1$–C$_6$ alkyl. More preferably, R$^{17}$ is H or CH$_3$.

R$^{18}$ is preferably H, —C$_1$–C$_6$ alkyl or —P(O)(OH)$_2$. More preferably, R$^{18}$ is H, CH$_3$ or —P(O)(OH)$_2$. R$^{18a}$ is preferably H or C$_1$–C$_6$ alkyl.

Each R$^{19}$ is a substituent on the aryl or heteroaryl ring to which it is attached, and is preferably independently selected from the group consisting of H, —C$_1$–C$_6$ alkyl, —CF$_3$, —CHF$_2$, —CH$_2$F, —OCF$_3$, —OCHF$_2$ and —OCH$_2$F. More preferably, each R$^{19}$ is selected from the group consisting of H and —C$_1$–C$_6$ alkyl.

r is preferably 1 or 2. More preferably, r is 1.

R$^{20}$ is preferably H or —C$_1$–C$_6$ alkyl. More preferably, R$^{20}$ is H or CH$_3$.

$R^{21}$ and $R^{22}$ are each preferably independently selected from the group consisting of H and —$C_1$–$C_6$ alkyl. More preferably, $R^{21}$ and $R^{22}$ are each independently selected from the group H and $CH_3$.

$R^{23}$ and $R^{24}$ are each preferably independently selected from the group consisting of H and —$C_1$–$C_6$ alkyl. More preferably, $R^{23}$ and $R^{24}$ are each independently selected from the group H and $CH_3$.

$R^{25}$ and $R^{26}$ are each preferably independently selected from the group consisting of H and —$C_1$–$C_6$ alkyl. More preferably, $R^{25}$ and $R^{26}$ are each independently selected from the group H and $CH_3$.

$R^{27}$ is preferably H or —$C_1$–$C_6$ alkyl. More preferably, $R^{27}$ is H or $CH_3$.

$R^{28}$ and $R^{29}$ are each preferably independently selected from the group consisting of H and —$C_1$–$C_2$ alkyl. More preferably, $R^{28}$ and $R^{29}$ are each independently selected from the group consisting of H and —$CH_3$ $R^{30}$ and $R^{31}$ are each preferably independently selected from the group consisting of H and —$C_1$–$C_2$ alkyl. More preferably, $R^{30}$ and $R^{31}$ are each independently selected from the group consisting of H and —$CH_3$ $n_3$ is preferably 1, 2 or 3. More preferably, $n_3$ is 1 or 2.

$n_5$ is preferably 0 or 1. More preferably, $n_5$ is 0.

$n_6$ is preferably 0, 1 or 2. More preferably, $n_6$ is 0 or 1.

Referring above to the compounds of formula (I), and the definitions of their substituents, preferred embodiments of the invention may include one or more of the following substituents:

1. $X^1$ is —O—.
2. $X^2$ is —C— and Y is O.
3. $Ar^1$ and $Ar^2$, independently of one another, are each:

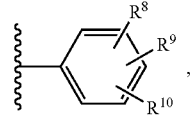

where $R^8$, $R^9$ and $R^{10}$ are each independently defined in the summary of the invention.

4. $Ar^1$ is:

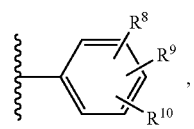

where $R^8$, $R^9$ and $R^{10}$ are each independently selected from the group consisting of H, —OH and halogen; or at least one of $R^8$, $R^9$ and $R^{10}$ is halogen, preferably, F.

5. $Ar^2$ is:

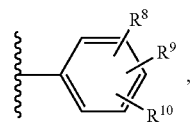

where at least two of $R^8$, $R^9$ and $R^{10}$ are each —$CF_3$.

6. $R^1$ and $R^2$ are each independently selected from the group consisting of:
H and —$C_1$–$C_6$ alkyl.

7. One of $R^1$ and $R^2$ is —$C_1$–$C_6$ alkyl, preferably, —$CH_3$.

8. $R^3$ is H.
9. $n_2$ is 1 or 2.
10. $R^{18}$ is H.
11. $R^6$ and $R^7$ are each H.
12. One of $R^4$ and $R^5$ is H, and the other one of $R^4$ and $R^5$ is selected from the group consisting of:
 (a) —$C(R^{28}R^{29})_{n1}$-G, where $n_1$ is 1, and $R^{28}$, $R^{29}$ and G are each defined in the summary of the invention, for example, $R^{28}$=$R^{29}$=G=H results in —$CH_3$; and
 (b) $C(R^{28}R^{29})_{n1}$-G, where $n_1$ is 0, and G is defined in the summary of the invention, for example:
  (i) G is H;
  (ii) G is —$NR^{13}COR^{12}$, where $R^{13}$ is H results in —$NHCOR^{12}$, where $R^{12}$ is defined in the summary of the invention; if $R^{12}$ is —$CH_3$ or —$CH_2CH_3$, you would get —$NHCOCH_3$ or —$NHCOCH_2CH_3$; and
  (iii) G is:

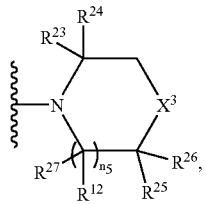

where,
$n_5$ is 0;
$R^{23}$ and $R^{24}$, together with one another and the carbon to which they are both attached, form a C=O group;
$R^{12}$=$R^{27}$=$R^{25}$=$R^{26}$=H; and
$X^3$ is —$CH_2$—, which results in:

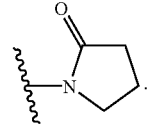

A preferred embodiment of the invention is a compound having the formula (I) with the following substituents:

$R^1$ and $R^2$ are each independently defined in the summary of the invention;

$X^1$ is defined in the summary of the invention;

$R^3$ is H;

$Ar^1$ and $Ar^2$, independently of one another, are each

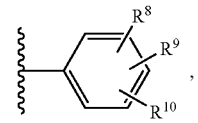

where $R^8$, $R^9$ and $R^{10}$, independently of one another, are each H, —OH, —$CF_3$ or halogen;

$R^6$ and $R^7$ are each H;

$R^4$ and $R^5$, independently of one another, are each defined in the summary of the invention;

$X^2$ is —C—;

Y is O; and $R^{18}$ is H.

More preferably, the preferred embodiment immediately above has the following substituents: $X^1$ is —O— or —$NR^{18a}$—, $n_2$ is 1 or 2, and $R^4$ and $R^5$ are each independently —$C(R^{28}R^{29})_{n_1}$-G, where $n_1$, $R^{28}$, $R^{29}$ and G are each defined in claim 1. Even more preferably, the preferred embodiment immediately above has the following substituents: $X^1$ is —O— or —$NR^{18a}$—, $n_2$ is 1 or 2, and $R^4$ and $R^5$, together with one another and the carbon to which they are both attached, form a chemically feasible 4- to 7-membered ring selected from the group consisting of:

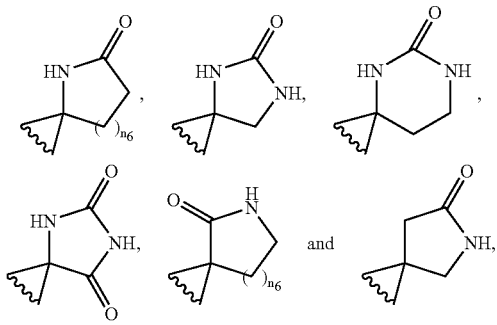

where $n_6$ is defined in claim 1.

The preferred compounds of the invention have the following core structure:

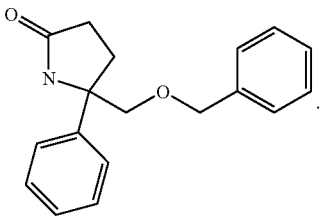

Preferred compounds of the invention include compounds of example numbers: 35, 25a, 26b, 26a, 27a, 23a, 37, 36, 27b, 39a, 25b, 21, 24a, 17, 28, 23b, 15, 40, 39b, 30, 12, 16, 20, 38, 24b, 22, 4, 2a, 29, 14, 9, 2b, 19, 6, 5, 1 and 42a as shown below. More preferred are compounds of example numbers: 25a, 27a, 23a, 17, 15, 40, 4, 35 and 42a.

Compounds having the formula (I) can be effective antagonists of the $NK_1$ receptor, and of an effect of its endogenous agonist, Substance P, at the $NK_1$ receptor site, and therefore, can be useful in treating conditions caused or aggravated by the activity of said receptor. The in vitro and in vivo $NK_1$, $NK_2$ and $NK_3$ activities of the compounds having the formula (I) can be determined by various procedures known in the art, such as a test for their ability to inhibit the activity of the $NK_1$ agonist Substance P. The percent inhibition of neurokinin agonist activity is the difference between the percent of maximum specific binding ("MSB") and 100%. The percent of MSB is defined by the following equation, wherein "dpm" represents "disintegrations per minute":

$$\% \ MSB = \frac{(\text{dpm of unknown}) - (\text{dpm of nonspecific binding})}{(\text{dpm of total binding}) - (\text{dpm of nonspecific binding})} \times 100.$$

The concentration at which the compound produces 50% inhibition of binding is then used to determine an inhibition constant ("Ki") using the Chang-Prusoff equation.

In vivo activity may be measured by inhibition of an agonist-induced foot tapping in a gerbil, as descibed in Science, 281, 1640–1695 (1998), which is herein incorporated by reference in its entirety. It will be recognized that compounds having the formula (I) can exhibit $NK_1$ antagonist activities of varying degrees. For instance, certain compounds can exhibit stronger $NK_1$ antagonist activities than others.

The compounds of the invention exhibit potent affinities for the $NK_1$ receptor as measured by Ki values (in nM). The activities (potencies) for the compounds of the invention are determined by measuring their Ki values. The smaller the Ki value, the more active is a compound for antagonizing the $NK_1$ receptor. Compounds of the invention exhibit a wide range of activities. The $NK_1$ average Ki values for compounds having the formula (I) generally range from >0 nM to about 1000 nM, preferably, from about 0.05 nM to about 500 nM, with values of from about 0.05 nM to about 100 nM being more preferred. $NK_1$ average Ki values of from >0 nM to about 25 nM are even more preferred. Yet even more preferred, are compounds having average Ki values of from >0 nM to about 10 nM for the $NK_1$ receptor. Still even more preferred, are compounds having average Ki values of from >0 nM to about 5 nM for the $NK_1$ receptor. The most preferred compounds have $NK_1$ average Ki values of from >0 nM to about 3 nM.

The inventive compounds are also highly selective for antagonizing a $NK_1$ receptor as opposed to antagonizing (i) $NK_2$ and/or (ii) $NK_3$ receptors. When a compound's selection ratio is greater than about 100 for the Ki of the $NK_1$ receptor to the Ki of the $NK_2$ receptor, and/or, independently, the Ki of the $NK_3$ receptor, then the compound is defined herein as a selective antagonist of the $NK_1$ receptor, as opposed to the $NK_2$ and/or $NK_3$ receptors, respectively.

Compounds having the formula (I) may have at least one asymmetrical carbon atom. All isomers, including stereoisomers, diastereomers, enantiomers, regiostereomers, tautomers and rotational isomers, are contemplated as being part of the invention. Prodrugs, salts, solvates, esters, etc., derived from the compounds having the formula (I) or precursors thereof are also within the scope of the invention. The invention includes d- and l-isomers in pure form and in admixture, including racemic mixtures. Isomers can be prepared using conventional techniques, either by reacting optically pure or optically enriched starting materials or by separating isomers of a compound having the formula (I). Those skilled in the art will appreciate that for some compounds having the formula (I), particular isomers can show greater pharmacological activity than other isomers.

There are many uses for the compounds having the formula (I). For instance, compounds having the formula (I) can be useful as antagonists of neurokinin receptors, particularly, $NK_1$ receptors in a mammal, such as a human. As such, they may be useful in treating and preventing one or more of a variety of mammalian (human and animal) disease states (physiolgical disorders, symptoms and diseases), for instance, respiratory diseases (e.g., chronic lung disease, bronchitis, pneumonia, asthma, allergy, cough and bronchospasm, especially, asthma and cough), inflammatory diseases (e.g., arthritis and psoriasis), skin disorders (e.g., atopic dermatitis and contact dermatitis), ophthalmological disorders (e.g., retinitis, ocular hypertension and cataracts), central nervous system conditions, such as depressions (e.g., neurotic depression), anxieties (e.g., general anxiety, social anxiety and panic anxiety disorders), phobias (e.g., social phobia), and bipolar disorder, addictions (e.g., alcohol dependence and psychoactive substance abuse), epilepsy, nociception, psychosis, schizophrenia, Alzheimer's disease, AIDs related dementia, Towne's disease, stress related disorders (e.g., post tramautic stress disorder), obsessive/compulsive disorders, eating disorders (e.g., bulemia, anorexia nervosa and binge eating), mania, premenstrual syndrome, gastrointestinal disorders (e.g., irritable bowel syndrome, Crohn's disease and colitis), atherosclerosis, fibrosing disorders (e.g., pulmonary fibrosis), obesity, Type II diabetes, pain related disorders (e.g., headaches, such as migraines, neuropathic pain, postoperative pain, and chronic pain syndromes), bladder and genitourinary disorders (e.g., interstitial cystitis, urinary incontinence, pollakiuria and micturation disorders), emesis and nausea. In particular, the compounds having the formula (I) are useful for treating disease states related to microvascular leakage and mucus secretion. Consequently, the compounds of the invention are especially useful in the treatment and prevention of asthma, emesis, nausea, depressions, anxieties, cough and pain related disorders (e.g., migraine), more preferably, for emesis, nausea, depression, anxiety and cough.

In another aspect, the invention relates to pharmaceutical compositions comprising at least one compound represented by the formula (I) in a pharmaceutically-acceptable carrier. The invention also relates to the use of such pharmaceutical compositions in the treatment of mammalian disease states, such as those listed above.

In still another aspect of the invention, a method is provided for antagonizing an effect of a Substance P at a neurokinin-1 receptor site or for the blockade of one or more neurokinin-1 receptors in a mammal in need of such treatment, comprising administering to the mammal an effective amount of at least one compound having the formula (I).

In another embodiment of the invention, an effective amount of one or more of the inventive $NK_1$ receptor antagonists may be combined with an effective amount of one or more selective serotonin reuptake inhibitors ("SSRIs") to treat depression or anxiety. SSRIs alter the synaptic availability of serotonin through their inhibition of presynaptic reaccumulation of neuronally released serotonin. U.S. Pat. No. 6,162,805, which is incorporated herein by reference in its entirety, discloses a method for treating obesity with a combination therapy of a $NK_1$ receptor antagonist and an SSRI. An inventive compound(s) having the formula (I) can be combined together with an SSRI (s) in a single pharmaceutical composition or it can be administered simultaneously, concurrently or sequentially with an SSRI.

Numerous chemical substances are known to alter the synaptic availability of serotonin through their inhibition of presynaptic reaccumulation of neuronally released serotonin. Representative SSRIs include, without limitation, the following: fluoxetine, fluvoxamine, paroxetine, sertaline, and pharmaceutically-acceptable salts thereof. Other compounds can readily be evaluated to determine their ability to selectively inhibit serotonin reuptake. Thus, the invention relates to a pharmaceutical composition comprising at least one $NK_1$ receptor antagonist having the formula (I) and at least one SSRI, and a method of treating the above identified mammalian disease states, the method comprising administering to a patient in need of such treatment an effective amount of the pharmaceutical composition comprising at least one $NK_1$ receptor antagonist having the formula (I) in combination with at least one SSRI, such as one of those recited above.

In another aspect, the invention relates to a method of treating emesis, comprising administering to a patient in need of such treatment an effective amount of at least one $NK_1$ receptor antagonist having the formula (I). Compounds of the present invention are particularly useful in treating delayed onset emesis such as that experienced 24 hours to several days after the administration of chemotherapy. See Gonzales et al, *Oncology Special Edition, Vol. 5* (2002), p. 53–58. Combinations of at least one $NK_1$ receptor antagonist and at least one other anti-emetic agent such as a serotonin 5-$HT_3$ receptor antagonist can be used to treat other forms of emesis, e.g., acute emesis induced by chemotherapy, radiation, motion and alcohol (e.g., ethanol), and post-operative nausea and vomiting. Examples of serotonin 5-$HT_3$ receptor antagonists are palonsetron, ondansetron and granisetron, or a pharmaceutically-acceptable salts thereof.

When an inventive $NK_1$ receptor antagonist is combined with an SSRI or serotonin 5-$HT_3$ receptor antagonist for administration to a patient in need of such treatment, the two or more active ingredients can be administered simultaneously, consecutively (one after the other within a relatively short period of time), or sequentially (first one and then the other over a period of time).

Thus, the compounds of the invention may be employed alone or in combination with other agents. In addition to the above described $NK_1$ receptor antagonist/SSRI or serotonin 5-$HT_3$ receptor antagonist combination therapy, the compounds having the formula (I) may be combined with other active agents, such as other types of $NK_1$ receptor antagonists, prostanoids, $H_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, $ET_A$ antagonists, renin inhibitors, serotonin 5-$HT_{2c}$, receptor agonists, nociceptin receptor agonists, rho kinase inhibitors, potassium channel modulators and/or inhibitors of multi-drug resistance protein 5. Preferable therapeutic agents for combination therapy with compounds of the invention are the following: prostanoids, such as prostaglandin $E_1$; α-adrenergic agonists, such as phentolamine mesylate; dopamine receptor agonists, such as apomorphine; angiotensin II antagonists, such as losartan, irbesartan, valsartan and candesartan; and $ET_A$ antagonists, such as bosentan and ABT-627.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparations subdivided into suitably sized unit doses containing appropriate quantities of the active component, e.g., an effective amount to achieve the desired purpose.

The quantity of active compound in a unit dose of preparation may be varied or adjusted from about 0.01 mg to about 4,000 mg, preferably from about 0.02 mg to about 1000 mg, more preferably from about 0.03 mg to about 500 mg, and most preferably from about 0.04 mg to about 250 mg according to the particular application.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.02 mg/day to about 2000 mg/day, in two to four divided doses.

The quantity of $NK_1$ receptor antagonist in combination with a SSRI or serotonin 5-$HT_3$ receptor antagonist (5-$HT_3$) in a unit dose of preparation may be varied or adjusted from about 10 to about 300 mg of $NK_1$ receptor antagonist combined with from about 10 to about 100 mg of SSRI or 5-$HT_3$. A further quantity of $NK_1$ receptor antagonist in combination with a SSRI or 5-$HT_3$ in a unit dose of preparation may be varied or adjusted from about 50 to about 300 mg of $NK_1$ receptor antagonist combined with from about 10 to about 100 mg of SSRI or 5-$HT_3$. An even further quantity of $NK_1$ receptor antagonist in combination with SSRI or 5-$HT_3$ in a unit dose of preparation may be varied or adjusted from about 50 to about 300 mg of $NK_1$ receptor antagonist combined with from about 20 to about 50 mg of SSRI or 5-$HT_3$, depending on the particular application.

Upon improvement of a patient's condition, a maintenance dose of a compound, composition or combination of the invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

The inventive compounds can exist in unsolvated as well as solvated forms, including hydrated forms. In general, the solvated forms, with pharmaceutically-acceptable solvents, such as water, ethanol, and the like, are equivalent to the unsolvated forms for purposes of this invention.

The inventive compounds may form pharmaceutically-acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in a conventional manner. The free base forms may be regenerated by treating the salt with a suitable dilute aqueous base solution, such as dilute aqueous sodium hydroxide, potassium carbonate, ammonia or sodium bicarbonate. The free base forms may differ somewhat from their respective salt forms in certain physical properties, such as solubility in polar solvents, but the salts are otherwise equivalent to their respective free base forms for purposes of the invention.

Acidic compounds of the invention (e.g., those compounds which possess a carboxyl group) form pharmaceutically-acceptable salts with inorganic and organic bases. Representative examples of such types of salts are sodium, potassium, calcium, aluminum, gold and silver salts. Also included are salts formed with pharmaceutically-acceptable amines, such as ammonia, alkyl amines, hydroxyalkylamines, N-methylglucamine, and the like.

Another aspect of the invention is to provide a kit comprising separate containers in a single package, wherein the inventive pharmaceutical compounds, compositions and/or salts thereof are used in combination with pharmaceutically-acceptable carriers to treat a variety of physiological disorders, symptoms and diseases.

Definitions for Abbreviations

Following are general and specific methods of preparing compounds having the formula (I). As used herein, the following abbreviations are defined as follows:

RBF is a round bottom flask;

RT is room temperature;

Me is methyl;

Bu is butyl;

MeOH is methanol;

Ac is acetyl;

Et is ethyl;

Ph is phenyl;

MS is methanesulfonyl;

THF is tetrahydrofuran;

OAc is acetate;

$(Boc)_2O$ is di-tert-butyl dicarbonate;

(Boc) is tert-butoxy carbonyl;

TLC is thin layer chromatography;

LAH is lithium aluminum hydride;

LDA is lithium diisopropyl amine;

CDI is 1,1-carbonyl diimidazole;

HOBT is hydroxybenzotriazole;

DEC is 1[3-(dimethylamino)propyl]-3-ethylcarbodiimide hydrochloride;

TFA is trifluoroacetic acid;

MTBE is t-butyl methyl ether;

DAST is diethylaminosulfur trifluoride;
DIEA or i-Pr$_2$EtN is diisopropylethyl amine;
UNCA is urea protected N-carboxy anhydride;
Prep plate is preparative thin layer chromatography;
DMF is dimethyl formamide
TEMPO is a free radical of 2,2,6,6-tetra methyl-1-piperidinyloxy;
BuLi is butyl lithium;
KHMDS is potassium bis(trimethylo silyl)amide;
DBU is 1,8-diazabicyclo[5.4.0]un dec-7-ene; and
AlMe$_3$ is trimethyl aluminum.

Compounds having the formula (I) can be prepared using methods known to those skilled in the art. Typical procedures are described below, although a skilled artisan will recognize that other procedures may be applicable, and that the procedure may be suitably modified to prepare other compounds within the scope of formula (I).

General Methods of Preparation

Compounds having the formula (I) may be generally prepared from the corresponding amino acid derivative A1 as shown under the following conditions, where, X$^2$ is —C—; Y is O, S or NR$^{11}$; n$_2$ is 1; and Ar$^1$, Ar$^2$, X$^1$, and R$^1$ through R$^{31}$, are each defield in the summary of the invention.

Standard protection of the amino acid as a carbamate derivative is followed by activation of the carboxylic acid. For n$_2$=1, treatment with phosgene or a phosgene equivalent, preferably, triphosgene, is one such method for acid activation. Those skilled in the art will recognized that other methods, such as preparation of the Weinwreb amide, may function in a similar manner to activate the acid toward nucleophilic addition. Deprotonation of a suitable enolizable position, preferably, but not limited, to R$^4$-substituted acetates and malonates, with a suitable base, followed by mixing with N-carboxyanhydride A2, provides for the keto ester A3. Deprotection using standard procedures provides the amino ester derivative, which is then cyclized spontaneously or by heating in a suitible solvent, such as THF or dichloroethane, to the ketolactam A4. This derivative can be reduced by standard reagents, such as lithium borohydride or lithium aluminum hydride, to give the hydroxy lactam A5. Conversion of the hydroxyl group to a suitable leaving group, preferably, the mesylate or tosylate, allows for elimination to the unsaturated lactam A6. This material can be reduced via hydrogen to provide the substituted lactam A7.

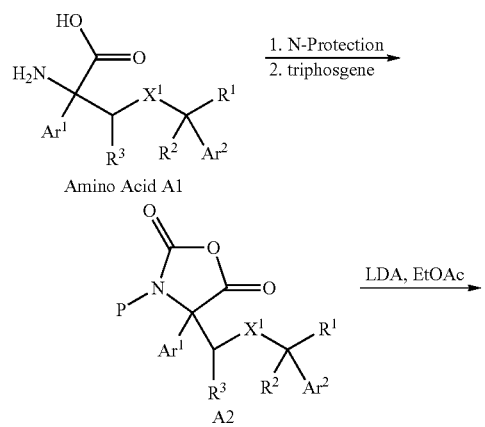

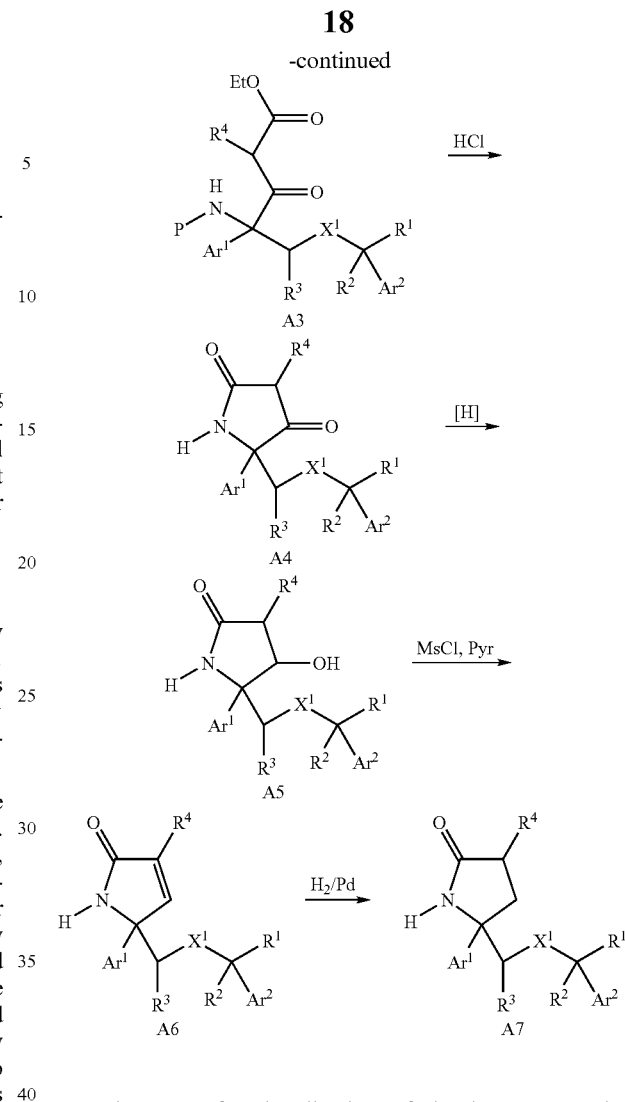

Furthermore, functionalization of the lactam may be accomplished through standard chemistry. Thus, protection of the lactam is accomplished by conversion to a carbamate, preferably, Boc, by treatment with the corresponding anhydride or chloroformate derivative. The resulting protected lactam can be deprotonated with a suitable base, such as LDA or KHMDS, and then treated with an electrophile to provide the functionalized lactam. Appropriate electrophiles can be, but are not limited to, alkyl halides, trisyl azide, oxygen and disulphides. Those skilled in the art can conventionally further functionalize these derivatives to prepare compounds, where, R$^4$ and R$^5$ are each independently selected from —(CH$_2$)$_{n1}$-G and —C(O)(CH$_2$)$_{n4}$-G, where n$_1$ is 0 to 5; n$_4$ is 1 to 5; and G is defined in the summary of the invention.

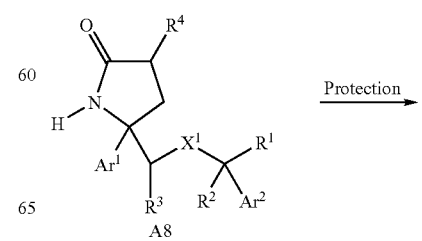

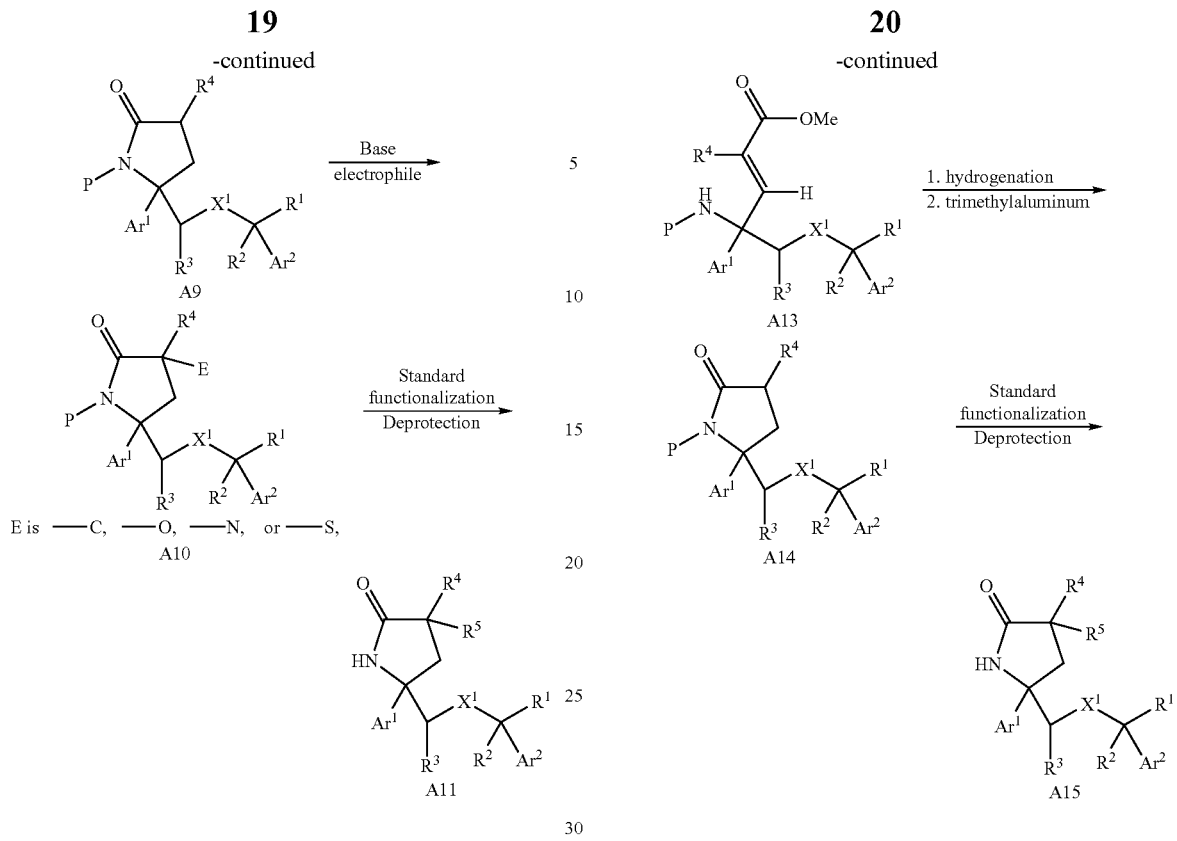

Alternatively, the amino acid A1 can be converted to a protected amino aldehyde A12. This aldehyde can be treated with a nucleophile [e.g., an enolate or Wittig reagent] to give the correspsonding hydroxyl addition or olefin product. Elimination of aldol products to provide the olefin product may be done via activation (preferably, via the tosylate or mesylate) and heating in the presence of a suitable base to give the olefin A13. Hydrogenation of the olefin A13, followed by functionalization provides the lactam A14, where $n_2$ is 1:

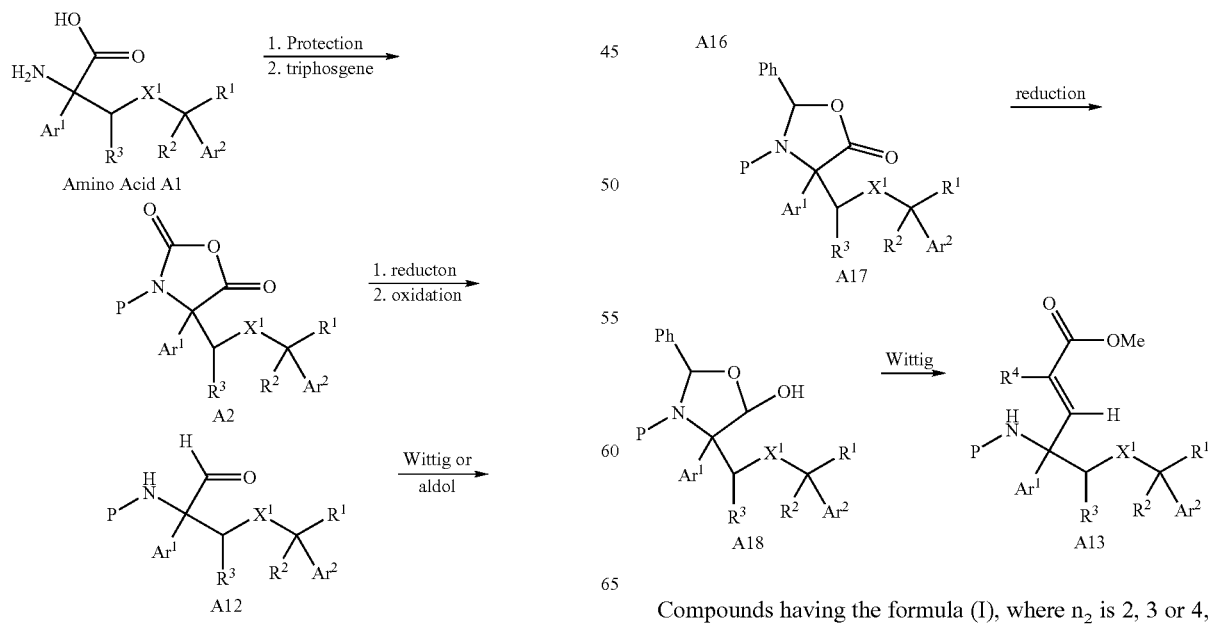

An alternate method of preparing A13 involves the stereoselective alkylation of a protected oxazolidinone A16. Partial reduction with a reducing agent, such as lithium aluminum hydride, provides the lactol A18. A Wittig reaction provides the corresponding olefin A13:

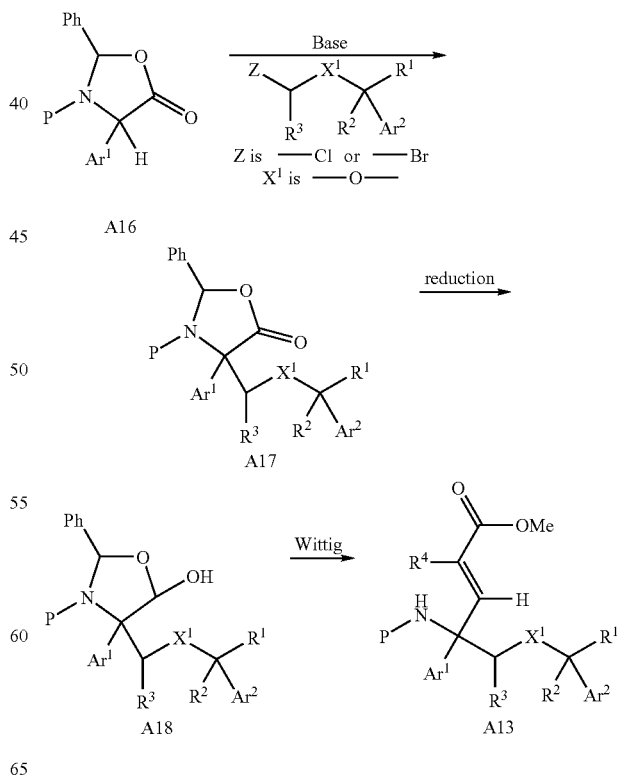

Compounds having the formula (I), where $n_2$ is 2, 3 or 4, may be prepared by conversion of the amino acid A1 to 1, 2 and 3 carbon homologated derivatives using routine chemistry known to those skilled in the art. Particularly useful reagents for this carbon chain homologation include: Wittig chemistry using methoxymethyl triphenylphosphonium bromide or an analogous reagent, cyanomethyl triphenylphosphonium bromide and Horner-Emmons protocols. Functionalizations and cyclizations to the 6-, 7- and 8-membered lactams, respectively, are analogous to the procedures described above.

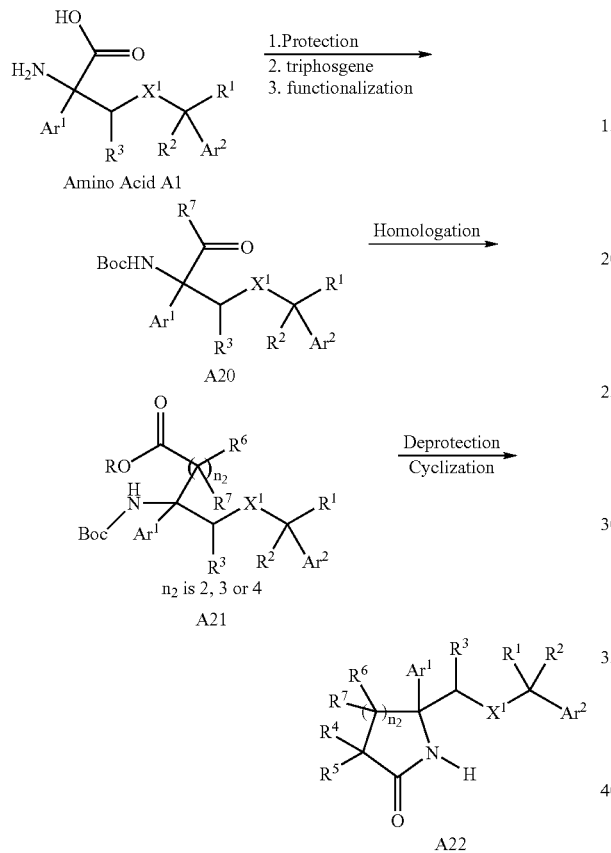

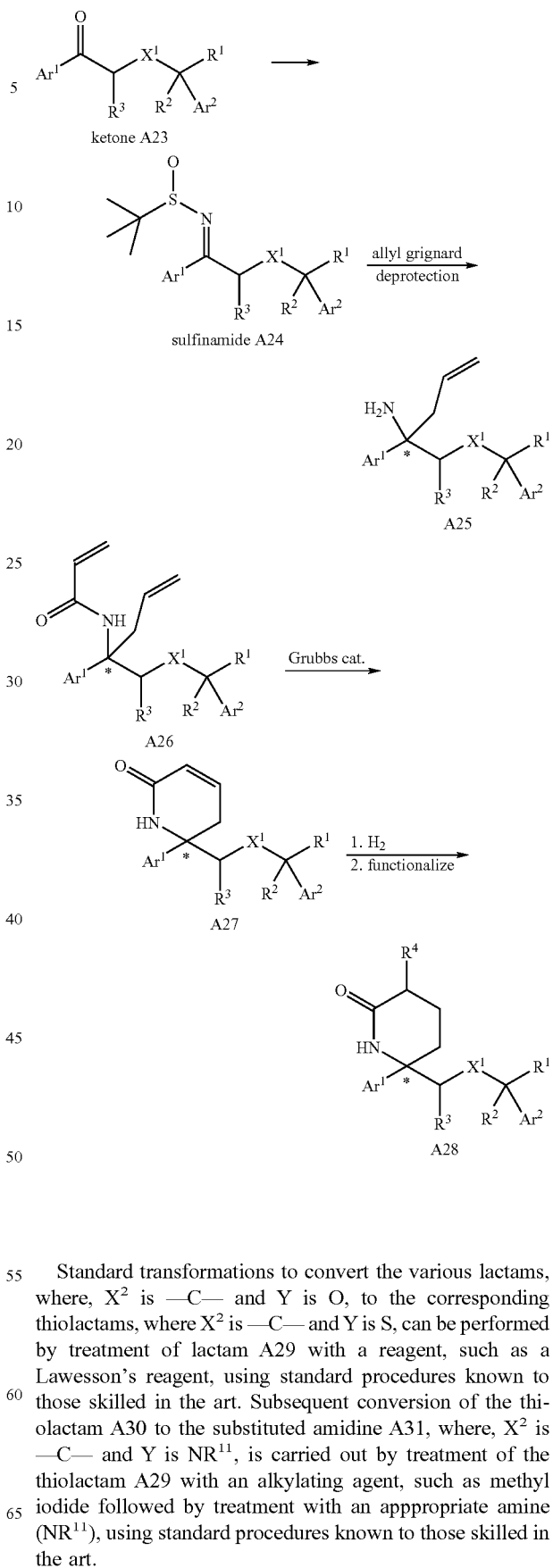

Alternatively, compounds having the formula (I), where $n_2$ is 2, 3 or 4 and $X^1$ is —O—, can be prepared by means of transformation of ketone A23 to the sulfinamide using the appropriate sulfinamide (racemic or non-racemic) and titaniumisopropoxide, according to the protocol described in Cogan, D. A.; Liu, G.; and Ellman, J.; Tetrahedron, 55, 8883 (1999). The sulfinamide A24 is then treated with a suitable allyl grignard, followed by deprotection of the nitrogen with an acid, preferably, HCl. The resulting amine is coupled with a suitable olefinic carboxylic acid derivative using common protocols, preferably, treatment with an acid chloride and base. Treatment of the bis olefin A26 with Grubb's catalyst using standard olefin metathesis conditions provide the unsaturated lactam A27. Hydrogenation to the saturated lactam results in the unsubstituted delta lactam. Protection of the lactam nitrogen as previously described, where $n_2$ is 1 and functionalization is adjacent to the nitrogen, is performed in a similar manner. Those skilled in the art will appreciate that acylation of amine A25 with an appropriate carboxylic acid of 4 to 5 carbon atoms in length containing a terminal olefin, followed by subsequent synthetic operations as described above will result in the cyclic lactams, where $n_2$ is 3 or 4.

Standard transformations to convert the various lactams, where, $X^2$ is —C— and Y is O, to the corresponding thiolactams, where $X^2$ is —C— and Y is S, can be performed by treatment of lactam A29 with a reagent, such as a Lawesson's reagent, using standard procedures known to those skilled in the art. Subsequent conversion of the thiolactam A30 to the substituted amidine A31, where, $X^2$ is —C— and Y is $NR^{11}$, is carried out by treatment of the thiolactam A29 with an alkylating agent, such as methyl iodide followed by treatment with an apppropriate amine ($NR^{11}$), using standard procedures known to those skilled in the art.

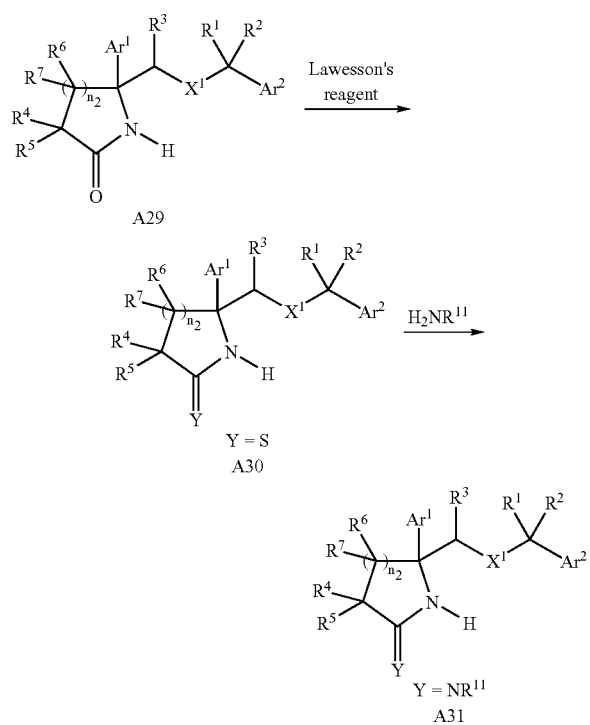

Functionalization of the lactam nitrogen may be performed at an appropriate point in the synthesis by deprotonation with a suitable base and reaction of the necessary electrophile to provide the substitutents defined for $R^{18}$. Those skilled in the art will appreciate that a substituted alkyl halide will afford the corresponding substituted $C_1-C_6$ alkyl group and treatment with tetrabenzypyrophosphate, followed by hydrogenation will serve to provide for $R^{18}=$—$P(O)(OH)_2$.

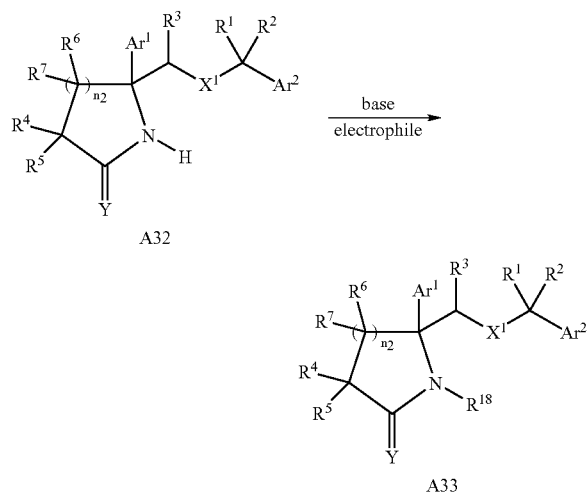

For compounds having the formula (I), where $X^2$ is —S— or —S(O)—, the amino acid A34 can be reduced with a suitable reagent, such as LAH, $BH_3$ or $TMSCI/LiBH_4$, using the protocols known to those skilled in the art to provide the corresponding amino alcohol A35. This material is then treated with an excess of the appropriately substituted sulfonylhalide to give the cyclic sulfonamide A36 ($X^2$ is —S(O)— and Y is O). Photochemical rearrangement of the sulfonamide to N-hydroxy sulfinamide, followed by N—O cleavage may provide the corresponding sulfinamide A37 ($X^2$ is —S— and Y is O).

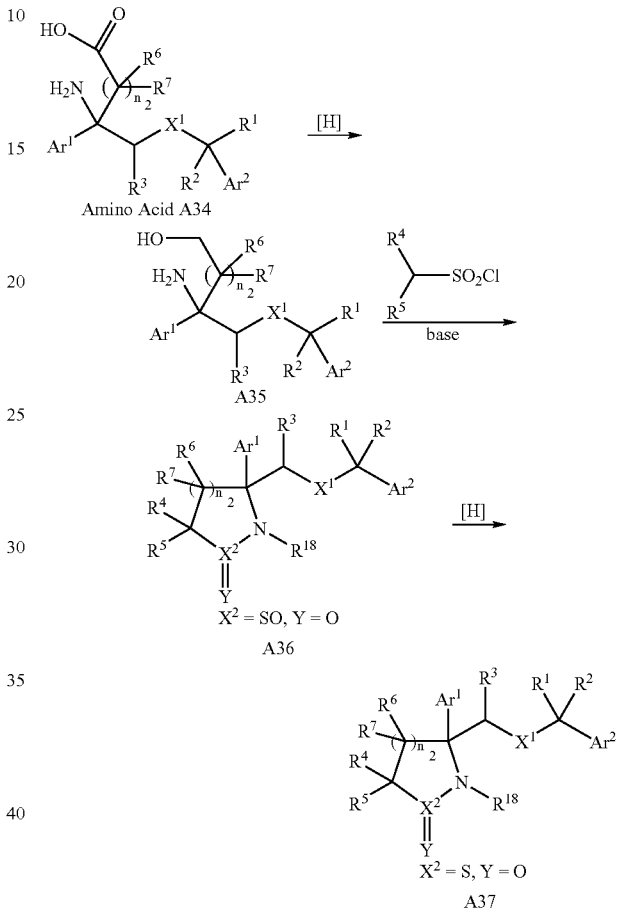

Those skilled in the art will recognize that certain additional protection and deprotection steps may needed in order to accommodate different functional groups. Accordingly, the order of synthetic operations may be different in order to maintain functional group compatibility with the operational steps in the synthesis.

Preparation of amino acid derivative A1 can be achieved in a variety of ways in both racemic and optically pure forms, as described below as well as by various methods known to those skilled in the art. Ketone A38 is transformed into the corresponding hydantoin A39 by heating with KCN/ammonium carbonate in ethanol/water mixtures or by using alternate standard conditions known to those skilled in the art. Hydrolysis of the resulting hydantoin A39 by heating with barium hydroxide using standard protocols provides the amino acid A1. Alternate methods of preparing the hydantoin may be employed and include utilizing a Strecker reaction or equivalent in either racemic or optically enhanced forms, followed by cyclization to the hydantoin.

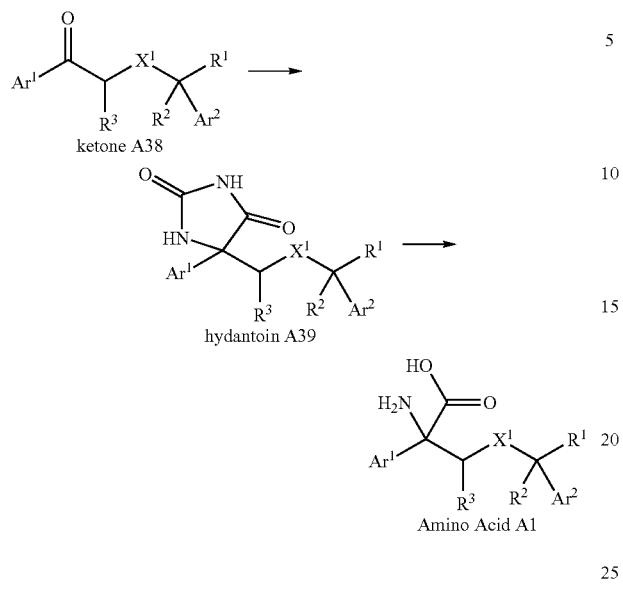

ketone A38 hydantoin A39

Amino Acid A1

The ketone A38 may be prepared using several different methods employing commercially available materials. Ketone A41 can be subjected to acylation ($Q^1$ is —NH$_2$, —OH or —SH), reductive amination ($Q^1$ is —NH$_2$), ether formation ($Q^1$ is —OH) by standard alkylation methods, thio ether formation ($Q^1$ is —SH) by standard alkylation methods, or esterification ($Q^1$ is —OH or —SH). Alternatively, the corresponding alcohol A43 can be oxidized to an aldehyde and treated with an aryl or heteroaryl organometallic reagent, followed by oxidation to give ketone A38.

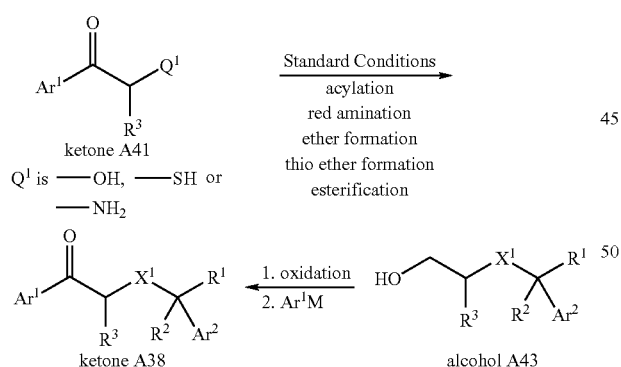

ketone A41
$Q^1$ is —OH, —SH or —NH$_2$ ketone A38 alcohol A43

Another method for preparing ketone A38 involves nucleophilic displacement of a leaving group, such as —Cl, —Br, —I, —OMs and —OTf, adjacent to the aryl or heteroaryl ketone, for example, see WO 01/44200 (2001), which is incorporated herein in its entirety by reference. Accordingly, a suitable substituted styrene or heteroaryl epoxide may be opened with the appropriate nucleophile to give the desired $X^1$:

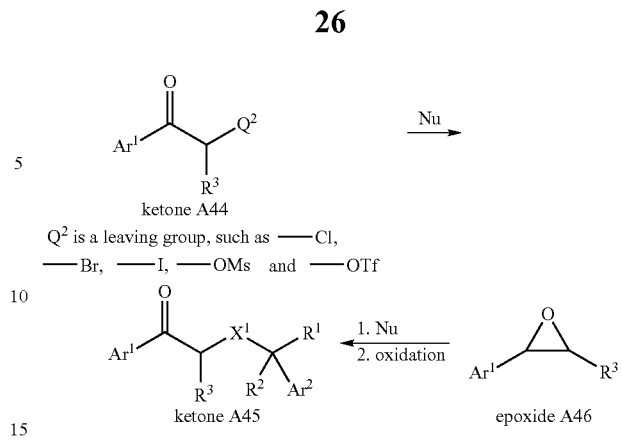

ketone A44

$Q^2$ is a leaving group, such as —Cl, —Br, —I, —OMs and —OTf ketone A45 epoxide A46

Another method for preparing amino acid A1 involves the employment of a synthetic route described in WO 01/44200:

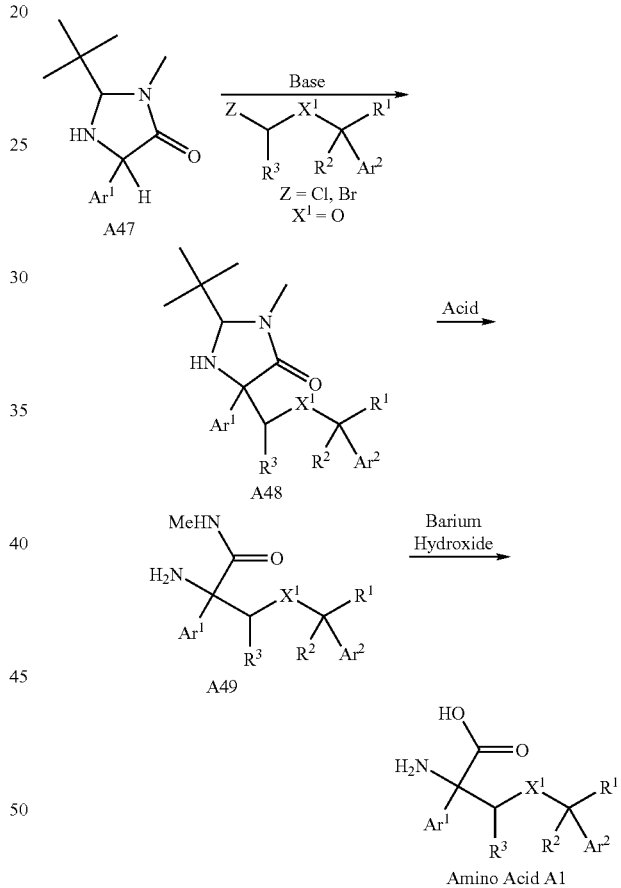

A47
Z = Cl, Br
$X^1$ = O

A48

A49

Amino Acid A1

In addition to the schemes depicted above, several reviews on the preparation of disubstituted amino acids similar to amino acid A1 describe similar and alternative methods which may be adapted to prepare amino acid A1. See e.g., Carlos Cativiela and Maria Dolores Diaz-de-Villegas, *Tetrahedron: Asymmetry*, 9, *Stereoselective synthesis of quaternary a-amino acids. Part I: Acyclic compounds*, 3517–3599 (1998); and Dieter Seebach, René Imwinkelried and Theodor Weber, *Modern Synthetic Methods*, 4, *EPC Syntheses with C, C Bond Formation via Acetals and Enamines*, 125 et al., (1986), each of which is incorporated herein in its entirety by reference.

SPECIFIC METHODS OF PREPARATION—EXAMPLES

Compound 1 was prepared using a procedure analogous to that described in WO 01/44200 (2001) for compound 96.

Example 1

Step 1:

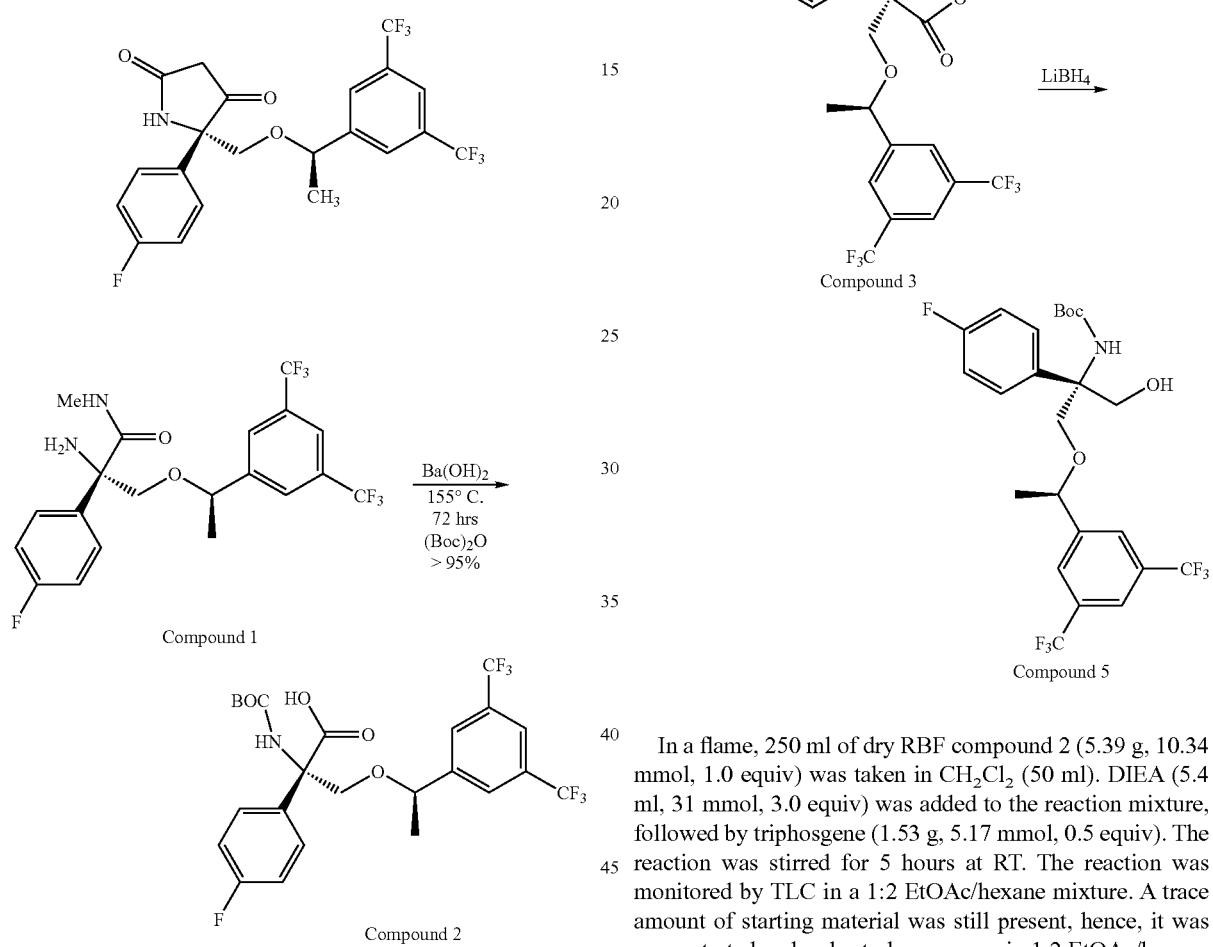

In a steel autoclave with a stirring bar, amino amide compound 1 (10.0 g, 23.0 mmol, 1.0 equiv) was added, followed by Ba(OH)$_2$ (31.33 g, 115 mmol, 5.0 equiv) and (70 ml) H$_2$O. The reaction was heated to 155° C. for 72 hours and then cooled to RT. The reaction mixture was transferred into a 1L 3-neck RBF equipped flask containing a mechanical stirrer. 80 ml of THF was followed by 80 ml of saturated NaHCO$_3$ and (Boc)$_2$O (15 g, 69 mmol, 3.0 equiv). The reaction was stirred at RT overnight. The reaction was monitored by TLC in 20% MeOH/EtOAc. Trace amounts of starting material were still present, hence, an additional 4 g of (Boc)$_2$O was added. After six hours, the reaction was completed. The white suspension was filtered, then washed with EtOAc (500 ml). Aqueous layers 3×200 ml EtOAc were extracted. The organic layers were combined, rinsed with brine, and dried over Na$_2$SO$_4$ (concentrated) to give compound 2 (11.5 g, 96%).

Step 2:

In a flame, 250 ml of dry RBF compound 2 (5.39 g, 10.34 mmol, 1.0 equiv) was taken in CH$_2$Cl$_2$ (50 ml). DIEA (5.4 ml, 31 mmol, 3.0 equiv) was added to the reaction mixture, followed by triphosgene (1.53 g, 5.17 mmol, 0.5 equiv). The reaction was stirred for 5 hours at RT. The reaction was monitored by TLC in a 1:2 EtOAc/hexane mixture. A trace amount of starting material was still present, hence, it was concentrated and a short plug was run in 1:2 EtOAc/hexane and 2% Et$_3$N to give compound 3 (5.33 g, 94%). UNCA compound 3 was then taken up in dry THF (57 ml). LiBH$_4$ (0.425 g, 19.49 mmol, 2.0 equiv) was added and the reaction mixture was stirred over night at RT. The reaction was monitored by TLC in 1:2 EtOAc/hexane. The reaction went to completion, as it was cooled to 0° C. in an ice bath and then quenched with saturated NaHCO$_3$ (10 ml). The reaction mixture was taken up in EtOAc, washed with saturated NaHCO$_3$ (2×100 ml), and dried over Na$_2$SO$_4$ to concentrate it. A short plug was run in 1:2 EtOAc/hexane to give compound 5 (4.5 g, 85%).

Electrospray MS [M+1]$^+$ 508.1.

Step 3:

-continued

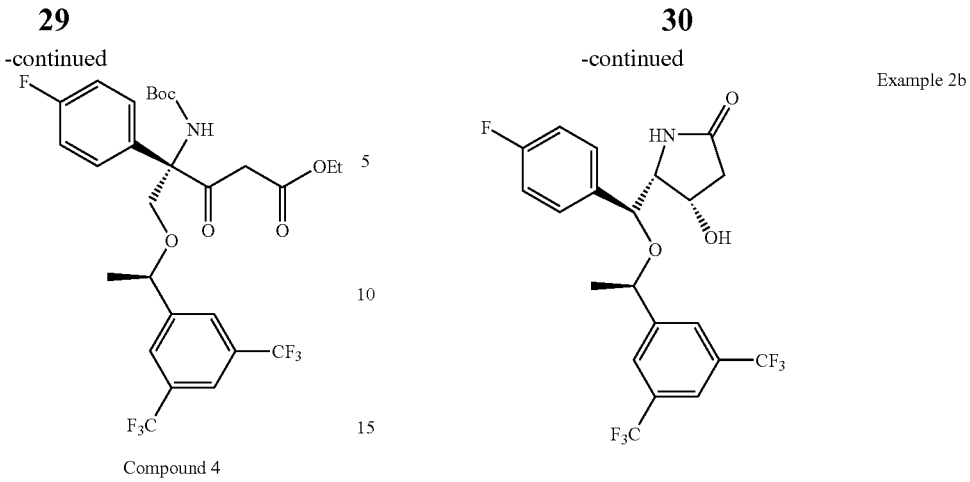

Compound 4

In a 2-neck (50 ml) flame dry flask, anhydrous EtOAc (172 μl, 1.77 mmol, 1.0 equiv) was taken in THF (dry). The solution was cooled to −78° C. under $N_2$. 2.0M of LDA (1.77 ml, 3.54 mmol, 2.0 equiv) was then added drop wise, and the reaction mixture was stirred at −78° C. for an hour. The reaction mixture turned pale yellow in color. A solution of UNCA compound 3 (1.0 g, 1.77 mmol, 1.0 equiv) in THF was added drop wise to the reaction mixture. The reaction mixture was stirred at −78° C. for an hour, monitored by TLC 4/1 hexane/EtOAc and 2%$Et_3N$, quenched using acetic acid (203 μl, 3.54 mmol, 2.0 equiv), and warmed to RT. The reaction was diluted with EtOAc, washed with saturated $NaHCO_3$, and dried over $Na_2SO_4$ to give a pale yellow oil as compound 4 (0.95 g, 88%).

Electrospray MS $[M+1]^+$ 610.1.

Step 4:

In a 100 ml flask, compound 4 (1.05 g, 1.73 mmol, 1.0 equiv) was taken in $CH_2Cl_2$ (30 ml) and cooled to 0° C. 4M HCl in dioxane (4.3 ml, 17.2 mmol, 10.0 equiv) was added to the reaction mixture drop wise. The reaction mixture was stirred for 4 hours and monitored by TLC hexane/EtOAc and 2%$Et_3N$. When the reaction was completed, it was quenched with saturated $NaHCO_3$, and dried over $Na_2SO_4$ to give a crude product. The crude product was taken up in dichloroethane (25 ml), heated for 3 hours at 52° C. and monitored by TLC 3/2 hexane/EtOAc. When the reaction was completed, the reaction mixture was concentrated to give Example 1 (0.90 g, 113%).

Electrospray MS $[M+1]^+$ 464.1.

Examples 2a and 2b

Example 2a

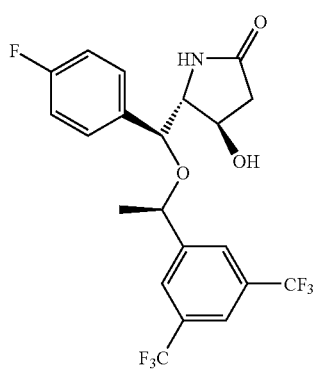

Example 2b

In a flame dried one-neck, 15 ml RBF, Example 1 (0.050 g, 0.11 mmol, 1.0 equiv) was taken up in 3 ml of EtOH, followed by $NaBH_4$ (0.005 g, 0.11 mmol, 1.0 equiv). The reaction mixture was stirred at RT for 3 hours. The reaction was monitored by TLC in 1:1 EtOAc/hexane. Trace amounts of starting material were still present, hence, the reaction mixture was taken up in $CH_2Cl_2$, quenched with $H_2O$ (1 ml), and washed with 6 N HCl (5 ml), followed by saturated $NaHCO_3$ (5 ml). All organic layers were combined and dried over $Na_2SO_4$, and concentrated. Purification was carried out using Prep plate in 85:15 EtOAc/hexane to give Example 2b as a minor isomer (0.012 g) and Example 2a as a major isomer (0.018 g). Total yield for each isomer was (59%).

Electrospray MS $[M+1]^+$ 466.1 for both isomers.

NMR for Example 2a: $^1H$ NMR: ($CDCl_3$, 400 MHz): δ 7.8(s), 7.1(t), 4.6(q), 4.4(br q), 3.9(d), 3.6(d), 2.9(dd), 2.6 (dd), 1.4(d).

NMR for Example 2b: $^1H$ NMR: ($CDCl_3$, 400 MHz): δ 7.8(s), 7.1(t), 4.5(q), 4.3(br q), 3.8(d), 3.5(d), 2.8(dd), 2.3 (dd), 1.4(d).

Example 3

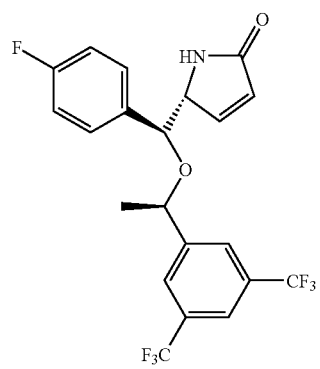

In a 250 ml RBF, a mixture of Example 2a and Example 2b (0.742 g, 1.6 mmol, 1.0 equiv) was taken in 30 ml $CH_2Cl_2$, and cooled to 0° C. in an ice bath. $Et_3N$ (580 μL, 4.0 mmol, 2.5 equiv) and MsCl (161 μL, 2.08 mmol, 1.3 equiv) were added to the reaction mixture. The reaction mixture was stirred at 0° C. for 3.5 hours. The reaction was monitored by TLC in 4:1 EtOAc/hexane. The reaction went to completion, hence, the product was concentrated. To this product, pyridine (25 ml) was added, and the reaction was refluxed at 90° C. for 72 hours. The reaction mixture turned dark brown in color upon heating at 90° C. The reaction was monitored by TLC in 4:1 EtOAc/hexane. The reaction went to completion, hence, the product was taken up in EtOAc (25 ml), and washed with pyridine and 5% HCl/Aq. (50 ml), followed by 2×25 ml of saturated NaHCO₃, then dried over Na₂SO₄ until concentrated. Purification was carried out using a Biotage (40M) column, 3:2 EtOAc/hexane to give Example 3 (0.410 g, 57% over two steps).

Electrospray MS [M+1]⁺ 448.1.

Example 4

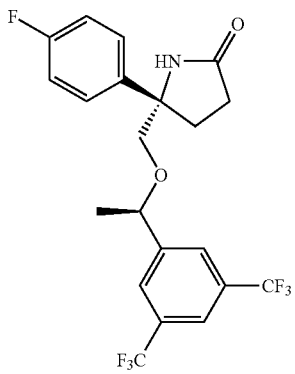

In a 250 ml RBF, Example 3 (0.370 g, 0.83 mmol, 1.0 equiv) was taken in (30 ml) absolute EtOH. The reaction mixture was degassed and flushed with N₂ for several times. 10% Pd/Carbon (0.06 g, 0.1 equiv) was then added and the reaction mixture was again degassed and flushed with H₂ for several times. The reaction mixture was stirred over night. The reaction was monitored by TLC in 3:2 EtOAc/hexane. The reaction went to completion, hence, the product was filtered through a celite plug rinsed with EtOH, and then concentrated. Purification was carried out using a silica plug in 3:2 EtOAc/hexane to give Example 4 (0.340 g, 91%).

Electrospray MS [M+1]⁺ 450.1.

Examples 5 and 7

Example 5

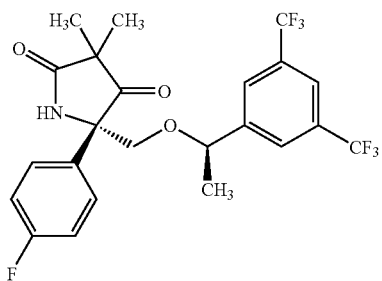

Example 7

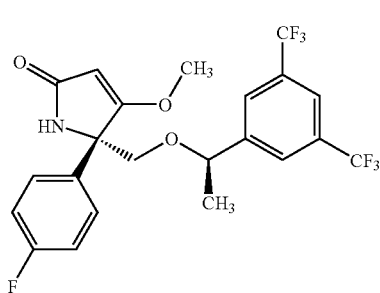

In a flame dry, 25 ml RBF, Example 1 (0.138 g, 0.298 mmol, 1.0 equiv) was taken up in DMF (5 ml). K₂CO₃ (0.082 g, 0.596 mmol, 2.0 equiv) was added to the reaction mixture, followed by CH₃I (38 μL, 0.61 mmol, 2.05 equiv), and the reaction mixture was stirred for 30 hours at RT. The reaction was monitored by TLC in 3:2 EtOAc/hexane. The reaction went to completion, but a spot lower in $R_f$ than what the product should give appeared. The lower spot could be a mono-methylation, hence, the reaction mixture was stirred for another 14 hours. The reaction was monitored by TLC in 3:2 EtOAc/hexane, and the lower spot was still present, hence, the reaction mixture was taken up in EtOAc (25 ml), washed with H₂O (3×15 ml), followed by (2×15 ml) of saturated NaHCO₃, and dried over Na₂SO₄ until concentrated. Purification was carried out using Biotage (20M) column 4:1 hexane/EtOAc to give Example 5 in a white, crystalline solid form (0.052 g, 40%).

Electrospray MS [M+1]⁺ 492.1.

The lower spot in $R_f$ was isolated to give Example 7 (0.02 g, 15%).

Electrospray MS [M+1]⁺ 478.1.

Example 6

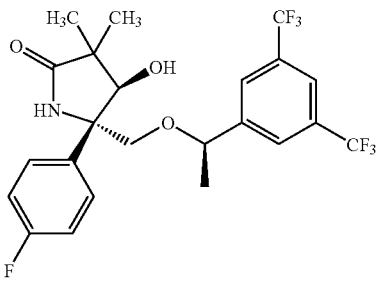

In a flame dry, 15 ml RBF, Example 5 (0.047 g, 0.098 mmol, 1.0 equiv) was taken up in dry THF (4 ml). LiBH₄ (0.003 g, 0.147 mmol, 1.5 equiv) was added to the reaction mixture and the reaction was stirred over night at RT. The reaction was monitored by TLC in 3:2 EtOAc/hexane. The reaction went to completion, hence, it was concentrated. The crude reaction mixture was taken up in CH₂Cl₂, quenched with H₂O (1 ml), and washed with 6 N HCl (5 L), followed by saturated NaHCO₃ (5 ml). All organic layers were combined and dried over Na₂SO₄ and concentrated. Purification was carried out using Prep plate in 3:2 EtOAc/hexane to give Example 6 (0.0387 g, 80%).

Electrospray MS [M+1]⁺ 494.1.

Example 8

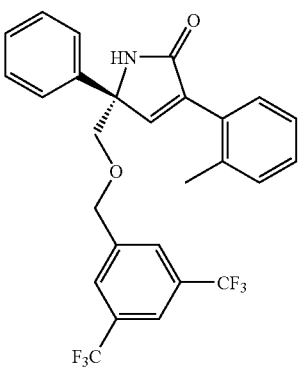

Example 8 (14% overall yield) was prepared in a method similar to that used to prepare the Example 11, infra, using compound 6a in place of compound 6.

Electrospray MS [M+1]$^+$ 506.1.

Example 9

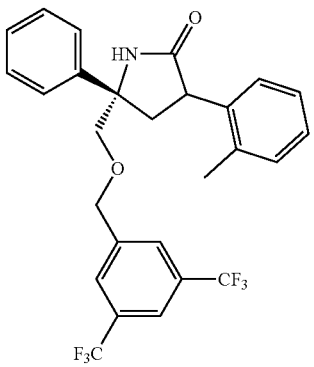

The Example 9 (91% overall yield) was prepared in a method similar to that used for the preparation of Example 12, using Example 8 in place of compound 11.

Electrospray MS [M+1]$^+$ 508.1.

Example 10

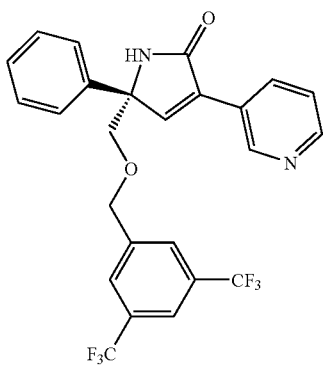

The Example 10 (23% overall yield) was prepared from compound 6a using a method similar to that used to prepare Example 8.

Electrospray MS [M+1]$^+$ 493.1.

Example 11

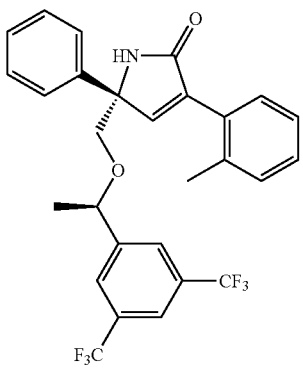

Step 1:

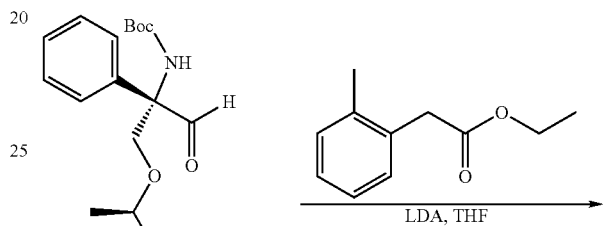

Compound 6

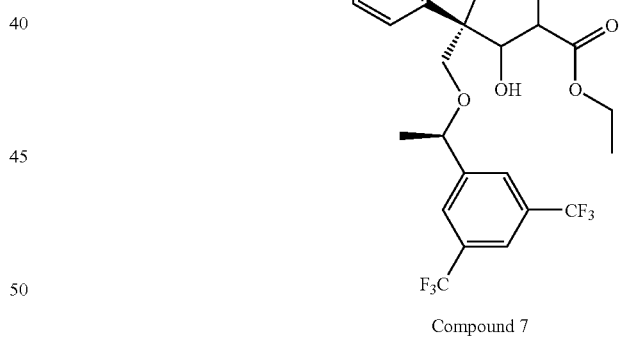

Compound 7

To a solution of o-tolyl acetate (0.16 ml, 0.889 mmol) in dry THF (5 ml), 2M LDA (0.45 ml, 0.889 mmol) was slowly added at −78° C. The resulting reaction mixture was stirred at −78° C. for 1 hour. Then, a solution of compound 6 (0.45 g, 0.889 mmol) in dry THF (5 ml) was added to the reaction mixture drop wise. The resulting reaction mixture was stirred at −78° C. for 2 hours, then quenched with a solution of acetic acid (0.060 ml, 1.048 mmol) in THF (1 ml). After 5 minutes, the solution was allowed to warm to 23° C. The solution was then poured into 200 ml of EtOAc and washed with 100 ml of saturated aqueous NaHCO$_3$. The organic layer was dried over Na$_2$SO$_4$ and concentrated to give compound 7 (0.4 g) crude product, which was used in the next step without further purification.

Step 2:

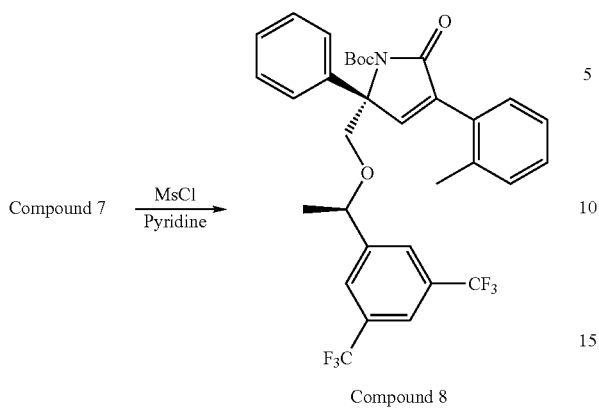

Compound 7 →(MsCl/Pyridine)

Compound 8

To a solution of compound 7 (0.4 g) in dry CH$_2$Cl$_2$ (10 ml), Et$_3$N (2.45 ml, 1.755 mmol), followed by MsCl (0.1 ml, 1.292 mmol) were added. The resulting mixture was stirred at 23° C. for 3 hours and concentrated. Dry pyridine (5 ml) was added to the concentrated mixture. The resulting solution was then heated at 90° C. for 2 hours, concentrated, and poured into 200 ml of EtOAc and washed with 100 ml of saturated aqueous NaHCO$_3$. The organic layer was dried over Na$_2$SO$_4$ and concentrated. Purification using Biotage chromatography with 9:1 hexane/EtOAc, 85:15 hexane/EtOAc gave compound 8 (0.4 g, 73% over two steps).

Step 3:

To a solution of compound 8 (0.4 g, 0.646 mmol) in CH$_2$Cl$_2$ (10 ml), 4M HCl in dioxane (1.6 ml, 6.46 mmol) was added at 0° C. and stirred for 2 hours. The reaction mixture was poured into 200 ml of CH$_2$Cl$_2$ and washed with 100 ml of saturated aqueous NaHCO$_3$ and 100 ml of saturated aqueous NaCl, successively. An organic layer was dried over anhydrous Na$_2$SO$_4$, filtered and concentrated. Purification using Biotage chromatography with 4:1 hexane/EtOAc and 2:1 hexane/EtOAc gave Example 11 (0.060 g, 20%).

Electrospray MS [M+1]$^+$ 520.1.

Example 12

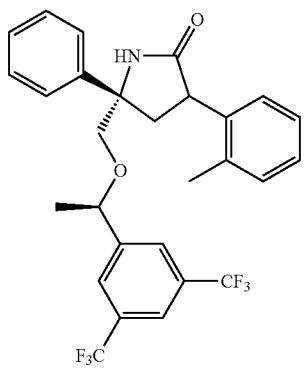

A reaction mixture of compound 11 (0.060 g, 0.116 mmol), EtOH (15 ml) and 10% Pd/C (0.015 g) was stirred under hydrogen at 23° C. for 18 hours. The reaction mixture was then filtered over a short pad of celite and concentrated. Purification using Biotage chromatography with 2:1 hexane/EtOAc gave Example 12 (0.055 g, 91%).

Electrospray MS [M+1]$^+$ 522.1.

Example 13

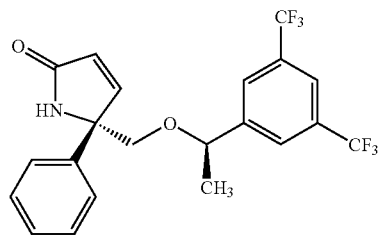

Example 13 was prepared in a method similar to that used to prepare the Example 3, except Example 14 was used in place of Examples 2a and 2b. Example 13 was obtained in a 73% yield.

Electrospray MS [M+1]$^+$ 430.1.

Example 14

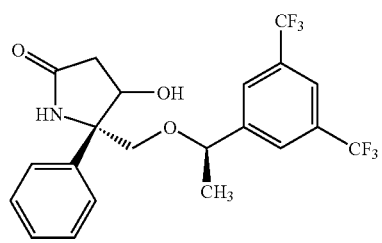

Example 14 was prepared using a method similar to that used to prepare Examples 2a and 2b, except that non-fluoro amino amide compound 1a was used in place of compound 1:

Compound 1a

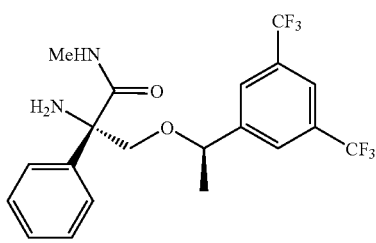

Compound 1a was prepared using a procedure analogous to that described in WO 01/44200 (2001) for compound 96. Example 14 was obtained in a 22% yield.

Electrospray MS [M+1]$^+$ 448.1.

Example 15

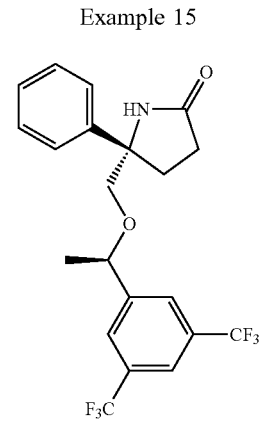

Step 1:

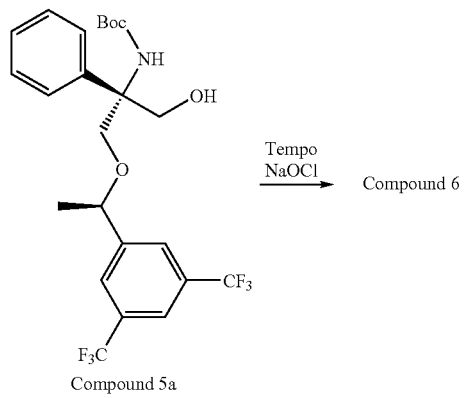

In a 500 ml RBF, compound 5a (4.3 g, 8.48 mmol, 1.0 equiv) was taken up in EtOAc (80 ml) and the reaction mixture was cooled to 0° C. in an ice bath. Saturated NaHCO$_3$ (80 ml) was then added to the reaction mixture, which was then stirred for 10 min at 0° C. NaBr (0.873 g, 8.48 mmol, 1.0 equiv) was added to the reaction mixture, followed by TEMPO (0.014 g, 0.0848 mmol, 0.1 equiv), and the reaction mixture was stirred for 15 minutes. Bleach (5.25% in H$_2$O) (15.7 ml, 11.04 mmol, 1.3 equiv) was added to the reaction mixture, which turned bright yellow in color. The reaction was monitored by TLC in 1:4 EtOAc/hexane. The reaction went to completion, hence, it was quenched with saturated Na$_2$S$_2$O$_3$ (20 ml). The product was taken up in EtOAc (150 ml), washed with saturated NaHCO$_3$ (2×150 ml), dried over Na$_2$SO$_4$ and concentrated to give compound 6 (4.27 g, 99%).

NMR (partial) for compound 6: $^1$H NMR: (CDCl$_3$, 500 MHz): δ 9.4(s), 7.7(s), 7.5(s), 5.65(bs), 4.5(q), 1.3(d).

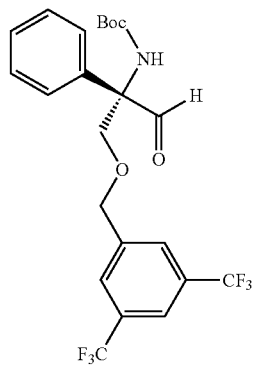

The non-benzylic methyl aldehyde compound 6a was prepared using a procedure analogous to that used to prepare compound 6, supra. Compound 6a was used in the preparation of Examples 8, 9 and 10.

Step 2:

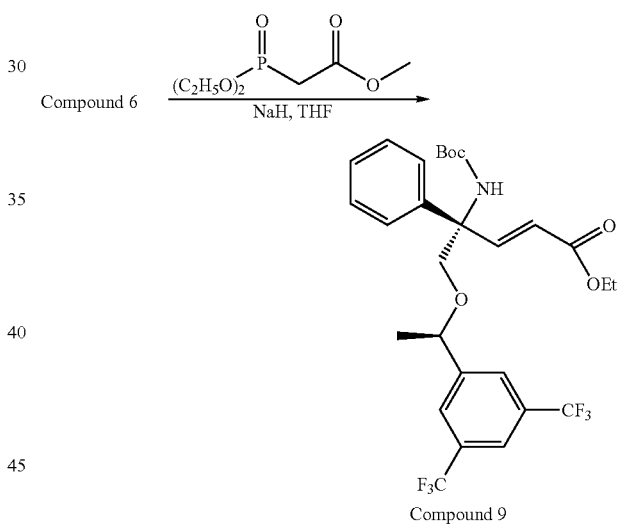

In a flame dry, 250 ml RBF, methyl di-ethyl phosphonate (1.95 ml, 10.64 mmol, 1.7 equiv) was taken up in dry THF (25 ml). The reaction mixture was cooled to 0° C. in an ice bath. NaH (60% dispersion in mineral oil) (0.375 g, 9.39 mmol, 1.5 equiv) was added to the reaction mixture, the solution was stirred at 0° C. for 15 minutes. Boc aldehyde compound 6 (3.16 g, 6.26 mmol, 1.0 equiv) was taken up in THF (20 ml) and was added to the reaction mixture. The reaction mixture was then warmed to RT and stirred for 3.5 hours. The reaction was monitored by TLC in 1:4 EtOAc/hexane. The reaction went to completion, hence, the product was concentrated. A short plug was run in 1:9 EtOAc/hexane to give compound 9 (3.24 g, 92%).

Electrospray MS [M+1]$^+$ 562.1.

Step 3:

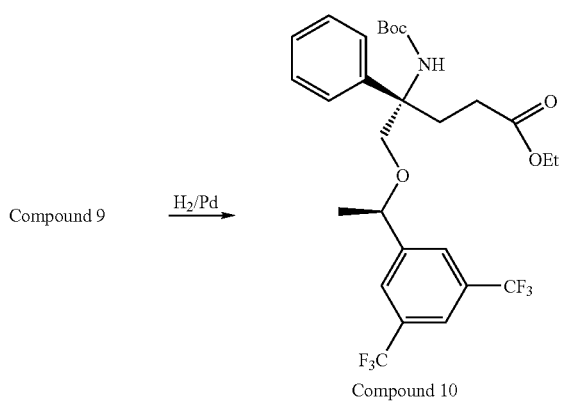

Compound 9 →(H₂/Pd) Compound 10

Unsaturated (Boc) ester compound 9 (3.29 g, 5.86 mmol, 1.0 equiv) was taken up in absolute EtOH (75 ml). The reaction mixture was degassed and flushed with N₂ several times. 10% Pd/carbon (0.541 g, 0.1 equiv) was then added, and the reaction mixture was again degassed and flushed with H₂ several times. The reaction mixture was stirred over night. The reaction was monitored by NMR and no vinyl peaks were seen. The reaction went to completion, hence, the product was filtered through a celite plug, rinsed with EtOH, and concentrated. Purification was carried out using a silica plug 1:4 EtOAc/hexane to give compound 10 (3.0 g, 91%).

NMR (partial) for compound 10: $^1$H NMR: (CDCl$_3$, 500 MHz): δ 7.8(s), 7.55(s), 5.25(bs), 4.5(q), 1.4(d).

Step 4:

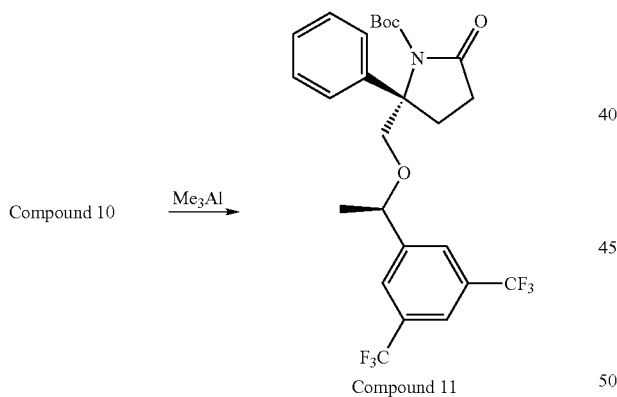

Compound 10 →(Me₃Al) Compound 11

In a flame dry, 500 ml RBF, compound 10 (3.0 g, 5.32 mmol, 1.0 equiv) was taken up in dry toluene (40 ml) and cooled to 0° C. in an ice bath. To this reaction mixture, Me₃Al (5.32 ml, 10.6 mmol, 2.0 equiv) was added slowly with a needle outlet. The solution was stirred at 0° C. for 30 minutes, then warmed to RT for 15 minutes. The reaction was monitored by TLC in 1:4 EtOAc/hexane. The reaction went to completion, hence, the product was quenched with saturated Na K tartrate solution. The reaction mixture was stirred at RT with saturated NaCl (10 ml) solution to break the emulsion. EtOAc (100 ml) was used to extract the product, which was then washed with saturated NaCl (2×25 ml), dried over Na₂SO₄, and concentrated. Purification was carried out using Biotage (40M) column 9:1 hexane/EtOAc to give compound 11 (2.4 g, 84%).

Electrospray MS [M+1−100]⁺ 432.1.

Step 5:

In a 250 ml, RBF, (Boc) Lactam compound 11 (2.3 g, 4.08 mmol, 1.0 equiv) was taken up in dry CH₂Cl₂ (60 ml) and cooled to 0° C. in an ice bath. TFA (3.14 ml, 40.8 mmol, 10.0 equiv) was then added drop wise to the reaction mixture. The solution was stirred at 0° C. for 15 minutes, then warmed to RT for 2.5 hours. The reaction was monitored by TLC in 1:4 EtOAc/hexane. The reaction went to completion, hence, it was quenched with saturated NaHCO₃, and the product was extracted with CH₂Cl₂ (100 ml), dried over Na₂SO₄, and concentrated. Purification was carried out using Biotage (40M) column 1:4 hexane/EtOAc. Recrystallization was carried out using neat heptane to give Example 15 as a white crystalline solid (1.6 g, 84%).

Electrospray MS [M+1]⁺ 432.1.

Examples 16 and 17

Example 16

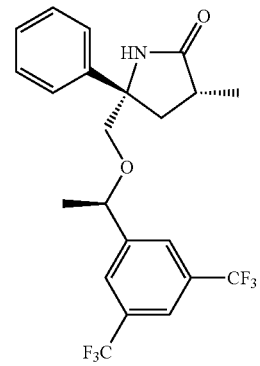

Example 17

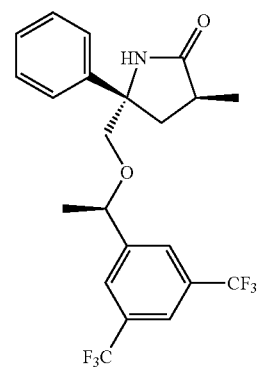

In a 100 ml, flame dry RBF, (Boc) lactam compound 11 (0.3 g, 0.56 mmol, 1.0 equiv) was taken up in dry THF (15 ml). The reaction mixture was cooled to −78° C. Freshly prepared 0.5 M LDA (1.24 ml, 0.62 mmol, 1.1 equiv) was then added drop wise at −78° C. The reaction mixture was stirred for an hour and CH₃I (35 μL, 0.56 mmol, 1.0 equiv) was added to it. The reaction monitored by TLC in 2:1 EtOAc/hexane. Trace amounts of starting material were still present, hence, the reaction was quenched using acetic acid (35 μL, 0.62 mmol, 1.1 equiv). The product was extracted with EtOAc (2×15 ml), washed with saturated NaHCO₃ (2×100 ml), dried over Na₂SO₄, and concentrated. Purification was carried out using Biotage (40M) column 9:1 hexane/EtOAc to give (Boc) methyl Lactam as Isomer A (0.100 g) and Isomer B (0.023 g) with a combined overall yield of 40%.

NMR for Isomer A: $^1$H NMR: (CDCl$_3$, 400 MHz): δ 7.8(s), 7.79(s), 4.6(q), 4.1(d), 3.9(d), 2.5(m), 2.25(m), 1.55 (d), 1.35(s), 1.2(d).

NMR for Isomer B: $^1$H NMR: (CDCl$_3$, 400 MHz): δ 7.8(s), 7.79(s), 4.65(q), 4.1(q), 2.85–2.7(m), 1.8(dd), 1.59 (d), 1.3(d), 1.2(d).

Isomer A (0.04 g, 0.074 mmol, 1.0 equiv) was taken up in CH$_2$Cl$_2$ (1.4 ml) and cooled to 0° C. 4M HCl/dioxane (185 μl, 0.74 mmol, 10 equiv) was added drop wise to the reaction mixture. The reaction was monitored by TLC 7:3 hexane/EtOAc. After 3 hours, the reaction was completed, hence, the product was diluted with CH$_2$Cl$_2$, washed with saturated NaHCO$_3$ (2×100 ml), dried over Na$_2$SO$_4$, and concentrated to give Example 16 (0.03 g, 89%). No purification was needed.

Electrospray MS [M+1]$^+$ 446.1.

Isomer B (0.01 g, 0.018 mmol, 1.0 equiv) was taken up in CH$_2$Cl$_2$ (350 μl) and cooled to 0° C. 4M HCl/dioxane (46 μl, 0.18 mmol, 10 equiv) was added drop wise to the reaction mixture. The reaction was monitored by TLC 7:3 hexane/EtOAc. After 3 hours, the reaction was completed, hence, the product was diluted with CH$_2$Cl$_2$, washed with saturated NaHCO$_3$ (2×100 ml), dried over Na$_2$SO$_4$, and concentrated. Purification was carried out using 3:2 hexane/EtOAc to give Example 17 (0.003 g, 42%).

Electrospray MS [M+1]$^+$ 446.1.

Example 18

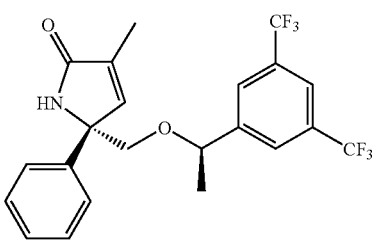

A 1.6M solution of n-BuLi in hexane (1.1 ml, 1.8 mmol) was added to a 3 ml anhydrous, THF solution of diisopropylamine (0.25 ml, 1.8 mmol) at −78° C. under nitrogen. After 40 minutes, triethyl-2-phosphonopropionate (0.39 ml, 1.8 mmol) was added drop wise over 5 minutes to the reaction mixture. A thick, white suspension resulted, and was allowed to stir for 25 minutes before the addition of a 3 ml THF solution of the aldehyde compound 6 (0.45 g, 0.89 mmol) via a cannula over 5 minutes. The cold bath was removed and the reaction mixture was allowed to stir at RT for 18 hours. The reaction was treated with 10 ml of saturated NH$_4$Cl solution and diluted with 50 ml of EtOAc. The phases were separated, and the organic layer was washed with 10 ml of water and brine, dried over Na$_2$SO$_4$, filtered, and concentrated in a vacuum to provide colorless oil. Purification of the crude material with flash chromatography on a silica gel, eluting with 40% EtOAc/hexane afforded 74 mg (19%) of Example 18 as a colorless oil.

HRMS (FAB) calculated for C$_{22}$H$_{20}$F$_6$NO$_2$ (M+1) 444.1398. found 444.1402.

Example 19

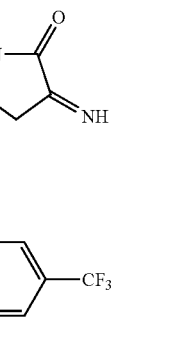

Step 1:

Compound 11 $\xrightarrow[\text{THF}]{\substack{\text{0.5M KHMDS}\\\text{Trisyl Azide}}}$ Compound 12

+

Compound 13

In a dry, 200 ml RBF, 0.5 g of KHMDS (8.27 ml, 4.14 mmol, 1.1 equiv) was taken up and cooled to −78° C. under N$_2$. N-(Boc) Lactam compound 11 (2.0 g, 3.77 mmol, 1.0 equiv) in dry THF was added via a cannula at −78° C. The reaction mixture turned pale yellow in color after stirring for 30 minutes. Trisyl azide in THF was then added via a cannula to the reaction mixture. The reaction mixture was stirred for 30 minutes and then quenched at −78° C. using propionic acid (1.12 ml, 15.08 mmol, 4.0 equiv). The reaction mixture was then warmed to 30° C. and stirred for 2 hours. Monitoring by TLC 7:3 hexane/EtOAc showed trace amounts of starting material were remaining. The reaction mixture was diluted with EtOAc, washed with saturated NaHCO$_3$, and dried over Na$_2$SO$_4$ to give a crude product. Purification was carried out using a Biotage (40M) column using 4:1 hexane/EtOAc to elute the desired product, (Boc) azide (0.450 g), and starting material (0.200 g), and also to elute compound 13 (0.450 g) as a by-product with an overall yield of 51%. Deprotection of compound 13 was accomplished using a procedure similar to that used in the preparation of Example 15, to give Example 19 (0.355 g, 95%).

3.43 mmol, 4.4 equiv). The reaction mixture was warmed to RT, diluted with EtOAc, washed over saturated NaHCO$_3$, and dried over Na$_2$SO$_4$ to give a crude product. Purification was carried out using Biotage (40S) column using 9:1 hexane/EtOAc to elute desired product (Boc) Azide (0.120 g), and also to elute compound 14 (0.087 g) as a byproduct. Deprotection of compound 14 was accomplished using a procedure similar to that used in the preparation of Example 15, to give Example 20 (0.65 g, 90%).

Electrospray MS [M+1]-Boc$^+$ 446.1.

Example 20

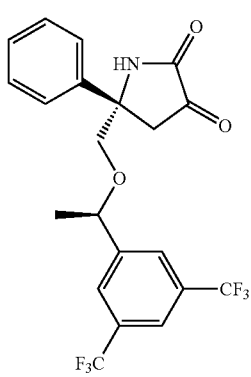

Example 21

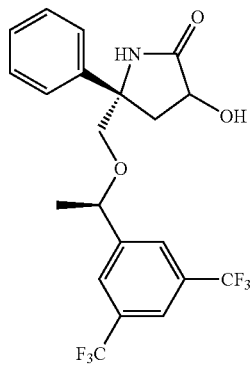

Step 1:

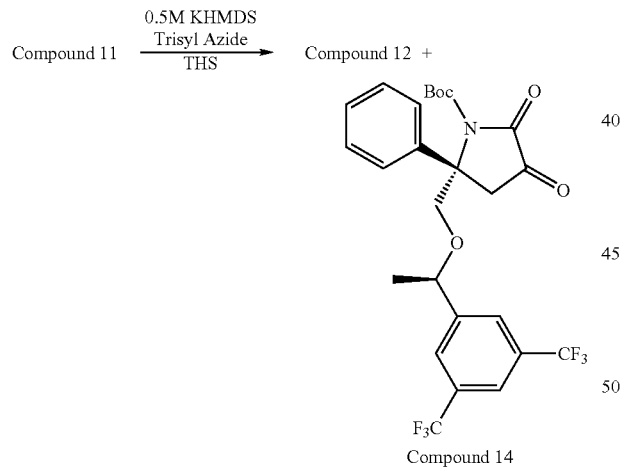

Compound 14

A 25 ml flame dry RBF was charged with (Boc) Lactam compound 11 (0.415 g, 0.78 mmol, 1.0 equiv) in dry THF. The reaction mixture was cooled to −78° C. and 0.5M KHMDS (1.72 ml, 0.859 mmol, 1.1 equiv) was added drop wise to it. The reaction mixture turned bright yellow in color. After 30 minutes, a solution of trisyl azide (0.603 g, 1.95 mmol, 2.5 equiv) in dry THF was added to the reaction mixture and stirred for 3 hours. Monitoring by TLC 7:3 hexane/EtOAc showed some starting material was left, hence. The reaction mixture was stirred again for another hour, then quenched at −78° C. using acetic acid (198 μl, In a 10 ml RBF, diketo Lactam Example 20 (0.019 g, 0.049 mmol, 1.0 equiv) was taken up in dry THF LiBH$_4$ (1.4 mg, 0.064 mmol, 1.5 equiv) was then added to the reaction mixture, which was stirred at RT under N$_2$. The reaction mixture was stirred for 6 hours and monitored by TLC 3:2 EtOAc/hexane. The reaction was completed, hence, it was quenched using H$_2$O. The reaction mixture was diluted with EtOAc, washed with saturated NaHCO$_3$, and dried over Na$_2$SO$_4$ to give a crude product. Purification was carried using Prep plate in 100% EtOH to give Example 21 (0.016 g, 83%).

Electrospray MS [M+1]$^+$ 448.1.

Example 22

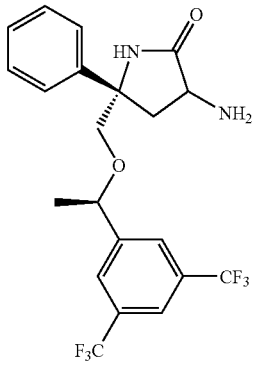

Method A:
Step 1:

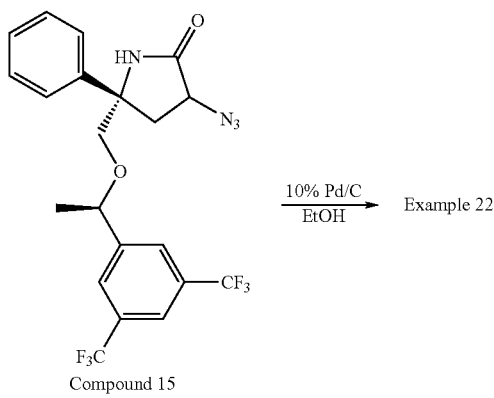

Compound 15

Compound 15 (0.155 g, 0.328 mmol, 1.0 equiv) was taken up in absolute EtOH (15 ml) in a 200 ml RBF. The reaction mixture was degassed using a $N_2$ vacuum several times. 10% Pd/C (0.134 g) was added and the reaction mixture was stirred at RT over night at atmospheric pressure. The reaction was monitored by TLC 7/3 hexane/EtOAc, followed by 9/1 EtOAc/$CH_3OH$. The reaction was completed, hence, it was filtered through celite, and concentrated to give a pale yellow oil as Example 22 (0.100 g, 68%).

Electrospray MS $[M+1]^+$ 447.1.

Method B:
Step 1:

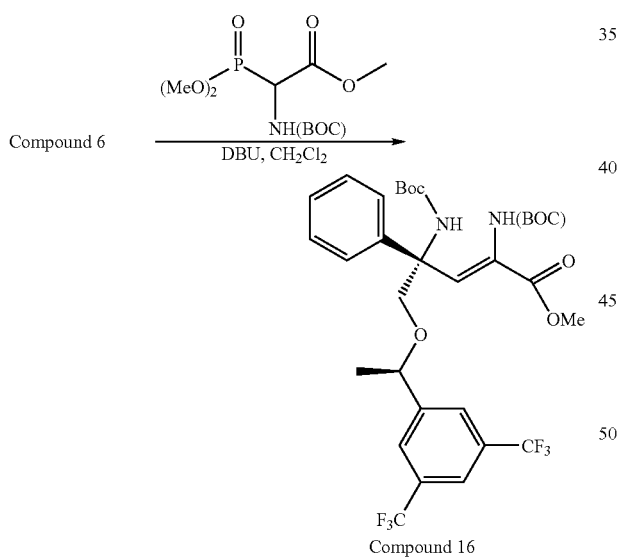

(Boc)-phosphonate (3.99 g, 13.46 mmol, 2.0 equiv) was taken up in $CH_2Cl_2$ (4 ml), and treated with DBU (2.02 ml, 13.46 mmol, 2.0 equiv). The reaction mixture was stirred for 15 minutes, and a solution of aldehyde compound 6 (3.4 g, 6.73 mmol, 1.0 equiv) in $CH_2Cl_2$ (4 ml) was added to it. The reaction mixture was stirred over night, and monitored by TLC 4:1 hexane/EtOAc. The reaction was completed, hence, it was diluted with $CH_2Cl_2$ (50 ml), washed with (25 ml) saturated $NaHCO_3$, followed by (25 ml) Brine, and dried over $Na_2SO_4$. Purification was carried out using a silica plug 4:1 hexane/EtOAc to elute the compound 16 (2.4 g, 54%).

Electrospray MS $[M+1]^+$ 677.1.
Step 2:

Compound 16 (0.048 g, 0.071 mmol, 1.0 equiv) was dissolved in EtOAc (5 ml) and treated with stoichiometric 10% Pd/C (0.076 g, 0.071 mmol, 1.0 equiv) under an inert atmosphere. The reaction mixture was hydrogenated at atmospheric pressure and monitored by TLC 4:1 hexane/EtOAc. The reaction was also monitored by NMR, and no vinyl peaks were seen. The reaction went to completion, hence, the reaction mixture was filtered through a celite plug, and concentrated to give compound 17 (0.048 g, 90%).

Electrospray MS $[M+1]^+$ 677.1.

Compound 17 was deprotected using a procedure similar to that used in the preparation of Example 15, to give Example 22 (0.355 g, 95%).

Method C:
Step 1:

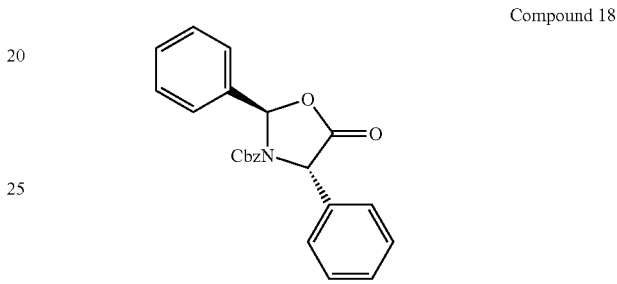

Compound 18

Compound 18 was prepared using a synthetic procedure reported in M. J. O'Donnell, Z. Fang, X. Ma and J. C. Huffman, *J. Am. Chem. Soc.*, 1997, 46, 617.

Step 2:

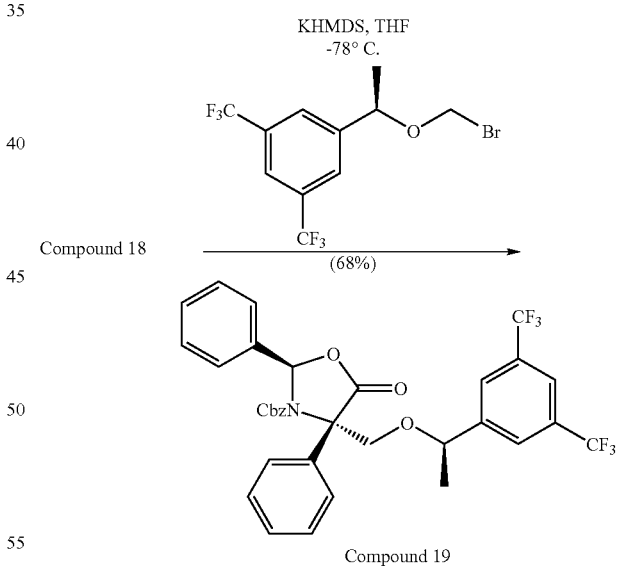

To a nitrogen purged solution of oxazolidinone compound 18 (10.0 g, 0.027 mol) in THF (500 ml) at −8° C., a solution of KHMDS (64 ml, 0.5M in toluene) was added. After the reaction mixture has been stirred at −78° C. for 30 minutes, a solution of bromomethyl ether (11.3 g, 0.032 mol) in THF (100 ml) at −78° C. was cannulated into the reaction mixture. The solution was stirred at −78° C. for 1 hour before being quenched with a saturated $NH_4Cl$ solution at −78° C. The reaction mixture was warmed to RT, and water and EtOAc were added. Layers of the reaction mixture were separated. The aqueous layer was extracted with EtOAc (×2). The combined organic layers were dried (MgSO$_4$) and filtered, and solvents in the filtrate were removed by vacuum. Purification using column chromatography [hexanes-toluene, 1:1 (v/v)] gave compound 19 (11.7 g, 68%) as a colorless oil.

Electrospray MS [M+1]$^+$ 644.1.

Step 3:

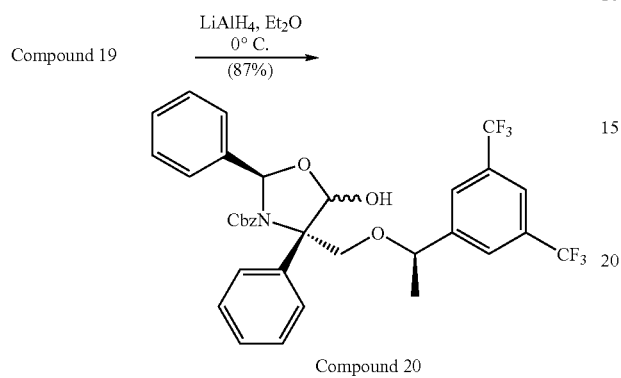

Compound 20

To a solution of lactone 19 (35.2 g, 0.055 mol) in diethyl ether at 0° C., a solution of LAH (17.8 ml, 0.018 mol) in diethyl ether was added. The reaction mixture was stirred at 0° C. for 30 minutes before being quenched with saturated NH$_4$Cl solution. Water was added and the resulting layers were separated. The separated aqueous layer was extracted with EtOAc (×2), dried (MgSO$_4$), and filtered. Solvents in the filtrate were removed in a vacuum to give a colorless oil. The oil was dissolved in acetic acid (240 ml) at RT, and water (60 ml) was added. After being stirred at RT for an hour, the white solid was filtered, washed with water and dried under a high vacuum. Recrystallization (hexanes-toluene) was carried out to give compound 20 (23 g) as a white powder. All filtrates were combined, and the solvents were removed in a vacuum to give a yellow oil. The above procedure (HOAc—H$_2$O, followed by recrystallization) was repeated to give another batch of lactol compound 20 (3 g). Solvents in the filtrate were removed in a vacuum, and the resulting oil was subjected to column chromatography [hexanes-EtOAc, 6:1(v/v)] to give a third batch of compound 20 (4 g). The combined yield for compound 20 was 30 g, 87%.

Electrospray MS [M+1]$^+$ 646.2.

Step 4:

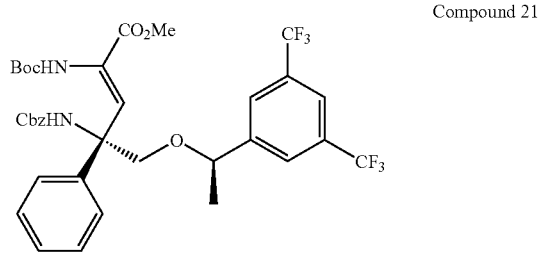

Compound 21

Compound 21 was prepared using a procedure similar to that used for compound 16.

Step 5:

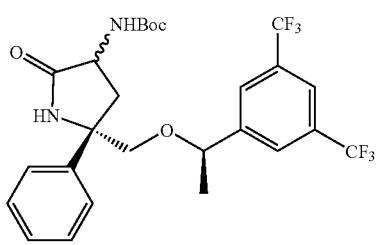

Compound 22

Compound 21 was hydrogenated at atmospheric pressure, using 10% Pd/C to give compound 22, which was deprotected using TFA to give Example 22.

Examples 23a and 23b

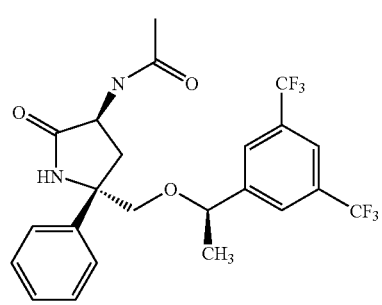

Example 23a

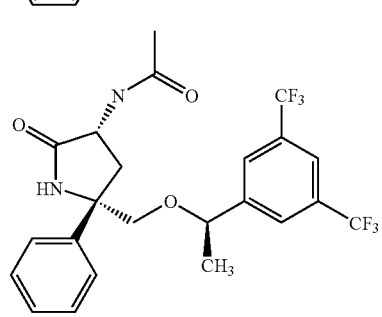

Example 23b

In a 10 ml, flame dry RBF, crude amine Lactam Example 22 (0.028 g, 0.063 mmol, 1.0 equiv) was taken up in dry CH$_2$Cl$_2$ (1.5 ml). The reaction mixture was cooled to 0° C. DIEA (23 µl, 0.13 mmol, 2.1 equiv) was added to the reaction mixture, which was stirred at 0° C. for 15 minutes. Acetyl chloride (6.7 µl, 0.094 mmol, 1.5 equiv) was added to the reaction mixture drop wise, and gas evolved upon the addition. The reaction mixture was warmed to RT and stirred over night. The reaction mixture was monitored by TLC in 95:5 EtOAc/CH$_3$OH. The reaction was completed, hence, it was quenched with saturated NaHCO$_3$, extracted with CH$_2$Cl$_2$ (2×5 ml), washed with saturated NaHCO$_3$ (2×5 ml), dried over Na$_2$SO$_4$, and concentrated. Purification was carried out using a Prep plate in 98:2 EtOAc/CH$_3$OH to separate both (bottom) Example 23b isomer and (top) Example 23a isomer. The overall yield for both isomers was 0.013 g, 43%.

NMR for Example 23a: $^{13}$C NMR (CDCl$_3$, 500 MHz): δ176.0, 172.0, 147.1, 143.7, 130.3, 129.3, 127.5, 125.7, 63.7, 52.7, 43.0, 25.4, 24.3.

NMR for Example 23b: $^{13}$C NMR (CDCl$_3$, 500 MHz): δ176.0, 172.0, 147.4, 143.7, 130.7, 129.7, 127.8, 126.7, 64.2, 51.7, 42.8, 25.7, 24.9.

Examples 24a and 24b

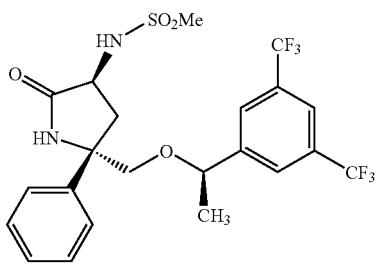
Example 24a

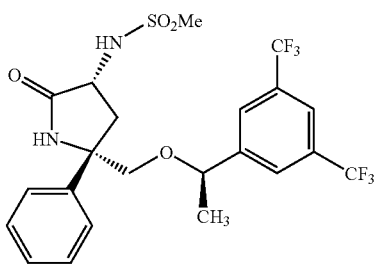
Example 24b

In a 25 ml, flame dry RBF, crude amine Lactam Example 22 (0.119 g, 0.268 mmol, 1.0 equiv) was taken up in dry $CH_2Cl_2$ (5 ml). The reaction mixture was cooled to 0° C. DIEA (98 μl, 0.056 mmol, 2.1 equiv) was added to the reaction mixture, which was stirred at 0° C. for 15 minutes. $MeSO_2Cl$ (32 μl, 0.402 mmol, 1.5 equiv) was then added to the reaction mixture drop wise, and gas evolved upon the addition. The reaction mixture was then warmed to RT and stirred for 2 hours. The reaction was monitored by TLC in 100% EtOAc. The reaction was completed, hence, it was quenched with saturated $NaHCO_3$, an aqueous layer was extracted with $CH_2Cl_2$ (2×15 ml), and the crude product was dried over $Na_2SO_4$, and concentrated. Purification was carried out using a Biotage (40S) column using 3:2 EtOAc:hexane. Both isomers were co-eluted, hence, all the fractions were concentrated and the reaction mixture was separated using HPLC. An AD column was used with 9:1 hexane/IPA to separate Isomer A as Example 24a (0.057 g) and Isomer B as Example 24b (0.041 g). The overall yield was 69%.

NMR for Example 24a: $^{13}C$ NMR ($CDCl_3$, 500 MHz): δ174.3, 142.0, 132.3, 124.7, 122.5, 62.6, 54.6, 42.4, 24.3.

NMR for Example 24b: $^{13}C$ NMR ($CDCl_3$, 500 MHz): δ173.9, 141.4, 132.5, 125.3, 122.3, 62.9, 53.3, 42.1, 24.3.

Examples 25a and 25b

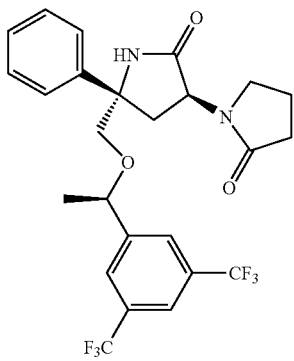
Example 25a

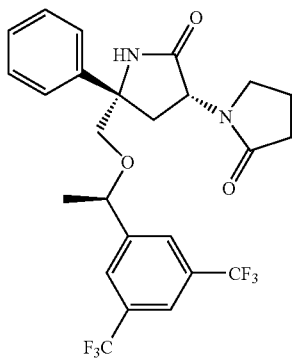
Example 25b

To a solution of amino-lactam Example 22 (0.100 g, 0.224 mmol) in toluene (7 ml) at 0° C., was added a solution of 2 M $AlMe_3$ in toluene (0.14 ml, 0.28 mmol). The reaction mixture was warmed to RT and stirred for 15 minutes. Ethyl 4-bromobutyrate was added, and the resulting mixture was heated at 100° C. for 18 hours. The reaction mixture was cooled to RT, poured into EtOAc (200 ml), and washed with 100 ml of saturated aqueous $NaHCO_3$ and 100 ml of saturated aqueous NaCl, successively. The organic layer was dried over anhydrous $Na_2SO_4$, filtered, and concentrated. HPLC separation on chiralpak OD column using a (90/10) hexane/IPA mixture gave Example 25a (40 mg, 35%), and Example 25b (20 mg, 18%).

Electrospray MS $[M+1]^+$ 515.1 for Example 25a.

Electrospray MS $[M+1]^+$ 515.1 for Example 25b.

Examples 26a and 26b

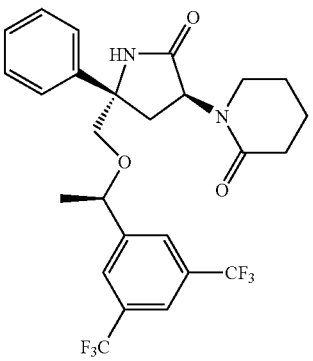
Example 26a

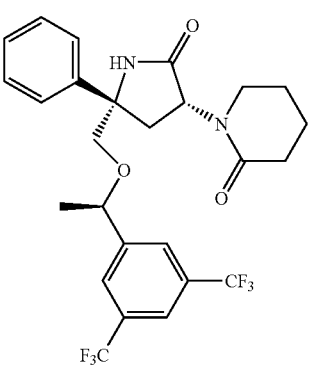
Example 25b

Step 1:

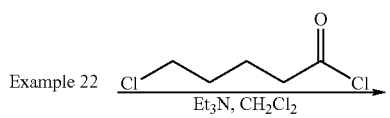

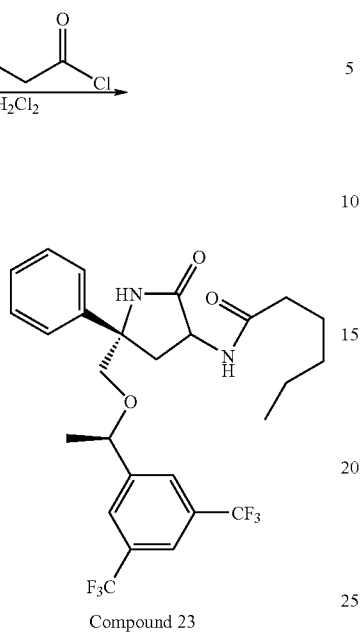

Compound 23

To a solution of amino-lactam Example 22 (0.100 g, 0.224 mmol) in $CH_2Cl_2$ (7 ml), was added triethyl amine (0.069 ml, 0.493 mmol). The reaction mixture was cooled to 0° C. and 5-chlorovaleryl chloride (0.035 ml, 0.269 mmol) was added. The resulting reaction mixture was stirred at 0° C. for 5 minutes, and then warmed to 23° C. and stirred for 18 hours. The reaction mixture was then poured into EtOAc (150 ml) and washed with 100 ml of saturated aqueous $NaHCO_3$. The organic layer was dried over anhydrous $Na_2SO_4$, filtered, and concentrated. 0.13 g of the crude compound 23 was obtained, which was used in the next reaction without further purification.

Step 2:

To a solution of compound 23 (0.13 g) crude product in dry THF (4 ml), was added NaH (60% dispersion in mineral oil, 0.020 g, 0.5 mmol) at 0° C. The reaction mixture was stirred for 5 minutes. The reaction mixture was then heated at 60° C. for 5 hours, cooled to 23° C., and quenched carefully with saturated aqueous NaCl (3 ml). The reaction mixture was then poured into saturated aqueous NaCl (100 ml) and extracted with EtOAc (100 ml). The organic layer was dried over anhydrous $Na_2SO_4$, filtered, and concentrated. HPLC separation on a chiralpak OD column using a (90/10) hexane/IPA mixture gave Example 26a (55 mg, 42%), and Example 26b (22 mg, 19%).

Electrospray MS $[M+1]^+$ 529.1 for Example 26a.

Electrospray MS $[M+1]^+$ 529.1 for Example 26b.

Examples 27a and 27b

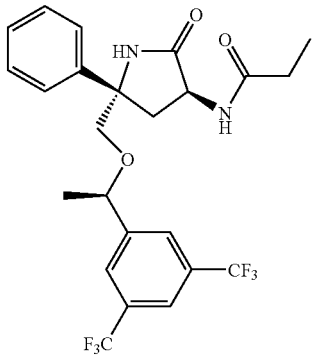

Example 27a

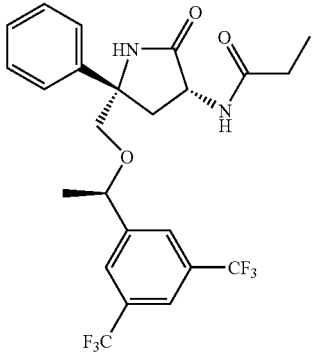

Example 27b

Using a procedure analogous to that used for the preparation of Examples 23a and 23b, the amino lactam Example 22 was converted to Examples 27a and 27b.

Example 28

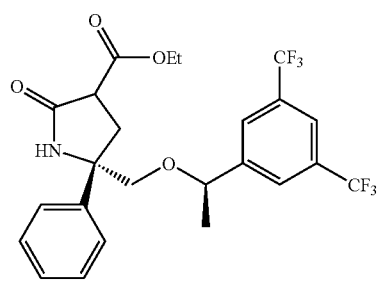

Step 2:

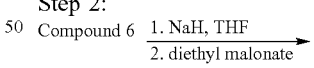

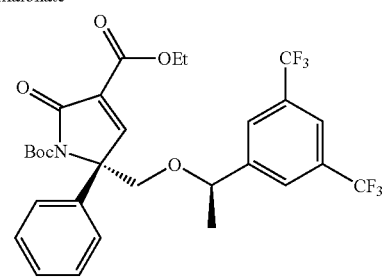

Compound 24

Diethylmalonate (44 µL, 0.29 mmol) was added at 0° C. under nitrogen to a suspension of NaH (7 mg, 0.29 mmol) in 0.5 ml of anhydrous THF. After 20 minutes, the anion was added to a 0.5 ml THF solution of the aldehyde compound 6 (72 mg, 0.14 mmol) at 0° C. The solution was allowed to warm to RT, and the reaction mixture was stirred for 24 hours. The reaction mixture was treated with 10 ml of a saturated NH$_4$Cl solution and diluted with 50 ml of EtOAc. The phases were separated, and the organic layer was washed with 10 ml of brine, dried over Na$_2$SO$_4$, filtered, and concentrated in a vacuum to provide a yellow oil. Purification of the crude material was accomplished with flash chromatography on a silica gel eluted with the gradient of 10% EtOAc/hexane to 20% EtOAc/hexane, and afforded 44 mg (52%) of Compound 24 as a colorless oil.

MS (+API) M+1=602.1.

Step 2:

Compound 24 $\xrightarrow{\text{TFA, CH}_2\text{Cl}_2}$

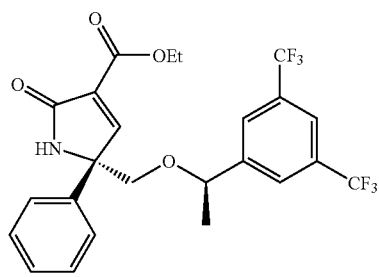

Compound 25

TFA (59 µL, 0.76 mmol) was added to the unsaturated lactam compound 24 (0.46 mg, 0.076 mmol) in 0.8 ml of THF at 0° C. under nitrogen. After 2 hours at 0° C., the reaction mixture was treated with 5 ml of a saturated NaHCO$_3$ solution and diluted with 20 ml of CH$_2$Cl$_2$. The phases were separated and the organic layer was washed with 10 ml of brine, dried over Na$_2$SO$_4$, filtered, and concentrated in a vacuum to provide 36 mg (95%) of compound 25 as a colorless oil. MS (+API) M+1=502.1.

Step 3:

The Example 28 was prepared from compound 25 in a manner similar to that used to prepare Example 4.

HRMS (FAB) calculated for C$_{24}$H$_{24}$F$_6$NO$_4$ (M+1) 504.1610. found 504.1613.

Example 29

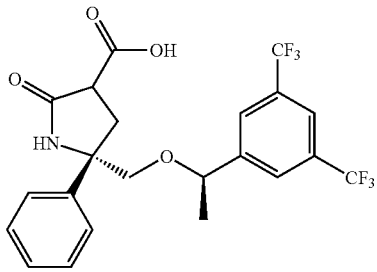

A 1M NaOH (0.25 ml, 0.24 mmol) solution was added to the ester Example 28 (0.12 g, 0.24 mmol) in 3 ml of THF. After 2 hours, the solution was acidified with a 1M HCl solution, and diluted with 10 ml of water and 40 ml of EtOAc. The phases were separated, and the organic layer was washed with two 10 ml portions of water, and 10 ml of brine, dried over Na$_2$SO$_4$, filtered, and concentrated in a vacuum to provide 0.11 g (96%) of Example 29 as a white solid foam.

HRMS (FAB) calculated for C$_{22}$H$_{20}$F$_6$NO$_4$ (M+1) 476.1297. found 476.1292.

Example 30

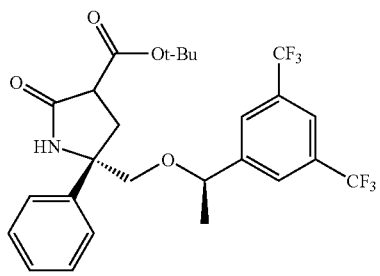

Under a nitrogen atmosphere, diphenylphosphorylazide (75 µL, 0.35 mmol) was added to a 1 ml solution of anhydrous t-butanol containing the acid Example 29 (0.11 g, 0.23 mmol) and triethylamine (48 µL, 0.35 mmol). The solution was refluxed for 24 hours, and then concentrated in a vacuum to afford an orange oil. Purification of the crude material was accomplished with flash chromatography on a silica gel eluted with the gradient of 15% EtOAc/hexane to 30% EtOAc/hexane, and afforded a 90 mg (72%) yield of Example 30 as a solid white foam.

HRMS (FAB) calculated for C$_{26}$H$_{28}$F$_6$NO$_4$ (M+1) 532.1923. found 532.1914.

Example 31

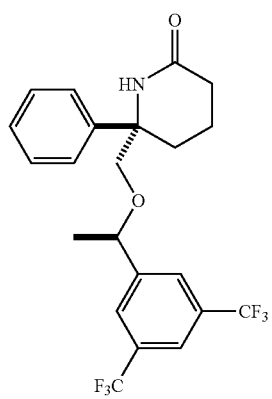

Using a procedure analogous to that used to prepare Example 4, the unsaturated lactam Example 32 (16 mg, 0.036 mmol) was hydrogenated to give Example 31 (14 mg, 87%).

Example 32

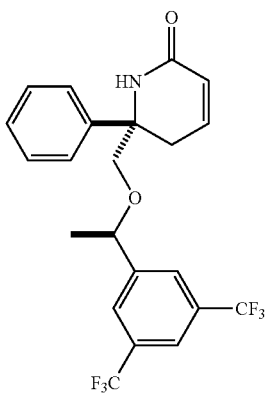

Step 1:

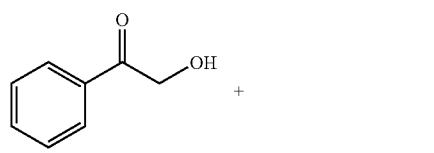

compound 26

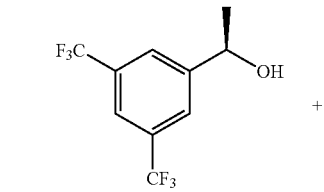

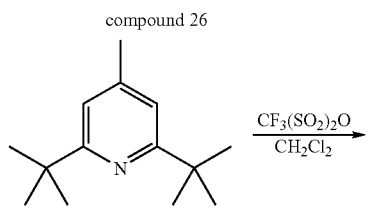

compound 27

Procedures for preparing compound 26 and compound 27 are shown in WO 01/44200.

Step 2:

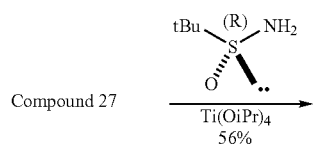

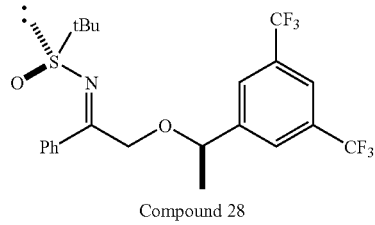

Compound 28

To a flask containing ketone compound 27 (1.05 g, 2.8 mmol) and (R)-t-butylsulfinamide (0.4 g, 3.3 mmol), was applied a vacuum for 5 minutes. Then, the flask was filled with $N_2$. Ti(OiPr)$_4$ (1 ml) was added through a syringe drop wise to the reaction mixture. The reaction mixture was stirred at 23° C. for 36 hours. The reaction mixture was then poured into 10 ml of brine and 20 ml EtOAc, and stirred vigorously for 10 minutes. The resulting suspension was passed through a pad of celite 545. The celite pad was washed with EtOAc several times. The combined organic solution was dried and concentrated under reduced pressure. Flash column chromatography afforded compound 28 (0.75 g, 56%).

Step 2:

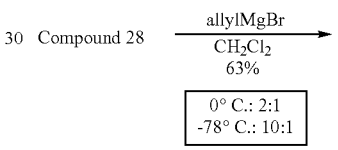

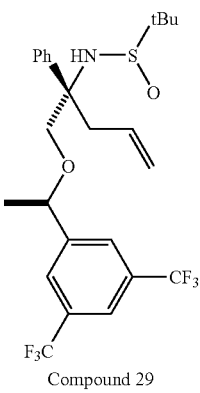

Compound 29

To a solution of sulfinimine compound 28 (2.44 g, 5.1 mmol) in CH$_2$Cl$_2$ at −78° C., was added drop wise allyl-magnesium bromide (6.1 ml, 6.1 mmol, 1M in Et$_2$O) through a syringe. After 3 hours at −78° C., the reaction mixture was quenched with a saturated NH$_4$Cl (aq) and allowed to warm to 23° C. The layers were separated, and the aqueous layer was extracted with EtOAc. The combined organic layers were dried and concentrated. Flash column chromatography gave compound 29 (1.672 g, 63%).

Step 3:

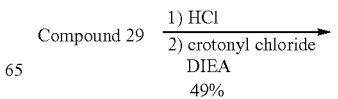

-continued

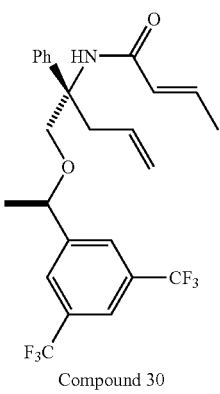
Compound 30

To sulfinamide compound 29 (0.087 g, 0.17 mmol) in 1 ml MeOH, was added 1 ml HCl in dioxane (4N). After having stirred the reaction mixture at 23° C. for 4hours, the volatiles were removed under reduced pressure. The remaining residue was dissolved in 2 ml of CH$_2$Cl$_2$. DIEA (58.4 µL, 0.34 mmol) and crotonyl chloride (19.4 µL, 0.17 mmol) were added to the reaction mixture, which was stirred overnight. The reaction mixture was diluted with 20 ml of EtOAc, washed with 5% HCl (aq.), half saturated NaHCO$_3$, and brine. The organic solution was dried and concentrated. The resulting residue was purified by flash column chromatography to afford compound 30 (0.04 g, 49%).

Step 4:

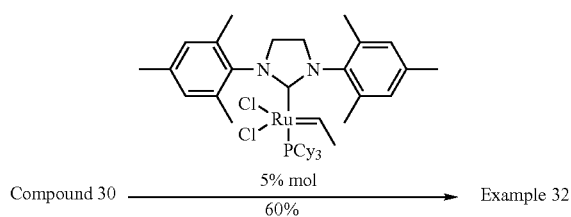

To diene compound 30 (0.04, 0.082 mmol) in 1 ml of CH$_2$Cl$_2$, was added a Grubbs' catalyst (3.5 mg, 0.004 mmol). The reaction mixture (solution) was heated under N$_2$ at 40–44° C. for 2 hours, then aged at 23° C. under open air overnight. The residue was subjected to flash column chromatography to give Example 32 (0.022 g, 60%).

Example 33

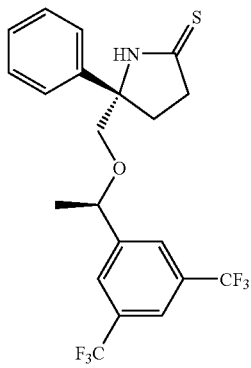

The compound of Example 15 (0.1 g, 0.232 mmol), Lawesson's reagent (0.052 g, 0.127 mmol) and toluene (3 ml) were mixed together and heated at 80° C. for 1.5 hours. The reaction mixture was cooled to RT and concentrated. Purification was accomplished using Biotage chromatography with 9:1 hexane/EtOAc, which Example 33 (0.080 g, 77%).

Electrospray MS [M+1]$^+$ 448.1.

Example 34

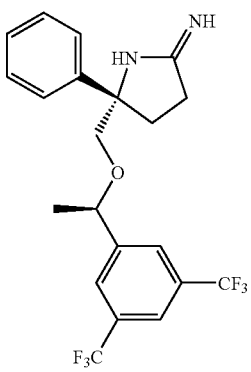

To a solution of Example 33 (0.080 g, 0.179 mmol) in THF (3 ml), was added CH$_3$I (0.014 ml, 0.214 mmol), and the reaction mixture was stirred at 23° C. for 12 hours. The reaction mixture was then concentrated to dryness, treated with saturated MeOH(NH$_3$) (7 ml), and stirred at 23° C. for 72 hours. The reaction mixture was then heated at 60° C. for 18 hours and concentrated. Purification was accomplished using a Biotage chromatography with 9:1 CH$_2$Cl$_2$/MeOH (NH$_3$), which gave Example 34 (0.008 g, 10%).

Electrospray MS [M+1]$^+$ 431.1.

Example 35

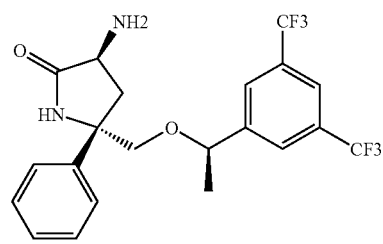

Step 1:

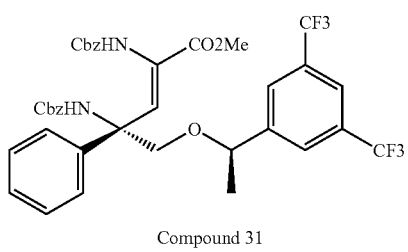
Compound 31

Compound 31 was prepared using a procedure similar to that described above in the preparation Example 22, Method B, Step 1, reacting compound 6 to obtain compound 31 using PO(OEt)$_2$CH(NHCbz)CO$_2$Me in place of PO(OMe)$_2$CH(N HBoc)CO$_2$Me.

Step 2:

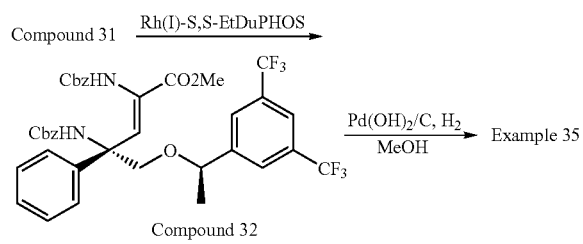

Compound 31 (3.0 g, 4.03 mmol, 1.0 equiv) was taken in MeOH (30 ml) in a parr reaction bottle. The reaction bottle was degassed using $N_2$ for 15 minutes. (+)-1,2-Bis((2S,5S)-2,5-diethylphospholano)benzene(cyclooctadiene)rhodium (I) trifluoromethanesulfonate (0.12 g, 0.16 mmol, 0.04 equiv) was added to the reaction mixture in a glove box, and shaken under hydrogen at 60 psig for 96 hours. The reaction mixture was transferred to a 200 ml RBF. 20% of $Pd(OH)_2/C$ (1 g) was added to the reaction mixture, which was stirred under hydrogen at 23° C. for 18 hours. The reaction was monitored by TLC 9/1 $EtOAc/CH_3OH$. The reaction was completed, hence, it was filtered through celite and concentrated. Purification was carried out using a silica plug 9:1 $EtOAc/MeOH(NH_3)$ to give Example 35 (1.3 g, 72%).

Electrospray MS $[M+1]^+$ 447.1.

Example 36

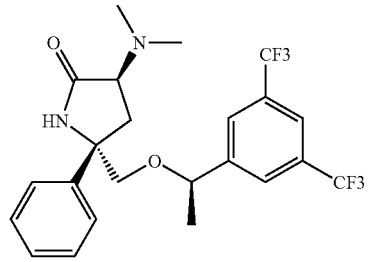

A mixture of Example 35 (0.1 g, 0.224 mmol, 1.0 equiv), 37% formaldehyde in water (0.134 ml, 1.79 mmol, 8.0 equiv), 10% Pd/C (0.080 g), and EtOH (5 ml) was stirred under hydrogen at 23° C. for 18 hours. The reaction mixture was then filtered over a short pad of celite and concentrated. Purification was accomplished using Gilson and water/$CH_3CN$, which gave Example 36 (0.080 g, 75%).

Electrospray MS $[M+1]^+$ 475.1.

Example 37

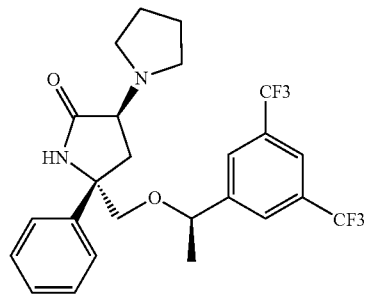

A mixture of Example 35 (0.1 g, 0.22 mmol, 1.0 equiv), $NaHCO_3$ (0.040 mg, 0.47 mmol, 2.1 equiv), 1,4-dibromobutane (0.029 ml, 0.24 mmol, 1.1 equiv), and toluene (2 ml) was heated at 110° C. for 48 hours. The reaction mixture was cooled and taken up in EtOAc (200 ml), and washed with saturated $NaHCO_3$ (100 ml). The organic layer was separated, dried ($Na_2SO_4$), filtered, and concentrated. Purification was accomplished using Gilson and water/$CH_3CN$, which gave Example 37 (0.040 g, 36%).

Electrospray MS $[M+1]^+$ 401.1.

Example 38

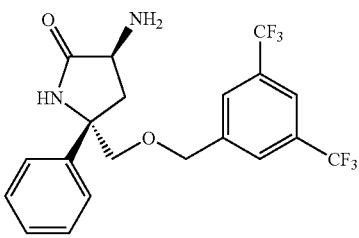

Step 1:

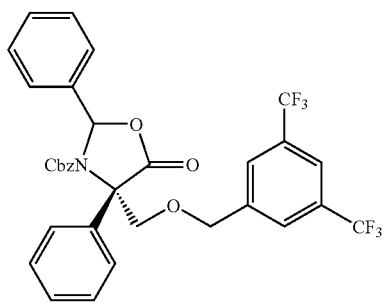

Compound 33 was prepared using a procedure similar to that used for preparing compound 19, but using 1-[(bromomethoxy)methyl-3,5-bis(trifluoromethyl)benzene in place of 1-[(1R)-1-(bromomethoxy)ethyl]-3,5-bis(trifluoromethyl)benzene.

Step 2:

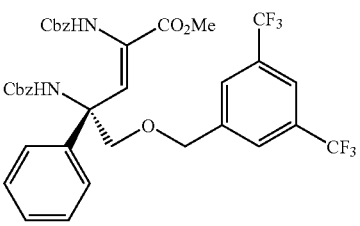

Compound 34 was prepared from compound 33 using a procedure similar to that described above in the preparation of Example 22, Method B, Step 1, reacting compound 6 with $PO(OEt)_2CH(NHCbz)CO_2Me$ in place of $PO(OMe)_2CH(NHBoc)-CO_2Me$. Compound 34 was converted to Example 38 using procedures analogous to those used above to obtain Example 35 from compound 31.

Examples 39a and 39b

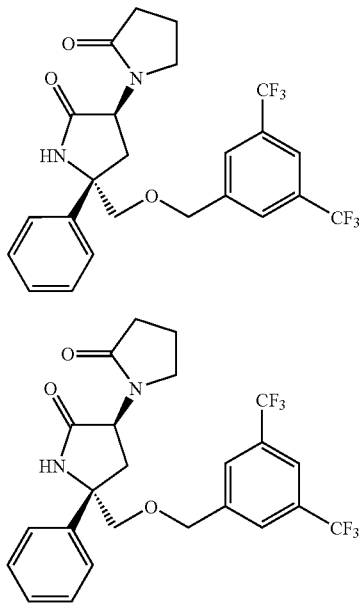

Example 39a

Example 39b

Step 1:

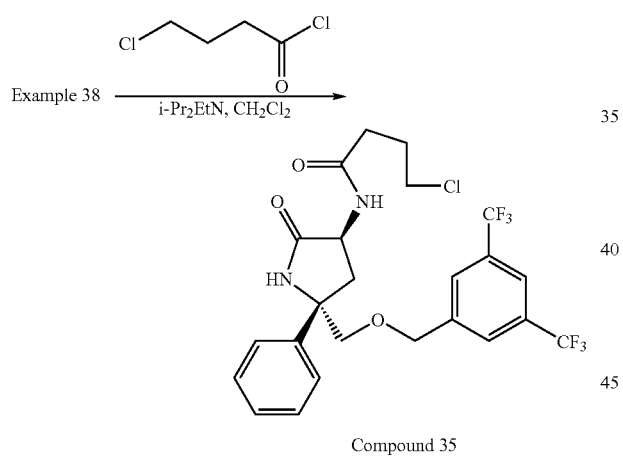

Compound 35

To a solution of amino-lactam Example 38 (0.124 g, 0.287 mmol, 1.0 equiv) in CH$_2$Cl$_2$ (5 ml), was added i-Pr$_2$EtN (0.060 ml, 0.431 mmol, 1.5 equiv). The reaction mixture was cooled to 0° C. and 4-chlorobutyryl chloride (0.039 ml, 0.345 mmol, 1.2 equiv) was added to it. The resulting mixture was stirred at 0° C. for 2 hours. The resulting mixture was then was then taken up in CH$_2$Cl$_2$ (150 ml) and washed with saturated aqueous NaHCO$_3$ (100 ml). The organic layer was dried over anhydrous Na$_2$SO$_4$, filtered, and concentrated to provide the crude compound 35, which was used in the next reaction without further purification.

Step 2:

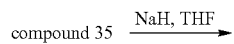

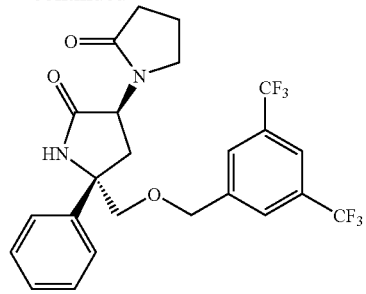

Example 39a

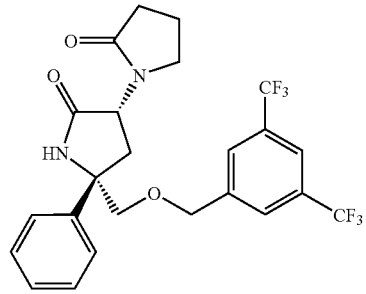

Example 39b

To a solution of crude compound 35 in dry THF (4 ml), was added NaH (60% dispersion in mineral oil, 0.034 g, 0.861 mmol, 3.0 equiv) at 0° C. and the reaction mixture was stirred for 5 minutes, then heated at 60° C. for 2 hours. The reaction mixture was then cooled to 0° C., quenched carefully with water (50 ml), and extracted with EtOAc (2×100 ml). The organic layer was dried over anhydrous Na$_2$SO$_4$, filtered, and concentrated. HPLC separation on a chiralpak OD column using 4:1 hexane/IPA mixture gave Example 39a (0.057 g, 40%) and Example 39b (0.020 g, 14%).

Electrospray MS [M+1]$^+$ 501.1 for Example 39a.
Electrospray MS [M+1]$^+$ 501.1 for Example 39b.

Example 40

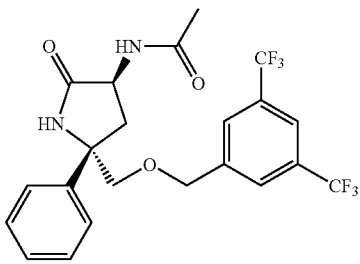

Step 1:

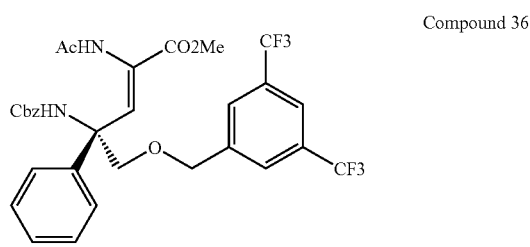

Compound 36

Compound 36 was prepared from compound 33 using a procedure similar to that described above in the preparation of Example 22, Method B, Step 1, reacting compound 6 with PO(OEt)$_2$CH(NHCbz)CO$_2$Me in place of PO(OMe)$_2$CH(NHBoc)CO$_2$Me. Compound 36 was converted to Example 40 using procedures analogous to those used above to obtain Example 38 from compound 34.

Example 41

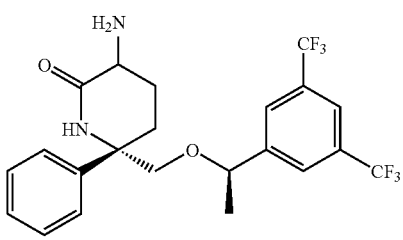

Step 1:

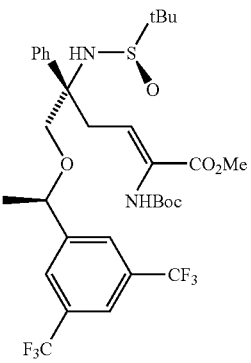

Compound 37

A 15 ml RBF was charged with Compound 29 (245 mg, 0.47 mmol, 1.0 equiv) and CH$_2$Cl$_2$ (2 ml). This pale orange solution was cooled to −78° C., and then O$_3$ was bubbled in at 1.0 ml/min. After the solution turned pale blue, the reaction solution was stirred at −78° C. for 10 minutes. Then it was flushed with N$_2$ to get rid of O$_3$. Tetrabutylammonium iodide (177 mg, 0.47 mmol, 1.0 equiv) was added to break the complex. Then it was quenched with saturated Na$_2$S$_2$O$_3$, and extracted with CH$_2$Cl$_2$. The combined organic layer was dried, filtered, and concentrated, then re-taken up with Et$_2$O, and filtered. The residue on the filter was dissolved in water, and extracted with Et$_2$O. The combined Et$_2$O layer was dried, filtered and concentrated to give Compound 37 (243.5 mg, 99%).

Electrospray MS [M+1]$^+$ 524.1.

Step 2:

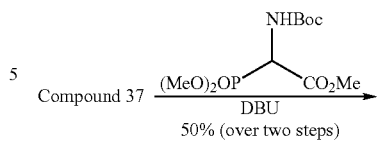

Compound 38

To a solution of Compound 37 (1.2 g, 2.29 mmol, 1:0 equiv.) Boc-Phosphonate (818 mg, 2.75 mmol, 1.2 equiv) in DMF (20 ml) was added Cs$_2$CO$_3$ (2.24 g, 6.87 mmol, 3.0 eqiv). After stirring at RT for 3 hours, the mixture was diluted with Et$_2$O, and washed with water (2×), and Brine. The combined aqueous layer was further extracted with Et$_2$O. The combined organic layer was dried, filtered and concentrated to give crude brownish oil, which was purified by column to give Compound 38 (830 mg, 55%).

Electrospray MS [M+1]$^+$ 695.2.

Step 3:

Compound 38 →[Pd—C/H$_2$] Compound 39

A solution of Compound 38 (830 mg, 1.19 mmol, 1.0 equiv) in EtOH (20 ml) was flushed with N$_2$. After the addition of Palladium on carbon (10%, 1.27 g, 1.19 mmol, 1.0 equiv), a H$_2$ balloon was attached to the reaction flask. The reaction mixture was stirred for almost 24 hours until TLC showed completion of the reaction. The mixture was filtered and concentrated to give Compound 39 as a white solid (790 mg, 95%).

Electrospray MS [M+1]$^+$ 697.2.

Step 4:

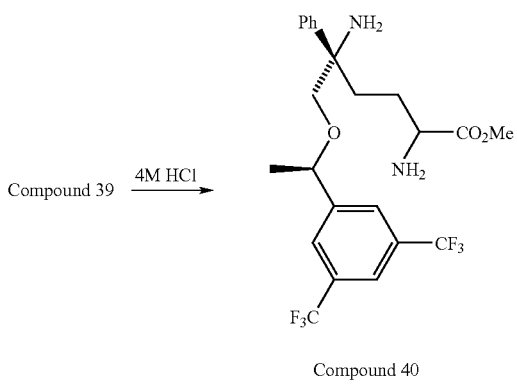

Compound 39 →(4M HCl)

Compound 40

A solution of Compound 39 (400 mg, 0.57 mmol, 1.0 equiv) in anhydrous MeOH (4 ml) was cooled to 0° C., then treated with 4 M solution of HCl in 1,4-dioxane (16 ml). After stirring for 30 minutes at 0° C., it was stirred at RT for another 3 hours. The solvent was evaporated under vacuum to give Compound 40 as a pale brown solid.

Electrospray MS [M+1]$^+$ 493.1.

Step 5:

To a solution of Compound 40 in MeOH (50 ml) was added $K_2CO_3$ (4.5 g). The mixture was stirred for 30 minutes, then filtered, and concentrated to give Compound of Example 41 (199 mg, 76%).

Electrospray MS [M+1]$^+$ 461.1.

Example 42a and 42b

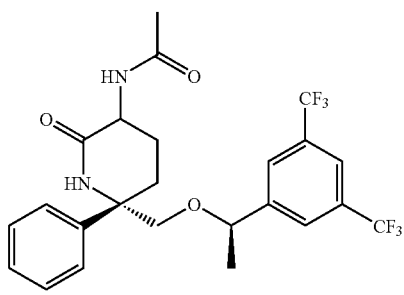

Example 42a

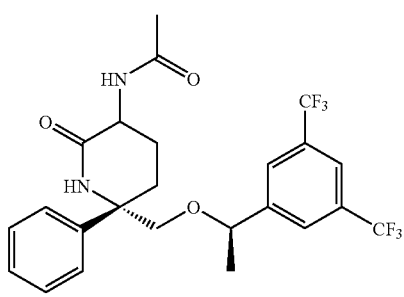

Example 42b

Examples 42a and 42b were prepared from Example 41 using a procedure similar to that used for the preparation of Examples 23a and 23b from Example 22, and using acetic anhydride in place of acetyl chloride. The mixture of isomers was purified using HPLC on a Chiralcel OD column using a (10/90) IPA/hexane solvent mixture to give Example 42a and Example 42b.

Electrospray MS [M+1]$^+$ 503.1 for Example 42a.

Electrospray MS [M+1]$^+$ 503.1 for Example 42b.

Example 43

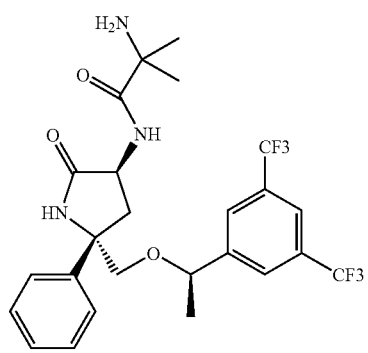

To a mixture of Example 35 (0.098 g, 0.224 mmol, 1 equiv.), NHBoc-acid (0.046 g, 0.224 mmol, 1 equiv.) and HOBT (0.036 g, 0.269 mmol, 1.2 equiv.) in $CH_2Cl_2$ (3 ml) was added DEC (0.065 g, 0.34 mmol, 1.5 equiv.) at 23° C., and the reaction mixture was stirred at 23° C. for 18 hours. The reaction mixture was then washed with saturated $NaHCO_3$, and the aqueous layer was then extracted with $CH_2Cl_2$ (5 ml). The combined organic layers were dried ($MgSO_4$), filtered, and concentrated. The crude material was purified over silica using 30% EtOAc/hexane, then 5% MeOH/$CH_2Cl_2$ to give 100 mg of the desired product, which was dissolved in $CH_2Cl_2$ (2 ml) and 4M HCl/Dioxane (0.3 ml) was added thereto, and the reaction mixture was stirred at 23° C. for one hour. The reaction mixture was then washed with saturated $NaHCO_3$, and the organic layer was dried ($MgSO_4$), filtered, and concentrated to give Example 43 (75 mg, 63%).

Electrospray MS [M+1]$^+$ 532.3.

The above description is not intended to detail all modifications and variations of the invention. It will be appreciated by those skilled in the art that changes can be made to the embodiments described above without departing from the inventive concept. It is understood, therefore, that the invention is not limited to the particular embodiments described above, but is intended to cover modifications that are within the spirit and scope of the invention, as defined by the language of the following claims.

What is claimed is:

1. A compound having the formula (I)

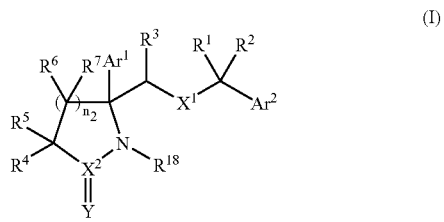

(I)

or a pharmaceutically-acceptable salt thereof, where $Ar^1$ and $Ar^2$ are each independently selected from the group consisting of $R^{17}$-heteroaryl- and

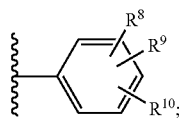

$X^1$ is —O—, —S—, —SO—, —SO$_2$—, —NR$^{18a}$—, —N(COR$^{12}$)— or —N(SO$_2$R$^{15}$)—;

$X^2$ is C;

Y is O, S or NR$^{11}$;

when $X^1$ is —SO—, —SO$_2$—, —N(COR$^{12}$)— or —N(SO$_2$R$^{15}$)—, then:

R$^1$ and R$^2$ are each independently selected from the group consisting of H, —C$_1$–C$_8$ alkyl, hydroxy(C$_1$–C$_3$alkyl)-, —C$_3$–C$_8$ cycloalkyl, —C$_4$–C$_8$ cycloalkylalkyl, —CH$_2$F, —CHF$_2$ and —CF$_3$; or R$^1$ and R$^2$, together with one another and the carbon to which they are both attached, form a C$_3$–C$_8$ alkylene ring;

when $X^1$ is —O—, —S— or —NR$^{18a}$, then:

R$^1$ and R$^2$ are each independently selected from the group consisting of H, —C$_1$–C$_6$ alkyl, hydroxy(C$_1$–C$_3$alkyl)-, —C$_3$–C$_8$ cycloalkyl, —C$_4$–C$_8$ cycloalkylalkyl, —CH$_2$F, —CHF$_2$ and —CF$_3$; or R$^1$ and R$^2$, together with one another and the carbon to which they are both attached, form a C$_3$–C$_8$ alkylene ring; or R$^1$ and R$^2$, together with one another and the carbon to which they are both attached, form a C=O group;

R$^3$ is selected from the group consisting of H, —C$_1$–C$_8$ alkyl, hydroxy(C$_1$–C$_3$ alkyl)-, —C$_3$–C$_8$ cycloalkyl, —CH$_2$F, —CHF$_2$ and —CF$_3$;

each R$^6$ is independently selected from the group consisting of H, —C$_1$–C$_8$ alkyl, —OR$^{13}$ and —SR$^{18}$;

each R$^7$ is independently selected from the group consisting of H and C$_1$–C$_8$ alkyl; or R$^6$ and R$^7$, together with one another and the carbon to which they are both attached, form a C=O group;

n$_2$ is from 1 to 4;

R$^4$ and R$^5$ are each independently selected from the group consisting of —(CR$^{28}$R$^{29}$)$_{n1}$-G and —C(O)(CR$^{28}$R$^{29}$)$_{n4}$-G, where, n$_1$ is from 0 to 5;

n$_4$ is from 1 to 5; and

G is H, —CF$_3$, —CHF$_2$, —CH$_2$F, —OH, —O—(C$_1$–C$_8$ alkyl), —SO$_2$R$^{13}$, —O—(C$_3$–C$_8$ cycloalkyl), —NR$^{13}$R$^{14}$, —SO$_2$NR$^{13}$R$^{14}$, —NR$^{13}$SO$_2$R$^{15}$, —NR$^{13}$COR$^{12}$, —NR$^{12}$(CONR$^{13}$R$^{14}$), —NR$^{12}$COC(R$^{12}$)$_2$NR$^{13}$R$^{14}$, —CONR$^{13}$R$^{14}$, —COOR$^{12}$, —C$_3$–C$_8$ cycloalkyl, (R$^{19}$)$_r$aryl-, (R$^{19}$)$_r$heteroaryl-, —OC(O)R$^{14}$, —OC(O)NR$^{13}$R$^{14}$,

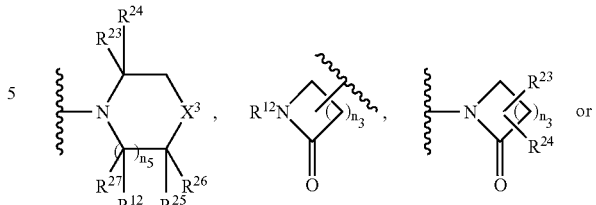

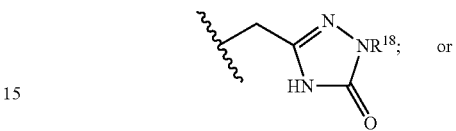

R$^4$ and R$^5$, together with one another and the carbon to which they are both attached, form a C=O or C=NR$^{12}$ group; or R$^4$ and R$^5$, together with one another and the carbon to which they are both attached, form a 4- to 7-membered ring containing from 0 to 3 heteroatoms that are each independently selected from the group consisting of —O—, —S—, —S(O)—, —SO$_2$— and —NR$^{18}$—, the ring being optionally substituted with from 1 to 2 substituents that are independently selected from the group consisting of R$^{30}$ and R$^{31}$; or when R$^4$ and R$^5$ do not form a ring, and n$_2$ is 1 or 2, then R$^4$ and R$^6$ or R$^4$ and R$^7$, which are on adjacent carbons, can form a bond;

$X^3$ is —NR$^{20}$—, —N(CONR$^{13}$R$^{14}$)—, —N(CO$_2$R$^{13}$)—, —N(SO$_2$R$^{15}$)—, —N(COR$^{12}$)—, —N(SO$_2$NHR$^{13}$)—, —O—, —S—, —S(O)—, —SO$_2$—, —CH$_2$—, —CF$_2$— or —CR$^{12}$F—;

R$^8$, R$^9$ and R$^{10}$ are each independently selected from the group consisting of H, —C$_1$–C$_6$ alkyl, —C$_3$–C$_8$ cycloalkyl, —OR$^{18}$, halogen, —CN, —NO$_2$, —CF$_3$, —CHF$_2$, —CH$_2$F, —CH$_2$CF$_3$, —OCF$_3$, —OCHF$_2$, —OCH$_2$F, —OCH$_2$CF$_3$, —COOR$^{12}$, —CONR$^{21}$R$^{22}$, —NR$^{21}$COR$^{12}$, —NR$^{21}$CO$_2$R$^{15}$, —NR$^{21}$CONR$^{21}$R$^{22}$, —NR$^{21}$SO$_2$R$^{15}$, —NR$^{21}$R$^{22}$, —SO$_2$NR$^{21}$R$^{22}$, —S(O)$_{n5}$R$^{15}$, (R$^{19}$)$_r$aryl- and (R$^{19}$)$_r$heteroaryl-;

R$^{11}$ is H, —C$_1$–C$_6$ alkyl, —C$_3$–C$_8$ cycloalkyl, —C$_4$–C$_8$ cycloalkylalkyl, —NO$_2$, —CN or —OR$^{18}$;

R$^{12}$ is H, —C$_1$–C$_6$ alkyl, —C$_3$–C$_8$ cycloalkyl or —C$_4$–C$_8$ cycloalkylalkyl;

R$^{13}$ and R$^{14}$ are each independently selected from the group consisting of H, —C$_1$–C$_6$ alkyl, —C$_3$–C$_8$ cycloalkyl or —C$_4$–C$_8$ cycloalkylalkyl; or R$^{13}$ and R$^{14}$, together with one another, form a —C$_3$ to —C$_6$ alkylene chain, and with the nitrogen to which they are both attached, form a 4- to 7-membered ring that is, optionally, substituted with —OR$^{12}$, where one of the carbon atoms in the C$_3$–C$_6$ alkylene chain is, optionally, replaced by a heteroatom selected from the group consisting of —O—, —S— and —NR$^{18}$—;

R$^{15}$ is —C$_1$–C$_6$ alkyl, —C$_3$–C$_8$ cycloalkyl, —C$_4$–C$_8$ cycloalkylalkyl or —CF$_3$;

R$^{17}$ is H, —C$_1$–C$_6$ alkyl, —C$_3$–C$_8$ cycloalkyl, —C$_4$–C$_8$ cycloalkylalkyl, —COOR$^{12}$, —CONR$^{21}$R$^{22}$, —NR$^{21}$R$^{22}$, —NR$^{21}$COR$^{12}$, —NR$^{21}$CO$_2$R$^{12}$, —NR$^{21}$CONR$^{21}$R$^{22}$, —NR$^{21}$SO$_2$R$^{15}$ or —S(O)$_{n5}$R$^{15}$;

each R$^{18}$ is independently selected from the group consisting of H, —C$_1$–C$_6$ alkyl, —C$_3$–C$_8$ cycloalkyl, —C$_4$–C$_8$ cycloalkylalkyl and —P(O)(OH)$_2$;

each $R^{18a}$ is independently selected from the group consisting of H, —$C_1$–$C_6$ alkyl, —$C_3$–$C_8$ cycloalkyl and —$C_4$–$C_8$ cycloalkylalkyl;

each $R^{19}$ is a substituent on the aryl or heteroaryl ring to which it is attached, and is independently selected from the group consisting of H, —$C_1$–$C_6$ alkyl, —$C_3$–$C_8$ cycloalkyl, —$C_4$–$C_8$ cycloalkylalkyl, —$C_1$–$C_6$ alkoxy, —OH, halogen, —CN, —$NO_2$, —$CF_3$, —$CHF_2$, —$CH_2F$, —$OCF_3$, —$OCHF_2$, —$OCH_2F$, —O—($C_1$–$C_6$ alkyl), —O—($C_3$–$C_8$ cycloalkyl), —$COOR^{12}$, —$CONR^{21}R^{22}$, —$NR^{21}R^{22}$, —$NR^{21}COR^{12}$, —$NR^{21}CO_2R^{12}$, —$NR^{21}CONR^{21}R^{22}$, —$NR^{21}SO_2R^{15}$ and —$S(O)_{n5}R^{15}$;

r is from 1 to 3;

$R^{20}$ is H, —$C_1$–$C_6$ alkyl, —$C_3$–$C_8$ cycloalkyl, —$C_4$–$C_8$ cycloalkylalkyl or —$(CH_2)_{n6}$—heterocycloalkyl;

$R^{21}$ and $R^{22}$ are each independently selected from the group consisting of H, —$C_1$–$C_6$ alkyl, —$C_3$–$C_8$ cycloalkyl, —$C_4$–$C_8$ cycloalkylalkyl and benzyl; or $R^{21}$ and $R^{22}$, together with one another, form a —$C_3$–$C_6$ alkylene chain, and with the nitrogen to which they are both attached, form a 4- to 7-membered ring, where one of the carbon atoms in the —$C_3$–$C_6$ alkylene chain is, optionally, replaced by a heteroatom selected from the group consisting of —O—, —S— and —$NR^{18}$—;

$R^{23}$ and $R^{24}$ are each independently selected from the group consisting of H and —$C_1$–$C_6$ alkyl; or $R^{23}$ and $R^{24}$, together with one another and the carbon to which they are both attached, form a C=O or cyclopropyl group;

$R^{25}$ and $R^{26}$ are each independently selected from the group consisting of H and —$C_1$–$C_6$ alkyl; or $R^{25}$ and $R^{26}$, together with one another and the carbon to which they are both attached, form a C=O or cyclopropyl group;

$R^{27}$ is H or —$C_1$–$C_6$ alkyl;

$R^{28}$ and $R^{29}$ are each independently selected from the group consisting of H, —$C_1$–$C_2$ alkyl, —$CH_2F$, —$CHF_2$ and —$CF_3$;

$R^{30}$ and $R^{31}$ are each independently selected from the group consisting of H, —$C_1$–$C_2$ alkyl, —$CH_2F$, —$CHF_2$ and —$CF_3$; or $R^{30}$ and $R^{31}$, together with one another and the carbon to which they are both attached, form a C=O or cyclopropyl group;

$n_3$ is from 1 to 5;

$n_5$ is from 0 to 2; and $n_6$ is from 0 to 3;

provided that, when $n_5$ is 0, and $R^{25}$ and $R^{26}$ are each H, then $X^3$ is —$CH_2$—, —$CF_2$— or —$CR^{12}F$—;

or a diastereomer, enantiomer, stereoisomer, regiostereomer, rotamer, tautomer or prodrug thereof.

2. The compound or salt according to claim 1, where $X^1$ is —O—.

3. The compound or salt according to claim 1, where $Ar^1$ and $Ar^2$ are each

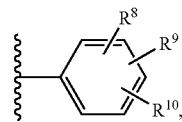

where $R^8$, $R^9$ and $R^{10}$ are each defined in claim 1.

4. The compound or salt according to claim 3, where for $Ar^2$, at least two of $R^8$, $R^9$ and $R^{10}$ are each —$CF_3$.

5. The compound or salt according to claim 3, where for $Ar^1$, $R^8$, $R^9$ and $R^{10}$ are each independently selected from the group consisting of H, —OH and halogen.

6. The compound or salt according to claim 1, where $X^2$ is —C— and Y is O.

7. The compound or salt according to claim 1, where one of $R^4$ and $R^5$ is H, and the other one of $R^4$ and $R^5$ is —$C(R^{28}R^{29})_{n1}$-G, where $n_1$ is 0 or 1, and $R^{28}$, $R^{29}$ and G are each defined in claim 1.

8. The compound or salt according to claim 7, where one of $R^4$ and $R^5$ is H, and the other one of $R^4$ and $R^5$ is H, —$CH_3$, —$NHCOR^{12}$ or

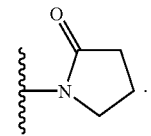

9. The compound or salt according to claim 1, where $R^4$ and $R^5$, together with one another and the carbon to which they are both attached, form a 4- to 7-membered ring containing from 0 to 3 heteroatoms that are each independently selected from the group consisting of —O—, —S—, —S(O)—, —$SO_2$— and —$NR^{18}$—, the ring being optionally substituted with from 1 to 2 substituents that are each independently selected from the group consisting of $R^{30}$ and $R^{31}$, where $R^{15}$, $R^{30}$ and $R^{31}$ are each defined in claim 1.

10. The compound or salt according to claim 9, where $R^4$ and $R^5$, together with one another and the carbon to which they are both attached, form a chemically feasible 4- to 7-membered ring selected from the group consisting of:

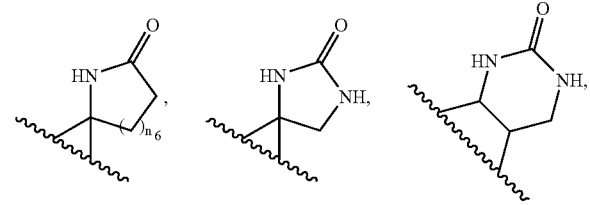

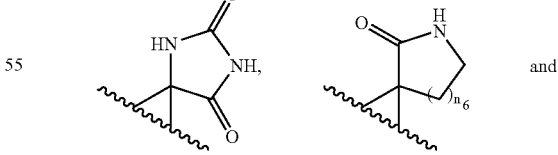

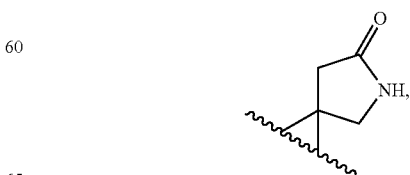

where $n_6$ is defined in claim 1.

11. The compound or salt according to claim 1, where:

$R^1$ and $R^2$ are each independently defined in claim 1;
$X^1$ is defined in claim 1;
$R^3$ is H;
$Ar^1$ and $Ar^2$, independently of one another, are each

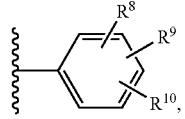

where $R^8$, $R^9$ and $R^{10}$, independently of one another, are each H, —OH, —$CF_3$ or halogen;

$R^6$ and $R^7$ are each H;
$R^4$ and $R^5$, independently of one another, are each defined in claim 1;
$X^2$ is —C—;
Y is O; and
$R^{18}$ is H or —P(O)(OH)$_2$.

12. The compound according to claim 11, where $X^1$ is —O— or —$NR^{18a}$—, $n_2$ is 1 or 2, and $R^4$ and $R^5$ are each independently —C($R^{28}R^{29}$)$_{n1}$-G, where $n_1$, $R^{28}$, $R^{29}$ and G are each defined in claim 1.

13. The compound according to claim 11, where $X^1$ is —O— or —$NR^{18a}$—, $n_2$ is 1 or 2, and $R^4$ and $R^5$, together with one another and the carbon to which they are both attached, form a 4- to 7-membered ring selected from the group consisting of:

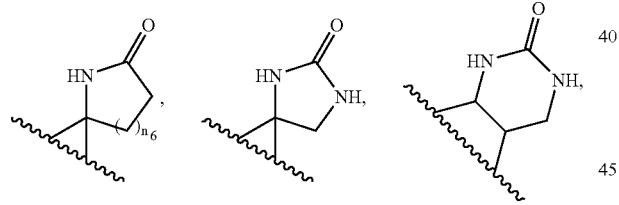

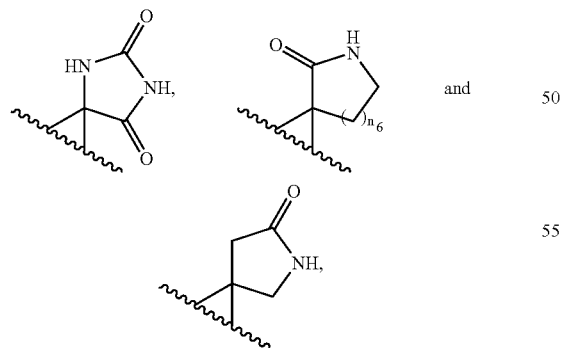

where $n_6$ is defined in claim 1.

14. The compound or salt according to claim 1, wherein the compound is selected from the group consisting of:

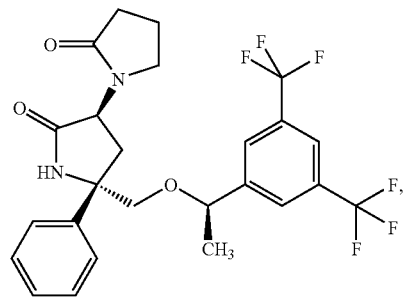

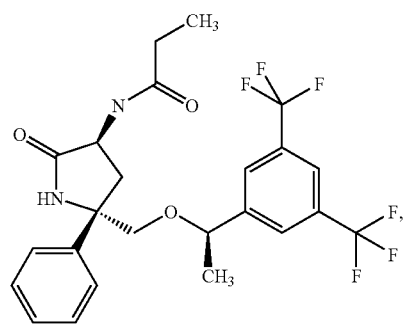

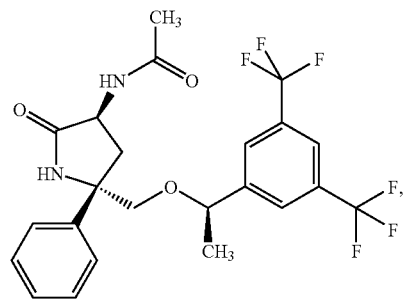

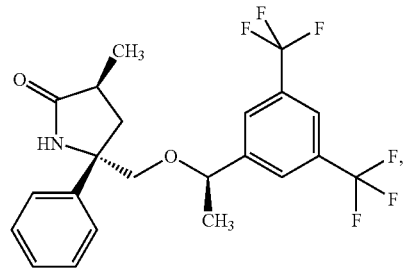

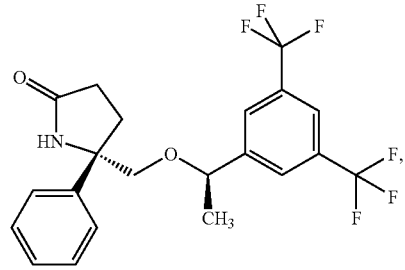

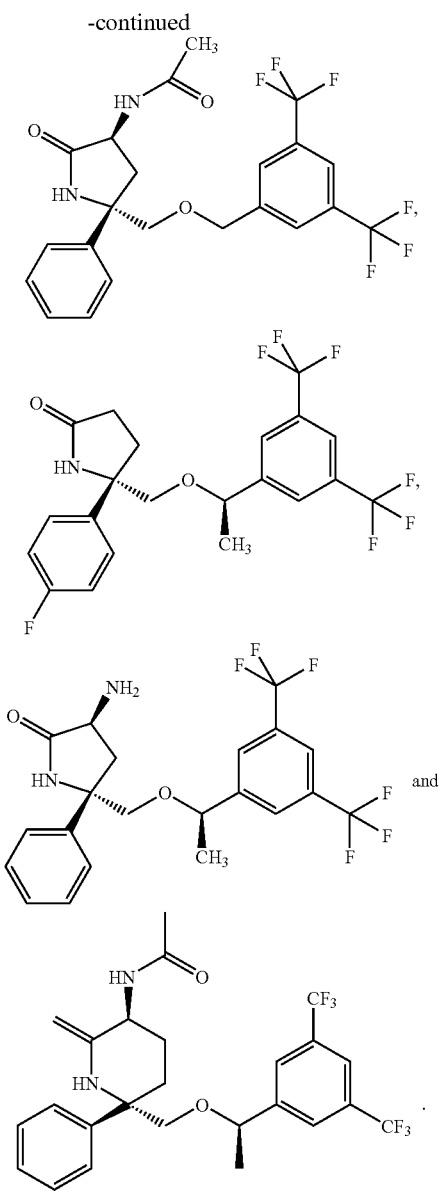

15. A pharmaceutical composition comprising at least one compound or salt according to claim 1 and a pharmaceutical carrier or excipient therefor.

16. The pharmaceutical composition according to claim 15, further comprising at least one selective serotonin reuptake inhibitor.

17. The pharmaceutical composition according to claim 15, further comprising at least one serotonin 5-$HT_3$ receptor antagonist.

18. A method of treating emesis, nausea, depression, anxiety or cough comprising administering an effective amount of at least one compound of claim 1 to a patient in need of such treatment.

19. The method according to claim 18 for treating depression or anxiety, further comprising administering to the patient an effective amount of at least one selective serotonin reuptake inhibitor.

20. The method according to claim 19, where the selective serotonin reuptake inhibitor is fluoxetine, fluvoxamine, paroxetine, sertaline, or a pharmaceutically-acceptable salt thereof.

21. The method according to claim 18 for treating emesis, further comprising administering to the patient an effective amount of at least one serotonin 5-$HT_3$ receptor antagonist.

22. The method according to claim 21, where the serotonin 5-$HT_3$ receptor antagonist is palonsetron, ondansetron, granisetron or a pharmaceutically-acceptable salt thereof.

23. A method for antagonizing an effect of a Substance P at a neurokinin-1 receptor site or for blocking at least one neurokinin-1 receptor, in a mammal in need of such treatment, comprising administering to the mammal an effective amount of at least one compound or salt according to claim 1, or a pharmaceutical composition thereof.

* * * * *

UNITED STATES PATENT AND TRADEMARK OFFICE
CERTIFICATE OF CORRECTION

PATENT NO. : 7,122,677 B2 Page 1 of 1
APPLICATION NO. : 10/292618
DATED : October 17, 2006
INVENTOR(S) : Gregory A. Reichard et al.

It is certified that error appears in the above-identified patent and that said Letters Patent is hereby corrected as shown below:

On the title of the Patent, item (73) Assignee, replace "Scherig" and insert -- Schering --.

Column 67
Claim 1, Line 19, replace "-$C_1$-$C_8$" with -- -$C_1$-$C_6$ --.
Claim 1, Line 24, replace "$C_3$-$C_8$" with -- $C_3$-$C_6$ --.
Claim 1, Line 34, replace "$C_3$-$C_8$" with -- $C_3$-$C_6$ --.
Claim 1, Line 39, replace "-$C_1$-$C_8$" with -- -$C_1$-$C_6$ --.
Claim 1, Line 44, replace "-$C_1$-$C_8$" with -- -$C_1$-$C_6$ --.
Claim 1, Line 46, replace "$C_1$-$C_8$" with -- $C_1$-$C_6$ --.
Claim 1, Line 60, replace "($C_1$-$C_8$ alkyl)" with -- ($C_1$-$C_6$ alkyl) --.

Column 70
Claim 9, Line 38, replace "$R^{15}$" with -- $R^{18}$ --.

Signed and Sealed this

Ninth Day of January, 2007

JON W. DUDAS
*Director of the United States Patent and Trademark Office*